US010633680B2

(12) United States Patent
Smanski et al.

(10) Patent No.: US 10,633,680 B2
(45) Date of Patent: Apr. 28, 2020

(54) RECOMBINANT CELLS AND METHODS FOR BIOSYNTHESIS OF ENT-ATISERENOIC ACID

(71) Applicant: REGENTS OF THE UNIVERSITY OF MINNESOTA, Minneapolis, MN (US)

(72) Inventors: Michael Joseph Smanski, Falcon Heights, MN (US); Szu-Yi Hsu, Falcon Heights, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/466,352

(22) Filed: Mar. 22, 2017

(65) Prior Publication Data

US 2017/0275659 A1 Sep. 28, 2017

Related U.S. Application Data

(60) Provisional application No. 62/311,596, filed on Mar. 22, 2016.

(51) Int. Cl.

| | |
|---|---|
| ***C12N 1/20*** | (2006.01) |
| ***C12P 15/00*** | (2006.01) |
| ***C12N 15/52*** | (2006.01) |
| ***C12N 9/88*** | (2006.01) |
| ***C12N 9/10*** | (2006.01) |

(52) U.S. Cl.

CPC ................ *C12P 15/00* (2013.01); *C12N 1/20* (2013.01); *C12N 9/1085* (2013.01); *C12N 9/88* (2013.01); *C12N 15/52* (2013.01); *C12Y 205/01039* (2013.01)

(58) Field of Classification Search

None

See application file for complete search history.

(56) References Cited

U.S. PATENT DOCUMENTS

2009/0081673 A1* 3/2009 Shen .................... C12N 9/1085 435/6.11

2017/0275659 A1* 9/2017 Smanski ................ C12P 15/00

OTHER PUBLICATIONS

Hindra et al., "Strain prioritization for natural product discovery by a high-throughput real-time PCR method", Journal of Natural Products, vol. 77, pp. 2296-2303, 2014.*

(Continued)

*Primary Examiner* — Richard C Ekstrom

(74) *Attorney, Agent, or Firm* — Mueting, Raasch & Gebhardt, P.A.

(57) ABSTRACT

This disclosure describes recombinant cells and methods for microbial biosynthesis of ent-atiserenoic acid. Thus, in one aspect, this disclosure describes a recombinant cell genetically modified to exhibit increased biosynthesis of ent-atiserenoic acid compared to a comparable control cell. In some cases, the recombinant cell can include a host cell modified to include at least one heterologous polynucleotide encoding at least one enzyme in a biosynthetic pathway that produces ent-atiserenoic acid. In some cases, the recombinant cell can include a host cell and at least one heterologous enzyme in a biosynthetic pathway that produces ent-atiserenoic acid.

5 Claims, 24 Drawing Sheets

Specification includes a Sequence Listing.

(56) References Cited

OTHER PUBLICATIONS

Smanski et al., "Dedicated ent-kaurene and ent-atiserene synthases for platensimycin and platencin biosynthesis", Proceedings of the National Academy of Sciences USA, vol. 108, No. 33, pp. 13498-13503, 2011.*

Smanski et al., "Platensimycin and platencin biosynthesis in Streptomyces platensis, showcasing discovery and characterization of novel bacterial diterpene synthases", Methods in Enzymology, vol. 515, pp. 163-186, 2012.*

Akaike, "Pharmacological and physiological properties of serofendic acid, a novel neuroprotective substance isolated from fetal calf serum" 2003 *Life Sci.*, 74:263-269.

Akao, "Serofendic acid, a substance extracted from fetal calf serum, as a novel drug for cardioprotection" 2007 *Cardiovasc. Drug Rev.*, 25:333-341.

Chen, "Characterization of 582 natural and synthetic terminators and quantification of their design constraints" Jul. 2013 *Nat. Methods*, 10(7):659-64.

Doi, "The Direct and Indirect Effects of Serofendic Acid on Neuroprotection" 2006 *Ann. N.Y. Acad. Sci.*, 91-103. doi:10.1196.

Dong, "Molecular mechanisms of excitotoxicity and their relevance to pathogenesis of neurodegenerative diseases" Apr. 2009 *Acta Pharmacol. Sin.*, 30:379-387.

Doroghazi, "A Roadmap for Natural Product Discovery Based on Large-Scale Genomics and Metabolomics" Nov. 2014 *Nat. Chem. Biol.*, 10:963-968.

Ioroi, "Protective effect of serofendic acid, administered intravenously, on cerebral ischemia-reperfusion injury in rats" 2013 *Brain Res.*, 1532:99-105.

Ioroi, "Serofendic Acid Protects Against Myocardial Ischemia—Reperfusion Injury in Rats" 2014 *J. Pharmacol. Sci.*, 280:274-280.

Kinkel, "A Coevolutionary Framework for Managing Disease-Suppressive Soils" Nov. 2011 *Annual Review of Phytopathology*, 49:47-67.

Kita, "Serofendic acid promotes survival of auditory hair cells and neurons of mice" May 2005 *Neuroreport*, 16:689-692.

Kume, "Ether extract of fetal calf serum protects cultured rat cortical neurons against glutamate cytotoxicity" *Jpn.J Pharmacol.*, 73:371-374, (1997).

Kume, "Isolation of a diterpenoid substance with potent neuroprotective activity from fetal calf serum" 2002 *Proc. Natl. Acad. Sci. U. S. A.*, 99:3288-3293.

Kume, "Protective effect of serofendic acid on glutamate-induced neurotoxicity in rat cultured motor neurons" 2005 *Neurosci. Lett.*, 383:199-202.

Kume, "Serofendic acid promotes stellation induced by cAMP and cGMP analogs in cultured cortical astrocytes" 2009 *J. Pharmacol. Sci.*, 109:110-8.

Kume, "Serofendic acid, a neuroprotective substance derived from fetal calf serum, inhibits mitochondrial membrane depolarization and caspase-3 activation" 2006 *Eur. J. Pharmacol.*, 542:69-76.

Mark, "Pictorial review of glutamate excitotoxicity: Fundamental concepts for neuroimaging" 2001 *Am. J. Neuroradiol.*, 22:1813-1824.

Martin, "The mitochondrial permeability transition pore regulates nitric oxide-mediated apoptosis of neurons induced by target deprivation" Dec. 2011 *J Neurosci.*, 31, 359-370.

Oerke, "Crop losses to pests" 2006 *J. Agric. Sci.*, 144:31.

Osakada, "Serofendic acid, a sulfur-containing diterpenoid derived from fetal calf serum, attenuates reactive oxygen species-induced oxidative stress in cultured striatal neurons" Oct. 2004 *J. Pharmacol. Exp. Ther.*, 311, 51-59.

Shepherd: "Laboratory Maintenance of *Streptomyces* species" 2010 *Curr Protoc Microbiol. CHAPTER*, Unit-10E.1. http://doi.org/10.1002/9780471729259.mc10e01s18.

Siegl, "Design, construction and characterisation of a synthetic promoter library for fine-tuned gene expression in actinomycetes" Sep. 2013 *Metabolic Engineering*, 19:98-106.

Taguchi, "Serofendic acid prevents acute glutamate neurotoxicity in cultured cortical neurons" Sep. 2003 *Eur. J. Pharmacol.*, 477:195-203.

Terauchi, "Synthesis and pharmacological profile of serofendic acids A and B" Nov. 2007 *Bioorg. Med. Chem.*, 15:7098-107.

Toyota, "Total synthesis of serofendic acids A and B employing tin-free homoallyl-homoallyl radical rearrangement" Sep. 2005 *Org. Lett.*, 7:3929-32.

* cited by examiner a *ent*-atiserenoic acid b Key COSY (bold) and HMBC (arrows) correlations c Key NOESY correlations

FIG. 22

<table>
<tr><th>Partial cluster</th><th colspan="3">M</th><th colspan="3">T</th><th colspan="3">O</th></tr>
<tr><th></th><th>ptmM1</th><th>ptmM2</th><th>ptmM3</th><th>ptmT1</th><th>ptmT2</th><th>ptmT4</th><th>ptmO2</th><th>ptmO6</th><th>ptmO9</th></tr>
<tr><td>1</td><td rowspan="6">High<br>P[11] RBS[10] T[1]</td><td rowspan="6">Med<br>P[4] RBS[6] T[3]</td><td rowspan="6">Med<br>P[5] RBS[7] T[2]</td><td rowspan="2">Low<br>P[1] RBS[1] T[4]</td><td rowspan="2">High<br>P[9] RBS[9] T[5]</td><td rowspan="2">Med<br>P[5] RBS[5] T[10]</td><td>Med<br>P[4] RBS[6] T[3]</td><td></td><td>High<br>P[12] RBS[9] T[9]</td></tr>
<tr><td>2</td><td></td><td>High<br>P[12] RBS[10] T[5]</td><td></td></tr>
<tr><td>3</td><td rowspan="4">High<br>P[9] RBS[7] T[4]</td><td rowspan="4">High<br>P[8] RBS[6] T[5]</td><td rowspan="4">High<br>P[10] RBS[10] T[6]</td><td>Med<br>P[4] RBS[6] T[3]</td><td>Med<br>P[5] RBS[7] T[2]</td><td>Low<br>P[1] RBS[1] T[9]</td></tr>
<tr><td>4</td><td>Med<br>P[4] RBS[6] T[3]</td><td>Med<br>P[5] RBS[7] T[2]</td><td>High<br>P[12] RBS[9] T[9]</td></tr>
<tr><td>5</td><td>Med<br>P[4] RBS[6] T[3]</td><td></td><td>High<br>P[12] RBS[9] T[9]</td></tr>
<tr><td>6</td><td></td><td>High<br>P[12] RBS[10] T[5]</td><td></td></tr>
</table>

SEQUENCE LISTING

<160> NUMBER OF SEQ ID NOS: 31

<210> SEQ ID NO 1
<211> LENGTH: 36
<212> TYPE: DNA
<213> ORGANISM: artificial
<220> FEATURE:
<223> OTHER INFORMATION: primer

<400> SEQUENCE: 1
attacacctg cttataatga cgtcggaact gcccgc 36

<210> SEQ ID NO 2
<211> LENGTH: 40
<212> TYPE: DNA
<213> ORGANISM: artificial
<220> FEATURE:
<223> OTHER INFORMATION: primer

<400> SEQUENCE: 2
attacacctg cttatgtgcc gcgcacgtga acgcggtgcg 40

<210> SEQ ID NO 3
<211> LENGTH: 37
<212> TYPE: DNA
<213> ORGANISM: artificial
<220> FEATURE:
<223> OTHER INFORMATION: primer

<400> SEQUENCE: 3
attacacctg cttatgcact ggagatggcg ctcgccc 37

-continued

<210> SEQ ID NO 4
<211> LENGTH: 38
<212> TYPE: DNA
<213> ORGANISM: artificial
<220> FEATURE:
<223> OTHER INFORMATION: primer

<400> SEQUENCE: 4
attacacctg cttatatcag agcgcgagca gcgggatg 38

<210> SEQ ID NO 5
<211> LENGTH: 36
<212> TYPE: DNA
<213> ORGANISM: artificial
<220> FEATURE:
<223> OTHER INFORMATION: primer

<400> SEQUENCE: 5
attacacctg cttataatga ccacccgccc cacggc 36

<210> SEQ ID NO 6
<211> LENGTH: 37
<212> TYPE: DNA
<213> ORGANISM: artificial
<220> FEATURE:
<223> OTHER INFORMATION: primer

<400> SEQUENCE: 6
attacacctg cttatatcat gctggacact cggtcac 37

<210> SEQ ID NO 7
<211> LENGTH: 37
<212> TYPE: DNA
<213> ORGANISM: artificial
<220> FEATURE:
<223> OTHER INFORMATION: primer

<400> SEQUENCE: 7
attacacctg cttataatgc tcgaagttcc cgctcag 37

<210> SEQ ID NO 8
<211> LENGTH: 37
<212> TYPE: DNA
<213> ORGANISM: artificial
<220> FEATURE:
<223> OTHER INFORMATION: primer

<400> SEQUENCE: 8
attacacctg cttatatcaa gcacctccgg aagcggc 37

<210> SEQ ID NO 9
<211> LENGTH: 36
<212> TYPE: DNA
<213> ORGANISM: artificial
<220> FEATURE:
<223> OTHER INFORMATION: primer

<400> SEQUENCE: 9
attacacctg cttataatgt gggagccgac gtctgc 36

<210> SEQ ID NO 10
<211> LENGTH: 37
<212> TYPE: DNA
<213> ORGANISM: artificial
<220> FEATURE:
<223> OTHER INFORMATION: primer

<400> SEQUENCE: 10
attacacctg cttatatcac gcggcggtgt tctgctg 37

<210> SEQ ID NO 11
<211> LENGTH: 37
<212> TYPE: DNA
<213> ORGANISM: artificial
<220> FEATURE:
<223> OTHER INFORMATION: primer

<400> SEQUENCE: 11
attacacctg cttataatgc acgctgacac agtccag 37

<210> SEQ ID NO 12
<211> LENGTH: 43
<212> TYPE: DNA
<213> ORGANISM: artificial
<220> FEATURE:
<223> OTHER INFORMATION: primer

<400> SEQUENCE: 12
attacacctg cttatcgacg ggaatggact tcttcttgtt gtg 43

<210> SEQ ID NO 13
<211> LENGTH: 36
<212> TYPE: DNA
<213> ORGANISM: artificial
<220> FEATURE:
<223> OTHER INFORMATION: primer

<400> SEQUENCE: 13
attacacctg cttatgtcgt cgccgccctc cacagc 36

<210> SEQ ID NO 14
<211> LENGTH: 37
<212> TYPE: DNA
<213> ORGANISM: artificial
<220> FEATURE:
<223> OTHER INFORMATION: primer

<400> SEQUENCE: 14
attacacctg cttatatcag tgcttcctga aggcgac 37

<210> SEQ ID NO 15
<211> LENGTH: 36
<212> TYPE: DNA
<213> ORGANISM: artificial
<220> FEATURE:
<223> OTHER INFORMATION: primer

<400> SEQUENCE: 15
attacacctg cttataatga ccgccgccat cgtgag 36

<210> SEQ ID NO 16
<211> LENGTH: 38
<212> TYPE: DNA
<213> ORGANISM: artificial
<220> FEATURE:
<223> OTHER INFORMATION: primer

<400> SEQUENCE: 16
attacacctg cttatatcaa cagctgtcaa cggtcttc 38

<210> SEQ ID NO 17
<211> LENGTH: 36

<212> TYPE: DNA
<213> ORGANISM: artificial
<220> FEATURE:
<223> OTHER INFORMATION: primer

<400> SEQUENCE: 17
attacacctg cttataatgc cgacgacacc gctgcg 36

<210> SEQ ID NO 18
<211> LENGTH: 39
<212> TYPE: DNA
<213> ORGANISM: artificial
<220> FEATURE:
<223> OTHER INFORMATION: primer

<400> SEQUENCE: 18
attacacctg cttatgtgct ccgcgaacag ctccgcctc 39

<210> SEQ ID NO 19
<211> LENGTH: 37
<212> TYPE: DNA
<213> ORGANISM: artificial
<220> FEATURE:
<223> OTHER INFORMATION: primer

<400> SEQUENCE: 19
attacacctg cttatgcacg acttccacga cttcaag 37

<210> SEQ ID NO 20
<211> LENGTH: 37
<212> TYPE: DNA
<213> ORGANISM: artificial
<220> FEATURE:
<223> OTHER INFORMATION: primer

<400> SEQUENCE: 20
attacacctg cttatatcag ccagtctcat cgaggtc 37

<210> SEQ ID NO 21
<211> LENGTH: 36
<212> TYPE: DNA
<213> ORGANISM: artificial
<220> FEATURE:
<223> OTHER INFORMATION: primer

<400> SEQUENCE: 21
attacacctg cttataatga gactggctga cctcac 36

<210> SEQ ID NO 22
<211> LENGTH: 40
<212> TYPE: DNA
<213> ORGANISM: artificial
<220> FEATURE:
<223> OTHER INFORMATION: primer

<400> SEQUENCE: 22
attacacctg cttatgtggc cggtgtcgaa cagcagggtg 40

<210> SEQ ID NO 23
<211> LENGTH: 37
<212> TYPE: DNA
<213> ORGANISM: artificial
<220> FEATURE:
<223> OTHER INFORMATION: primer

<400> SEQUENCE: 23
attacacctg cttatccacc aggcctacgt ccacaag 37

<210> SEQ ID NO 24
<211> LENGTH: 36
<212> TYPE: DNA
<213> ORGANISM: artificial
<220> FEATURE:
<223> OTHER INFORMATION: primer

<400> SEQUENCE: 24
attacacctg cttatatcag cgcggggccg cttgtg 36

<210> SEQ ID NO 25
<211> LENGTH: 30
<212> TYPE: DNA
<213> ORGANISM: artificial
<220> FEATURE:
<223> OTHER INFORMATION: primer

<400> SEQUENCE: 25
ggctcccaca ccagcccagc caccagccag 30

<210> SEQ ID NO 26
<211> LENGTH: 27
<212> TYPE: DNA
<213> ORGANISM: artificial
<220> FEATURE:
<223> OTHER INFORMATION: primer

<400> SEQUENCE: 26
catcgagggg catgggaagg ccttctg 27

<210> SEQ ID NO 27
<211> LENGTH: 38
<212> TYPE: DNA
<213> ORGANISM: artificial
<220> FEATURE:
<223> OTHER INFORMATION: primer

<400> SEQUENCE: 27
attacacctg cttataatga cgtacgtaat cgcgcagc 38

<210> SEQ ID NO 28
<211> LENGTH: 38
<212> TYPE: DNA
<213> ORGANISM: artificial
<220> FEATURE:
<223> OTHER INFORMATION: primer

<400> SEQUENCE: 28
attacacctg cttatatcat tcgcccgcgg ctccggcc 38

<210> SEQ ID NO 29
<211> LENGTH: 11442
<212> TYPE: DNA
<213> ORGANISM: Streptomyces albus

<400> SEQUENCE: 29
gctcttcgga gccgggcggc ttcctcatgc ttgacttgac taggataaag gggctacaag 60
gaagaaggag gttaacaaat gaccgccgcc atcgtgagtg tcgccgcccg cccgctgagc 120
acggcggtgc gccacggcga cgtggtgctc gccgaccggc tgcacctggc gtcgggcgcc 180
cgcgagggcc gggtccaccg gctgctcgcc ggggccctca gggcacaggg gctgacggtc 240
cacaccggcg gggccgccgt cgccggcgcc gaggcacccc agggcgccga cgcaccgctg 300

```
gtggagatcg ccgcgccggt ccggctcccg gaggcggacg gtgacgcgct gctgtgcctg    360
gtgcgcgacg acaccggatc ggacgccgtc gaccgcgccg aggaggccct ggcccgggtc    420
ctgggcgact gggaagccgc gaagggggac cgagcggtgg ccctggccgc cccccggtcg    480
ttctgcgccg gtgtggaccg tgccatcgag atcgtcgaac gcgccctcga ccagtacggc    540
gcccccgtct acgtacgcaa gcagatcgtc cacaaccggc atgtcgtcga ggacctcgcc    600
cgccgcggcg cggtcttcgt cgaggagctt gacgaggtgc cggagggcga gctggtcgtc    660
ttctccgccc acggggtcgc cccggcggta cgtgacgcgg cgggcgagcg cggtctgcga    720
gtgatcgacg cgacctgccc gctggtcacc aaggtccatg ccgaggccaa gcggttcgcg    780
ggccgcggcg acaccgtcgt cctgatcggg cacgccggtc acgaggaggt cgagggcacg    840
ctgggcgagg cgcccgaccg cacggtgctg gtgcagaacg cggcggaggc ggcgcgcctg    900
gaggtcgagg accccgaggc ggtctccttc ctcatgcaga ccacgctggc gatgtccgag    960
gccaccgagg tggcccaggc cctggccggc cgcttcccgt cgatcaaggc accgcagtcc   1020
gaggacatct gctacgcctc gaccaaccgg cagcgcgccg tcgaggagat cgccgggcgg   1080
gtcgatctgc tcctggtggt cggatcgccc aactcctcca actccgtacg cctgaaggaa   1140
ctcgcggagc ggatgggcac ccccgcccag ctggtggacg acgcctcgta cgtcggtctg   1200
gagcagctgc acggggcccg gcggatcggc ctgacggccg gcgcctcggc cccggacacc   1260
ctcgtccagg aaatcgtcgc caatctccgt gccctcggac ccgtcacggt caccgagcac   1320
caagtcgcga cggagaacgt caccttccag ctgcccaaag agctgaggag cgcccggaaa   1380
gaccgcgccc gcaaagactt ggagaagacc gttgacagct gttgatctcg gtaccaaacc   1440
aattattaaa gacgctgaaa agcgtctttt tttgtttcgg tcctacttac tcgcgtaggc   1500
taaagatgac atctttaaca taggatgtgc gcaaaaaaaa gggagaggag cgtatttaat   1560
gccgacgaca ccgctgcgtc gtcccacccg gcagctgatg ctcggcggca tgggcgtcgg   1620
cagccgccac cccgtctcgg tgcagtcgat gacgaccacg gtgacggccg atgcccaggc   1680
caccccttcag cagatagccg aactcaccgc ggcgggctgc gacatcgtcc gggtcgcctg   1740
ccccagccgg gacgacgccg aagccctcgc ggagatcgcc cagaagtcga agatccccgt   1800
catcgcggac atccacttcc agccgcgcta tgtcttcgcc gcgatcgagg cgggctgcgc   1860
cggtgtccgg gtcaacccgg gcaacatcaa ggaattcgac gacaagatca aggagatcgc   1920
gcaggccgcg aaggaggccg gcaccccgat ccgcatcggg gtcaacgcgg gctcgctcga   1980
cccgaggatc ctgcggaagt tcggcaaggc gaccccggag gccctggccg aatcggcgct   2040
gcgcgaggcg gagctcttcg cggagcacga cttccacgac ttcaagatct cggtgaagca   2100
ccacgacccg atggtgatga tccgggcgta cgagctgctg gccgcgcagt gcgactaccc   2160
gctccacctc ggcgtcaccg aggcgggacc ggccttccag ggcacggtca agtcctcggt   2220
ggccttcggc gcgctgctgc gccagggcat cggcgacacc atccgcgtct cgctgtccgc   2280
accgcccgtg gaggaggtca aggtcggcat ccagatcctc cagtcgctcg gcctgcgccc   2340
ccggcgcctg gagatcgtct cctgcccgtc ctgcggccgc gcccaggtgg acgtctacaa   2400
gctcgccgaa gaggtgagcg ccgggctcga agggcttccg gtgccgctgc gggtcgccgt   2460
catgggctgt gtcgtcaacg gtcccggcga ggcccgcgag gccgacctcg gtgtcgcctc   2520
cggcaacggc aaggggcaga tcttcgtcaa gggcgaggtc gtcaagaccg tccccgagtc   2580
gaagatcgtc gagaccctca tcgaagaggc actgcgcctc gcggacgaga tgggggtgga   2640
```

-continued

```
cctcgatgag actggctgat ctcggtacca aattccagaa aagagacgct gaaaagcgtc   2700
tttttcgtt ttggtccagg ttcaaatggc taggatataa cctacacgat taggatagcc   2760
ccgcatcaat cagagaagga ggtaccaaaa tgagactggc tgacctcacc ggtccgggcg   2820
atctcgccgc actgacggag gatcaactcc aggcgctggc cgcggacatc cgctcctttc   2880
tcgtggagtc cgtttcgaag gtcggcggac acctgggccc caacctcggc gtcgtcgagc   2940
tcaccctcgc cctgcaccgg gtcttcgagt cccccaagga caccctgctc ttcgacaccg   3000
gccaccaggc ctacgtccac aagctgctca ccggccggat gaaggccttc tcgacgctgc   3060
gccaggaagg cgggctctcc ggctatcccg accgcagcga gtccgagcac gatgtcatcg   3120
agaactccca tgcctccacg gccctttcgt acgcagacgg catcgccaag ggcttcggcc   3180
tggccggcgc cgcgcaccgc agggtggtcg ccgtcgtcgg cgacggcgcg ctgaccggcg   3240
ggatgagctg ggaggcgctc aacaacatcg gcggcgcccc ggaccgcccg gtgatcatcg   3300
tcctgaacga caacggccgt tcctacgccc ccaccgccgg cgccctcgcc acccacctcg   3360
gcgagctccg ggcgggccgc ggcggggccg gtctcttcgc gaacctgggc ctcgcctacc   3420
tgggcccggt cgacggccac gaccgcccgg cactcgagcg cgcactgcgc cgggcggccg   3480
cactcgaccg ccccgtggtg gtgcactgtg tgacgcagaa gggccacggt tacgcaccgg   3540
ccgccgagga ccccgacgac tgctggcacg cggtgggcac cttcgacccc gagaccggcg   3600
gcaagtccgc ttccggcggc cgctcctgga ccgcggtgtt cggtgcggag atgacggaac   3660
tcggtgcgca gcggcccgac gtggtcgccc tcaccgccgc gatgctccag cccgtgggcc   3720
tggccgactt cgcccgccgc ttccccgacc gggtcttcga cgtcggcatc ggcgaacagc   3780
atgccgccgt ctccgccgcc gggctggcgc acaccgggct gcaccccgtc gtggccgtct   3840
actccacctt cctcaaccgc gccttcgacc aggtgctgat ggatgtggcg ctgcaccggc   3900
agccggtgac cttcgtactc gaccgggcgg gtgtcaccgg ccccgatggc cccagccatc   3960
acgggatctg ggacgcctcc tggctgtcgc tggtaccggg gctgcgcctg gcggtgccgc   4020
gcgatgccga ggaactcagg acgctgctgc gggaggcggt cgccgtcacg gacgggccca   4080
ccgtcctccg cttcccgaag gcacaggccg gcccggccgt gccggcgctc cgccgggagg   4140
ggggcatgga cgtgctgcac gaggcgcccg gcgcccgggt gctgctggtc ccgaccggtc   4200
cgctcgccga cccgtgcctt caggccgcgg ccgcgctgga cgccctgggc atcccgtcga   4260
cggtggtgga cccgcgctgg tccgtccccg taccggaggg gctgccggag ctggccgcac   4320
ggcacgaact cgtggtgacc gtcgaggaca acctgagcga cggcgggctc ggcgcgcgcc   4380
tgctgcgaca gctgtccgag gccggcacgc ccaccccgt acggaccgtc ggcctgccga   4440
cggagttcct tccccacggc agcaggacgg ccctcctgcg ccggcatggg ctcaccgccg   4500
acggcctggt cgcacgggtc ggcggatggc tgccacaagc ggcccccgc tgactcggta   4560
ccaaaccaat tattaaagac gctgaaaagc gtcttttttt gtttcggtcc gcttcaggtc   4620
ggctggttgg ctgacaaagt gcgtaggatg actgtgcatc aatcagagaa ggaggtacca   4680
aatgacgtcg gaactgcccg ccgcacgcgg cgaagggctg cggagcctcg tccgcatcca   4740
ccggctggaa taccccttc cggtcatcta tctctgccat gtcctgtggg gcgcctgcct   4800
cgcggcgacg ggtccgggca gcctggccgc cgcgcccgtc ctgatcatgc tgttcgccaa   4860
tatcgtcgcg atcatctccc agaacccgct caacgccggt ctggacatcc gggcggacac   4920
ccacaccagc ggcaaggaga gcatcgcccg cgccacccag cacctcagcg tccgcaccgc   4980
gttcacctgc gcggcactgg agatggcgct cgccctcggg ctgtccgtct gggtcgcgct   5040
```

-continued ctggctcggc cggccgctcg tcgcggtggg ggtggcgctg tcgatcgtgc tccacctcgc 5100
ctacaacctg gagccggtcc ggctgaagcg gcgcggctac gccaaccccg cctacttcgg 5160
ggcgaccttc gccttcctgc cgtcgctgtc gacgtatgcg gcggtgcggg cggacgtacc 5220
gctcagcgcg tggctgttcc tcaccgggct cggcatcctg ctgttcggcc gctccctgtg 5280
gtggtgcatc ccggacctga tcggtgacgc caaggccggg gaccgtacgc ccgccgtaca 5340
gcacggcccg cgccatgcgc tggtggtggc gtgcctgtgg accgcgctcg ggctgctgtt 5400
catcggcgcc gggctgtggc cgtacggcgt cctctgggcg ctgctcggca tcctggcgag 5460
cgccgccttc ctcgtggaca agatcaagct gctgcggcac atctcgcggg agaacctccc 5520
gcacgagtcc acgatgcgca agcacagcct ctcgctggcg atgggcggcg acctcctgct 5580
ctgcgccatc ccgctgctcg cgctctgatc agataaaaaa aatccttagc tttcgctaag 5640
gatgatttct cgctacccgt ggctactcag cgaataactc ttgtaggata cataaaaaaa 5700
aaagggagag gagcgtattt aatgctcgaa gttcccgctc agcccacgcc cgcccccccgc 5760
gaggccgagg cggccgcgct gctcgcggcg accgtccacg acccctgggg cctggtcgct 5820
ccgtcggtgt acgacaccgc ccggctggtc tccctcgccc cgtggctcga cggccaccgg 5880
gagcgtctcg gctatctggt cgaggagcag aaccaggacg gaagctgggg cgcacccgac 5940
gggtacggcc tggtacccac gctcagtgcg gtggaggcgc tgctgaccga actcgcccgg 6000
ccggaatccg gcgcgccgca cccgccccac gacgacctcg ccgcggcctg cgccggcggt 6060
ctgggcgccc tccaggacgg tctgctcgcc ggtccggtgc ccgacaccat cggcgtcgag 6120
ttcgtcgcgc cgtccctgct cgcggacatc aacacccggc tggccgcgct gaccgagcag 6180
gcacccggca agctcggggc atggtccggc accaccctga cgtcaccggc gcccgacctg 6240
gacggtgcgc tgctggccgg cgtccgggag atgaccgagc aggcgccgct gccggagaag 6300
ctgtggcaca cactggaggc catcacccgc gacggcaccc gcggtgcccg gccgcacgag 6360
ggcgcaccgc cgcacaacgg ctcggtcggc tgctccccccg ccgccaccgc cgcctggctg 6420
ggcgcctcgc ccgatccggc cgcgccgggc gtcgcctatc tccgtgacgt ccaggcgcgg 6480
ttcggcgggc cggtgccctc gatcaccccg atcgtctact tcgagcaggc gtgggtcctc 6540
aactcgctgg ccgcctccgg cctgcgctac gaggccccgg ccgcgctcct cgacagcctc 6600
gaagcgggtc tcacggacga gggcacagcc gccgccccccg gtctgccgag cgactccgac 6660
gacaccgccg ccgtcctctt cgccctggcg cagcacggca ggacgcaccg ccccgacagc 6720
ctgatgcact tccgccggga cggctacttc tcctgcttcg gcgtcgagcg cacccccctcc 6780
accagcacca acgcacacat cctggaggcc ctcggccatc acgtcacggt gcgccccgac 6840
gacgcgggac gctatggcgc ggagatccgg atgatcagcg actggctgct ggacaaccag 6900
ctgcccgacg gcagctggat ggacaagtgg cacgcctcgc cgtactacgc cacggcctgc 6960
tgtgcgctgg cgctcgccga gttcggcggc ccgtccgcac gggccgcggt cggccgggcc 7020
gccgcgtggg cactggcgac ccagcgcgcc gacggctcct ggggacgctg gcagggcacc 7080
acggaggaga ccgcgtacat ggtgcagctc ctgatgcgta cccgtacccc cgggagcccg 7140
gggaccgtcg cccggtcggc ggcccgcggc tgcgacgcgc tgctggccca cgacgacccg 7200
gcctcctacc ccgggctctg gcacgacaag gacatctacg cgccggtgac cgtcatccgg 7260
gcggcgcggc tcgcggcact ggcgctcggc ggcgccgagt ccgccgcttc cggaggtgct 7320
tgattccggc aattaaaaaa gcggctaacc acgccgcttt ttttacgtct gcaggagtag 7380

-continued

```
cagggctcca aaactaacgc ctgatgtagg atcagatggc tacaaggaag aaggaggtta   7440
acaatgcacg ctgacacagt ccagcccctc gagagcagtg tcgacctggc ccaccgcaac   7500
gcctcgcggg ccgccggcct cgtcacgccc gccctgcggg ccaccgtcga caccttcgac   7560
aaccgcatcc gccccatcgt cgcctaccac ttcggctgga tggacaccag cggacgcccc   7620
acggcgaaca gcggcggcaa gatgatccgg gcggcactga ccatccttgc cgccgaggcc   7680
tgcggcggcg acgcccagca ggccgtaccc ggcgccgccg ccgtcgaact ggtccacaac   7740
ttctcgctgt tgcacgacga cgtcatggac cgcgatctgg agcggcgcgg ccggcccacg   7800
gtatggagca agttcggcac ccccgcggcg atcctggcgg gcgacatcct gctggcgcgc   7860
gcctgcggca tgttcgacga ggcctccggc caccagggct gggcgaccaa ggccctgatc   7920
gacgcgatcg ccgagctggc cgcgggccag atggccgacc tcgcgctgga gcgccgcgcc   7980
acggtgaccc tggaagaggc cctcaccgtc tccgagcaga agaccgcggc gctgctgcgc   8040
tgcgcctgca cgctgggcgc gggactcgtc ggcgcacccg acgggaccag ccgccgcttc   8100
ggcgccttcg gtatgcacct gggcatggcg ttccagctgg tcgacgacgt actcggcata   8160
tggggcgacc cggccgtcac cggcaagccg gtccgctccg acctgcacaa caagaagaag   8220
agcattcccg tcgtcgccgc cctccacagc ggccggcccg gctccgcgga actggccgcg   8280
ctctacgcgg acaccgaccc catgacggag gacggcgccc ggcgcgccgc cgagctggtc   8340
gagctggccg gcggccgcgc ctggaccgag agcgagatcg agcggcaccg cggcctcgcc   8400
gtggcgcagc tcgacgccct cgggctgacg gaggcgcagc gggcacccct gctcgccctc   8460
gccgactacg tcgccttcag gaagcactga tgtcagtttc acctgtttta cgtaaaaacc   8520
cgcttcggcg ggtttttact tttggtactc gcgtaggcta aagatgacat ctttaacata   8580
ggatgtgcgc aaaaaaaagg gagaggagcg tatttaatga ccacccgccc cacggccgcc   8640
tcgcgcggca acaagtaccg cttcgccttc cgcaccctct ccttcctgga cgcccacaag   8700
aacgaccgct ccggtgtggc cgagctcagc gggccgcccg gccgggcgct cctggtgtgg   8760
aagccggaga tcatcagcca ggtcttccgc ggcgaccgga acatgacgct ggagggctcc   8820
gacacgctcg gcccgctggt cggcgacacc tcgctgctgt tcgccaacgg gccgcggcac   8880
gccgcgtacc gccaggtgat cggcccgcgg ctgcgcggcc gtccgctgcg cggctacgag   8940
gagctgatcg ccgaggccac ccgggcggcg atcgacgaac tgcggccggg caccgacttc   9000
caggtgcccg actggacccg caggctcacc cttcagatcg tcagccagat catcctcggc   9060
ccggtggacc acggtctgct gcaccgcttc acctcctgga tcgagggggt gctgggctcg   9120
cgcggccgca ccctcgccta ccgctatctg cggctgccgc acgccctgcc gtctccctgg   9180
cgcacctttg tgcggcagcg cgagagcctg gacaaggagc tgctgtgccc ggtgagcggc   9240
aagagcgccg gcggcggtgc gggttccggt gcgccggagc cgtcgccggc cacgctcgcc   9300
gaggtgctgc gcagcggtga ggagccgctc ggcccgctgg gcgacggcga actgcgtgac   9360
cagatcgtct cgttgctgtt cgcgggccac gagacgaccg cctcggcgat ctcctgggcg   9420
ctgttctggc tcgcggagca cgacgaggtg cgccgcgaca tcatcgacga gctgaaggcc   9480
acctcctcca gcggtgcggc ggcggaggac gtaccgctgc tggacgcggc ctgccgggag   9540
gtgctgcgga tctcgccgcc cgccgtggtg gccggcaacc gtgtgctcaa cgagggccag   9600
gagatcgacg ggtaccgcca cgacgcgggc acccggctga cgccgtgcat ctacctggcg   9660
caccagcagc cggatctcta cccgcagccg gagcgcttcg acccgcaccg cttcctgggc   9720
aagcgcaagt ccgcccagga gtacctgccg ttcggcggcg gcacccgccg ctgtctcggt   9780
```

gccgacctcg cgatgctgga gatgcggatg gtggtggcgg cggtgctgcg ccggcgagaa 9840
ctgaagtgcg tcaatccgga gaccggggta ccgcagctgc gcggtccggc gatgggtccg 9900
agcgaagacc tgagaatgac ggtgaccgag tgtccagcat gatctcggta ccaaattcca 9960
gaaaagagac gctgaaaagc gtcttttttc gttttggtcc aagttcaaat ggctaggata 10020
taacctacac gattaggata gccccgcatc aatcagagaa ggaggtacca aaatgtggga 10080
gccgacgtct gcggggtggg gtgcgcgggt cgaggggtgg gatctggggg cgccgttggg 10140
tgcggagtgt gcggcggcgt tggtggagtt gttccgtgcg cggcatctgc tggtgttttc 10200
gggtcagggt ttctcgttgg aggagcagat ccggttcatg gggcatttgg gtccggtgct 10260
gcatgaggag ggttcgggga tcgggtttgt ttcgaatgtg aaggaggggg ctgctctggg 10320
ggtgagtgag ctgtctttcc attcggatac ggggcattgt gcggtgccgt tggaggcggt 10380
gtcgcttttt gctgaggatg ttgaggggtg tgtgacgtcg acgcggtttg cgaatgtggc 10440
ggcggcgtat gggcgtttgc cggcgggttt gcggtcgcgg gttgcgggac tggtgtgtga 10500
gaacgcgatg ccggtgtcgt tggacggccg gaatgtgggg ttgtcggtgg cggaggggat 10560
gccgcgggcg gagcatccgg tggtgtggcg tcatccggtg tcgggggagc cggggctgat 10620
ggtgaatgcg aatcagacga cgcggatcgt gggccttgag ggtgaagaga gccgggggtt 10680
gctggaggag ttgttctcgg tgatgtatgc cgaggatgcg gtgtatgagc attcctggca 10740
gcagggggat gtggtgatct ggcacaacct ggcggttcag catgcgcggg gtggcctgga 10800
aggtaatggc cggcggactc tgcgccgggt ggcgttgggt gagaaggggt tttgggagca 10860
gtgcccgacc ctgcgttacg ccgatttcaa aaaccagcag aacaccgccg cgtgataaaa 10920
aaaaaaaaca ccctaacggg tgtttttttt tttttggtct cccgcttccc gtcggctgga 10980
aacacttgat ccaacttagg atacttccta attcatttta ctacaattac gcgtttacgt 11040
cagaatgacg tacgtaatcg cgcagccctg tgtcgacctc aaggacaagg cgtgcatcga 11100
ggagtgcccg gtcgactgca tctacgaggg caagcggtcc ttgtacatcc acccggacga 11160
atgcgtcgac tgcggtgcct gtgagccggt ctgcccggtc gaggccatct tctacgagga 11220
cgacacaccg gaggagtgga aggactacta caaggcgaat gtggagttct tcgacgagct 11280
cggctcgccg ggcggcgccg cccggctcgg cctgatcgac cgcgaccacc ccgtcgtcgc 11340
ggcgcagccg gtccgtacgg ccggagccgc gggcgaatga tctcggtacc aaaaaaaaaa 11400
aaaaagacgc tgaaaagcgt cttttttttt tttggtcccg ct 11442

<210> SEQ ID NO 30
<211> LENGTH: 21610
<212> TYPE: DNA
<213> ORGANISM: artificial
<220> FEATURE:
<223> OTHER INFORMATION: PB20 gene cluster

<400> SEQUENCE: 30
ggagtcaaat ggctaggata taacctacac gattaggata gccccatcca ccaatacgca 60
cagaaggaga ttataaatga ccgccgccat cgtgagtgtc gccgcccgcc cgctgagcac 120
ggcggtgcgc cacggcgacg tggtgctcgc cgaccggctg cacctggcgt cgggcgcccg 180
cgagggccgg gtccaccggc tgctcgccgg ggccctcagg gcacaggggc tgacggtcca 240
caccggcggg gccgccgtcg ccggcgccga ggcaccccag ggcgccgacg caccgctggt 300
ggagatcgcc gcgccggtcc ggctcccgga ggcggacggt gacgcgctgc tgtgcctggt 360

-continued

```
gcgcgacgac accggatcgg acgccgtcga ccgcgccgag gaggccctgg cccgggtcct    420
gggcgactgg gaagccgcga agggggaccg agcggtggcc ctggccgccc cccggtcgtt    480
ctgcgccggt gtggaccgtg ccatcgagat cgtcgaacgc gccctcgacc agtacggcgc    540
ccccgtctac gtacgcaagc agatcgtcca caaccggcat gtcgtcgagg acctcgcccg    600
ccgcggcgcg gtcttcgtcg aggagcttga cgaggtgccg gagggcgagc tggtcgtctt    660
ctccgcccac ggggtcgccc cggcggtacg tgacgcggcg ggcgagcgcg gtctgcgagt    720
gatcgacgcg acctgcccgc tggtcaccaa ggtccatgcc gaggccaagc ggttcgcggg    780
ccgcggcgac accgtcgtcc tgatcgggca cgccggtcac gaggaggtcg agggcacgct    840
gggcgaggcg cccgaccgca cggtgctggt gcagaacgcg gcggaggcgg cgcgcctgga    900
ggtcgaggac cccgaggcgg tctccttcct catgcagacc acgctggcga tgtccgaggc    960
caccgaggtg gcccaggccc tggccggccg cttcccgtcg atcaaggcac cgcagtccga   1020
ggacatctgc tacgcctcga ccaaccggca gcgcgccgtc gaggagatcg ccgggcgggt   1080
cgatctgctc ctggtggtcg gatcgcccaa ctcctccaac tccgtacgcc tgaaggaact   1140
cgcggagcgg atgggcaccc ccgcccagct ggtggacgac gcctcgtacg tcggtctgga   1200
gcagctgcac ggggcccggc ggatcggcct gacggccggc gcctcggccc cggacaccct   1260
cgtccaggaa atcgtcgcca atctccgtgc cctcggaccc gtcacggtca ccgagcacca   1320
agtcgcgacg gagaacgtca ccttccagct gcccaaagag ctgaggagcg cccggaaaga   1380
ccgcgcccgc aaagacttgg agaagaccgt tgacagctgt tgattagcat aaccccttgg   1440
ggcctctaaa cgggtcttga ggggtttttt gttactctta gaggctggtg tcaactagat   1500
caccatagga ttcaccacga agatagaagg aggttataaa atgccgacga caccgctgcg   1560
tcgtcccacc cggcagctga tgctcggcgg catgggcgtc ggcagccgcc accccgtctc   1620
ggtgcagtcg atgacgacca cggtgacggc cgatgcccag gccaccccttc agcagatagc   1680
cgaactcacc gcggcgggct gcgacatcgt ccgggtcgcc tgccccagcc gggacgacgc   1740
cgaagccctc gcggagatcg cccagaagtc gaagatcccc gtcatcgcgg acatccactt   1800
ccagccgcgc tatgtcttcg ccgcgatcga ggcgggctgc gccggtgtcc gggtcaaccc   1860
gggcaacatc aaggaattcg acgacaagat caaggagatc gcgcaggccg cgaaggaggc   1920
cggcaccccg atccgcatcg gggtcaacgc gggctcgctc gacccgagga tcctgcggaa   1980
gttcggcaag gcgaccccgg aggccctggc cgaatcggcg ctgcgcgagg cggagctgtt   2040
cgcggagcac gacttccacg acttcaagat ctcggtgaag caccacgacc cgatggtgat   2100
gatccgggcg tacgagctgc tggccgcgca gtgcgactac ccgctccacc tcggcgtcac   2160
cgaggcggga ccggccttcc agggcacggt caagtcctcg gtggccttcg gcgcgctgct   2220
gcgccagggc atcggcgaca ccatccgcgt ctcgctgtcc gcaccgcccg tggaggaggt   2280
caaggtcggc atccagatcc tccagtcgct cggcctgcgc ccccggcgcc tggagatcgt   2340
ctcctgcccg tcctgcggcc gcgcccaggt ggacgtctac aagctcgccg aagaggtgag   2400
cgccgggctc gaagggcttc cggtgccgct gcgggtcgcc gtcatgggct gtgtcgtcaa   2460
cggtcccggc gaggcccgcg aggccgacct cggtgtcgcc tccggcaacg gcaaggggca   2520
gatcttcgtc aagggcgagg tcgtcaagac cgtccccgag tcgaagatcg tcgagaccct   2580
catcgaagag gcactgcgcc tcgcggacga gatgggggtg gacctcgatg agactggctg   2640
atctcggtac caaattccag aaaagagacg ctgaaaagcg tctttttttcg ttttggtcca   2700
ggttgtgcgg gctctaacac gtcctagtat ggtaggatga gcaagctaca aggaagaagg   2760
```

-continued

```
aggttaacaa atgagactgg ctgacctcac cggtccgggc gatctcgccg cactgacgga   2820

ggatcaactc caggcgctgg ccgcggacat ccgctccttt ctcgtggagt ccgtttcgaa   2880

ggtcggcgga cacctgggcc ccaacctcgg cgtcgtcgag ctcaccctcg ccctgcaccg   2940

ggtcttcgag tcccccaagg acaccctgct gttcgacacc ggccaccagg cctacgtcca   3000

caagctgctc accggccgga tgaaggcctt ctcgacgctg cgccaggaag gcgggctctc   3060

cggctatccc gaccgcagcg agtccgagca cgatgtcatc gagaactccc atgcctccac   3120

ggccctttcg tacgcagacg gcatcgccaa gggcttcggc ctggccggcg ccgcgcaccg   3180

cagggtggtc gccgtcgtcg gcgacggcgc gctgaccggc gggatgagct gggaggcgct   3240

caacaacatc ggcggcgccc cggaccgccc ggtgatcatc gtcctgaacg acaacggccg   3300

ttcctacgcc cccaccgccg gcgccctcgc cacccacctc ggcgagctcc gggcgggccg   3360

cggcggggcc ggtctcttcg cgaacctggg cctcgcctac ctgggcccgg tcgacggcca   3420

cgaccgcccg gcactcgagc gcgcactgcg ccgggcggcc gcactcgacc gccccgtggt   3480

ggtgcactgt gtgacgcaga agggccacgg ttacgcaccg gccgccgagg accccgacga   3540

ctgctggcac gcggtgggca ccttcgaccc cgagaccggc ggcaagtccg cttccggcgg   3600

ccgctcctgg accgcggtgt tcggtgcgga gatgacggaa ctcggtgcgc agcggcccga   3660

cgtggtcgcc ctcaccgccg cgatgctcca gcccgtgggc ctggccgact tcgcccgccg   3720

cttccccgac cgggtcttcg acgtcggcat cggcgaacag catgccgccg tctccgccgc   3780

cgggctggcg cacaccgggc tgcaccccgt cgtggccgtc tactccacct tcctcaaccg   3840

cgccttcgac caggtgctga tggatgtggc gctgcaccgg cagccggtga ccttcgtact   3900

cgaccgggcg ggtgtcaccg gccccgatgg ccccagccat cacgggatct gggacgcctc   3960

ctggctgtcg ctggtaccgg ggctgcgcct ggcggtgccg cgcgatgccg aggaactcag   4020

gacgctgctg cgggaggcgg tcgccgtcac ggacgggccc accgtcctcc gcttcccgaa   4080

ggcacaggcc ggcccggccg tgccggcgct ccgccgggag gggggcatgg acgtgctgca   4140

cgaggcgccc ggcgcccggg tgctgctggt cccgaccggt ccgctcgccg acccgtgcct   4200

tcaggccgcg gccgcgctgg acgccctggg catcccgtcg acggtggtgg acccgcgctg   4260

gtccgtcccc gtaccggagg ggctgccgga gctggccgca cggcacgaac tcgtggtgac   4320

cgtcgaggac aacctgagcg acggcgggct cggcgcgcgc ctgctgcgac agctgtccga   4380

ggccggcacg cccacccccg tacggaccgt cggcctgccg acggagttcc ttccccacgg   4440

cagcaggacg gccctcctgc gccggcatgg gctcaccgcc gacggcctgg tcgcacgggt   4500

cggcggatgg ctgccacaag cggccccccg ctgataaaaa aaaaaaacac cctaacgggt   4560

gttttttttt ttttggtctc ccgcttcagg tcggctggtt ggctgacaaa gtgcgtagga   4620

tgactgtgca tcaatcagag aaggaggtac caaaatgacg gactccctcg cccacccgca   4680

tacgcgtttc gagccggcct ccggcgaccc tgacggcccg cgcggccccc gttccctcgt   4740

ggtgctcggc tcgaccggct cgatcggcac ccaggcgatc gacatcgtgc tgcgcaatcc   4800

cgaccgcttc cgggtgaccg cgctctccgc ggccggcggc cgggtcgagc tgctcgccga   4860

tcaggcgcac cagctgcggg tggccgccgt cgccgtggcg cgcgaggacg cggtgcccgc   4920

gctgcgtacg gcactggccg accgctacgg cgcgggcgag ccgctgcccg agatcctggc   4980

cggccccgac gcggccaccg agctggccgc ctccccctgc cacaccgtcc tcaacggcat   5040

caccggctcc atcggcctcg ccccgaccct ggccgccctg aaggcgggcc gggtgctggc   5100
```

-continued

```
cctcgccaac aaggagtcgc tgatcgtcgg cggcccgctg gtcaaggccc tcgccgagcc   5160
cggccagatc atccccgtcg actccgagca ctccgcgctc ttccaggcgc tggccggcgg   5220
cgagcgcgcc gaggtccgca agctcgtcgt caccgcttcc ggcggtccgt tccgcggccg   5280
tacgaagaag gagctggccg gggtcacgcc cgagcaggcg ctggcccacc ccacctggtc   5340
gatgggcccg gtcgtcacca tcaactcggc gaccctcgtc aacaagggcc tggaggtcat   5400
cgaggcgcat ctgctcttcg acgtgccctt cgaccgcatc gaggtcgtcg tccacccgca   5460
gtcctacatc cactcgatgg tggagttcac cgacggctcc acgctcgccc aggccagccc   5520
gcccgacatg cggatgccga tcgcgctggg catcggctgg cccgagcggg tcccggacgc   5580
cgcaccgggc gtggactgga cgaaggcgca gacctgggag ttcttcccgc tggacgagga   5640
ggccttcccg tccgtcccgc tggcccgcca cgtcggtgat ctgggcggca ccgcccccgc   5700
cgtcttcaac gcggcgaacg aggaatgcgt ggacgcgttc ctcaagggcg ggctgccctt   5760
cacagggatt gtggataccg tcgccgcagt ggtcgccgaa cacggaacgc ccgccggggg   5820
aacttccctg agtgtcgcgg acgtcctcga ggcggagacc tggcgcgcg cccgcgcccg   5880
cgaactggcc gcccgtgcgg cacggacacc ttcggaggct cgcgcatgat cagataaaaa   5940
aaatccttag ctttcgctaa ggatgatttc tgcgttgttc acattcgaac cgtctctgct   6000
ttgacaacat gctgtgcggt gttgtaaagt ctggtgtatc taagtaagga gacatctaat   6060
gtcagatcct tcccgcccgg tccgcaccgc cgcggtgatc ccgccgccg gccgcggtgt   6120
ccggctcggt cccggcaccc ccaaggcgct gcgcacgctg ggcggcaccc ccatgctggt   6180
gcacgccgtc cgcgcgatgg ccgcctcgcg cgcggtctcc ctcatcgtgg tggtggcccc   6240
gcccgacggc gccgccgagg tcagccgcct gctccacgag cacccgctcg ccgaacgcac   6300
cgagctcgag gtcgtccccg gcggcgaaac ccgccaggag tccgtacagc tcggtctggc   6360
ggcgctcccg gacaccatcg acgtcgtgct ggtgcatgac gccgcgcgcc cgctggtccc   6420
ggtcgacacg gtcgacacgg tggtcgcggc cgtacgcgcc ggtgcgccgg ccgtcgtccc   6480
ggcgctgccg ctcgccgaca ccgtcaagca ggtcgacccg cagccgcagg gcaccccgga   6540
gccggtggtc ggcaccccgg agcggtccct gctgcgcgcc gtgcagaccc cgcagggctt   6600
cgacctggcg accctgcgca aggcgcatga caccgtcgtc gagggcgagg gcgccaccga   6660
tgacgccggg ctggtcgaac ggctcggttc gccggtcgtg gtcgtcccgg gccacgagga   6720
agcgttcaag gtgacccggc cgctggacct ggtcctggcc gaggccgtac tcgcccgcag   6780
gagggccacc gatggctatg tctgattccg gcaattaaaa aagcggctaa ccacgccgct   6840
ttttttacgt ctgcaggagt gttcacattc gaaccgtctc tgctttgaca acatgctgtg   6900
cggtgttgta aagtctggtg tatctaagta aggagacatc taatgacgtt caccacctcg   6960
atcaccgtcc gggtaccggc caaggtcaac gtccagctgg ccgtcggcgc cgcccgcccg   7020
gacggcttcc acgacctggc caacgtcttc ctcgccgtcg gcctctacga cgaggtcacc   7080
gcgacccccg ccgagtccct gcggatcacc gccgagggcc acgacgtcga ccagatcccg   7140
ctggaccgga cgaacctggc cgcccgcgca gccgaactgc tcgccgcccg gcacggcatc   7200
gagccgcacg tccacctcca catcaccaag gacatccccg tcgccggcgg catggcgggc   7260
ggcagcgcgg acgccgccgg ggccctgctg gcctgcgacg ccctgtggtc gacgggtgcc   7320
tcgcgcgagg aactcctttc cctctgcgcc gagttgggca gcgatgtgcc gttcagcctg   7380
gtgggtggcg cggccctggg acgcggccgt ggcgaactcc tgaccccct ccccgtcggc   7440
ggcgccttcc actgggtctt cgcggtcgcc gacggcgggc tgtccacccc ggccgtctac   7500
```

ggcgagttcg accggctgac ggcgggcacc gaggtgcccg agcccgaggc ggacccagcc 7560
ctgctggccg ccctggagac cggcgacgcc accgcgctcg ccgcggccct caccaacgac 7620
ctccagcccg cggccctgtc cctgcgcccg tccctgaccg cgacgctgga ggccggcacc 7680
gccgccggcg ccctggccgc gctggtctcc ggctccgggc cgaccaccgc cttcctggcc 7740
aaggacgcgg aggcggcaaa ggaagtggca tcggcgctgc tggcgtcggg gacctgccgt 7800
caggtgcggg tggcggattc tccggcggtg ggggcgaggg ttctttgatg tcagtttcac 7860
ctgttttacg taaaaacccg cttcggcggg tttttacttt tggtactcag gtcggctggt 7920
tggctgacaa agtgcgtagg atgactgtat cggattaaga aggaggtaca gtaatgtctg 7980
acccgacccc ttccggcgcg ctccccggcg cccctctcgt ccccctcgtc ggcatcggca 8040
cggatgtgca cgccttcgag cagggccggg agctgtggtg cgcgggtctg ctctgggaca 8100
ccacggagag cgacggctac ggcctggccg gtcacagcga cggcgatgtg gccgcgcatg 8160
ccgcctgtga cgcactgttc tcggcggccg gcgtcggcga cctgggtgcc cacttcggca 8220
ccagccgccc cgagtggtcc ggcgcctccg gagtgaccct gctggccgag gccgcccgga 8280
tcgtacgggc cgagggcttc accatcggca atgtcgcggt gcaggtcatc ggcgtacgcc 8340
cgaaggtcgg caagcggcgg gacgaggccc aaaaggcgct gtcggcggcc gtcggcgcgc 8400
cggtctcggt ctccgggacg acctcggacg ggctgggcct gacgggccgc gccgagggcc 8460
tggccgcggt ggccacggcg atcgtcttcc gtacggcctg atgacgaaca ataaggcctc 8520
cctaacgggg ggcctttttt attgataaca aaaaggttag cagggctcca aaactaacgc 8580
ctgatgtagg atcagatgcg aagatagaag gaggttataa aatgccgatc acaccggcca 8640
acggacagac cgccggcgac ccggcggtga gcacaccggg cggcaccgcc gaaccgatca 8700
tgctggagct ggtcgacgag gacggtacga cgatcggcac cgcggagaag ctcgcggccc 8760
accagcctcc cgggcagctg caccgggcgt tctccgtctt cctcttcgac gagaaggggc 8820
ggctgctgct ccagcgccgg gcactgggga agtaccactc ccccggtgtg tggtccaaca 8880
cgtgctgcgg ccacccgtat cccggcgagg cgccgttcgt ggccgcggcc cggcgcacct 8940
ccgaggagct gggcctggca cccgccctgc tggccgaggc gggcaccgtg cgttacaacc 9000
atcccgaccc ggcctccggc cttgtggagc aggagtacaa ccacctgttc gtcgggctgg 9060
tgcgggccga gccggcgccc gatcccgagg agatcggcga gatcgcgttc gtgacgccgc 9120
aggagctggc cgagcggcat gccgaggcgc cgttctccgc gtggttcatg accgtcctgg 9180
acgcggcgcg tccggcggtg cgcgagctca caggactgtc ggcgggctgg tgatctcggt 9240
accaaaaaaa aaaaaaaaga cgctgaaaag cgtctttttt ttttttggtc cgcttcaggt 9300
cggctggttg gctgacaaag tgcgtaggat gactgtgcat caatcagaga aggaggtacc 9360
aaatgacgtc ggaactgccc gccgcacgcg gcgaagggct gcggagcctc gtccgcatcc 9420
accggctgga ataccccttt ccggtcatct atctctgcca tgtcctgtgg ggcgcctgcc 9480
tcgcggcgac gggtccgggc agcctggccg ccgcgcccgt cctgatcatg ctgttcgcca 9540
atatcgtcgc gatcatctcc cagaacccgc tcaacgccgg tctggacatc cgggcggaca 9600
cccacaccag cggcaaggag agcatcgccc gcgccaccca gcacctcagc gtccgcaccg 9660
cgttcacgtg cgcggcactg gagatggcgc tcgccctcgg gctgtccgtc tgggtcgcgc 9720
tctggctcgg ccggccgctc gtcgcggtgg gggtggcgct gtcgatcgtg ctccacctcg 9780
cctacaacct ggagccggtc cggctgaagc ggcgcggcta cgccaacccc gcctacttcg 9840

```
gggcgacctt cgccttcctg ccgtcgctgt cgacgtatgc ggcggtgcgg gcggacgtac   9900
cgctcagcgc gtggctgttc ctcaccgggc tcggcatcct gctgttcggc cgctccctgt   9960
ggtggtgcat cccggacctg atcggtgacg ccaaggccgg ggaccgtacg cccgccgtac  10020
agcacggccc gcgccatgcg ctggtggtgg cgtgcctgtg gaccgcgctc gggctgctgt  10080
tcatcggcgc cgggctgtgg ccgtacggcg tcctctgggc gctgctcggc atcctggcga  10140
gcgccgcctt cctcgtggac aagatcaagc tgctgcggca catctcgcgg gagaacctcc  10200
cgcacgagtc cacgatgcgc aagcacagcc tctcgctggc gatgggcggc gacctcctgc  10260
tctgcgccat cccgctgctc gcgctctgat cagataaaaa aaatccttag ctttcgctaa  10320
ggatgatttc tcgctacccg tggctactca gcgaataact cttgtaggat acataaaaaa  10380
aaaagggaga ggagcgtatt taatgctcga agttcccgct cagcccacgc ccgcccccg  10440
cgaggccgag gcggccgcgc tgctcgcggc gaccgtccac gacccctggg gcctggtcgc  10500
tccgtcggtg tacgacaccg cccggctggt ctccctcgcc ccgtggctcg acggccaccg  10560
ggagcgtctc ggctatctgg tcgaggagca gaaccaggac ggaagctggg gcgcacccga  10620
cgggtacggc ctggtaccca cgctcagtgc ggtggaggcg ctgctgaccg aactcgcccg  10680
gccggaatcc ggcgcgccgc acccgcccca cgacgacctc gccgcggcct gcgccggcgg  10740
tctgggcgcc ctccaggacg gtctgctcgc cggtccggtg cccgacacca tcggcgtcga  10800
gttcgtcgcg ccgtccctgc tcgcggacat caacacccgg ctggccgcgc tgaccgagca  10860
ggcacccggc aagctcgggg catggtccgg caccaccctg acgtcaccgg cgcccgacct  10920
ggacggtgcg ctgctggccg gcgtccggga gatgaccgag caggcgccgc tgccggagaa  10980
gctgtggcac acactggagg ccatcacccg cgacggcacc cgcggtgccc ggccgcacga  11040
gggcgcaccg ccgcacaacg gctcggtcgg ctgctccccc gccgccaccg ccgcctggct  11100
gggcgcctcg cccgatccgg ccgcgccggg cgtcgcctat ctccgtgacg tccaggcgcg  11160
gttcggcggg ccggtgccct cgatcacccc gatcgtctac ttcgagcagg cgtgggtcct  11220
caactcgctg gccgcctccg gcctgcgcta cgaggccccg gccgcgctcc tcgacagcct  11280
cgaagcgggt ctcacggacg agggcacagc cgccgccccc ggtctgccga gcgactccga  11340
cgacaccgcc gccgtcctct tcgccctggc gcagcacggc aggacgcacc gccccgacag  11400
cctgatgcac ttccgccggg acggctactt ctcctgcttc ggcgtcgagc gcaccccctc  11460
caccagcacc aacgcacaca tcctggaggc cctcggccat cacgtcacgg tgcgccccga  11520
cgacgcggga cgctatggcg cggagatccg gatgatcagc gactggctgc tggacaacca  11580
gctgcccgac ggcagctgga tggacaagtg gcacgcctcg ccgtactacg ccacggcctg  11640
ctgtgcgctg gcgctcgccg agttcggcgg cccgtccgca cgggccgcgg tcggccgggc  11700
cgccgcgtgg gcactggcga cccagcgcgc cgacggctcc tggggacgct ggcagggcac  11760
cacggaggag accgcgtaca tggtgcagct cctgatgcgt acccgtaccc ccgggagccc  11820
ggggaccgtc gcccggtcgg cggcccgcgg ctgcgacgcg ctgctggccc acgacgaccc  11880
ggcctcctac cccgggctct ggcacgacaa ggacatctac gcgccggtga ccgtcatccg  11940
ggcggcgcgg ctcgcggcac tggcgctcgg cggcgccgag tccgccgctt ccggaggtgc  12000
ttgatcagat aaaaaaaatc cttagctttc gctaaggatg atttctggag tagcagggct  12060
ccaaaactaa cgcctgatgt aggatcagat ggctacaagg aagaaggagg ttaacaatgc  12120
acgctgacac agtccagccc ctcgagagca gtgtcgacct ggcccaccgc aacgcctcgc  12180
gggccgccgg cctcgtcacg cccgccctgc gggccaccgt cgacaccttc gacaaccgca  12240
```

tccgccccat cgtcgcctac cacttcggct ggatggacac cagcggacgc cccacggcga 12300
acagcggcgg caagatgatc cgggcggcac tgaccatcct tgccgccgag gcctgcggcg 12360
gcgacgccca gcaggccgta cccggcgccg ccgccgtcga actggtccac aacttctcgc 12420
tgttgcacga cgacgtcatg gaccgcgatc tggagcggcg cggccggccc acggtatgga 12480
gcaagttcgg cacccccgcg gcgatcctgg cgggcgacat cctgctggcg cgcgcctgcg 12540
gcatgttcga cgaggcctcc ggccaccagg gctgggcgac caaggccctg atcgacgcga 12600
tcgccgagct ggccgcgggc cagatggccg acctcgcgct ggagcgccgc gccacggtga 12660
ccctggaaga ggccctcacc gtctccgagc agaagaccgc ggcgctgctg cgctgcgcct 12720
gcacgctggg cgcgggactc gtcggcgcac ccgacgggac cagccgccgc ttcggcgcct 12780
tcggtatgca cctgggcatg gcgttccagc tggtcgacga cgtactcggc atatggggcg 12840
acccggccgt caccggcaag ccggtccgct ccgacctgca caacaagaag aagagcattc 12900
ccgtcgtcgc cgccctccac agcggccggc ccggctccgc ggaactggcc gcgctctacg 12960
cggacaccga ccccatgacg gaggacggcg cccggcgcgc cgccgagctg gtcgagctgg 13020
ccggcggccg cgcctggacc gagagcgaga tcgagcggca ccgcggcctc gccgtggcgc 13080
agctcgacgc cctcgggctg acggaggcgc agcgggcacc cctgctcgcc ctcgccgact 13140
acgtcgcctt caggaagcac tgatgtcagt ttcacctgtt ttacgtaaaa acccgcttcg 13200
gcgggttttt acttttggta ctcgcgtagg ctaaagatga catctttaac ataggatgtg 13260
cgcaaaaaaa agggagagga gcgtatttaa tgaccacccg ccccacggcc gcctcgcgcg 13320
gcaacaagta ccgcttcgcc ttccgcaccc tctccttcct ggacgcccac aagaacgacc 13380
gctccggtgt ggccgagctc agcgggccgc ccggccgggc gctcctggtg tggaagccgg 13440
agatcatcag ccaggtcttc cgcggcgacc ggaacatgac gctggagggc tccgacacgc 13500
tcggcccgct ggtcggcgac acctcgctgc tgttcgccaa cgggccgcgg cacgccgcgt 13560
accgccaggt gatcggcccg cggctgcgcg gccgtccgct gcgcggctac gaggagctga 13620
tcgccgaggc cacccgggcg gcgatcgacg aactgcggcc gggcaccgac ttccaggtgc 13680
ccgactggac ccgcaggctc acccttcaga tcgtcagcca gatcatcctc ggcccggtgg 13740
accacggtct gctgcaccgc ttcacctcct ggatcgaggg ggtgctgggc tcgcgcggcc 13800
gcaccctcgc ctaccgctat ctgcggctgc cgcacgccct gccgtctccc tggcgcacct 13860
ttgtgcggca gcgcgagagc ctggacaagg agctgctgtg cccggtgagc ggcaagagcg 13920
ccggcggcgg tgcgggttcc ggtgcgccgg agccgtcgcc ggccacgctc gccgaggtgc 13980
tgcgcagcgg tgaggagccg ctcggcccgc tgggcgacgg cgaactgcgt gaccagatcg 14040
tctcgttgct gttcgcgggc cacgagacga ccgcctcggc gatctcctgg gcgctgttct 14100
ggctcgcgga gcacgacgag gtgcgccgcg acatcatcga cgagctgaag gccacctcct 14160
ccagcggtgc ggcggcggag gacgtaccgc tgctggacgc ggcctgccgg gaggtgctgc 14220
ggatctcgcc gcccgccgtg gtggccggca accgtgtgct caacgagggc caggagatcg 14280
acggggtacc gcacgacgcg ggcacccggc tgacgccgtg catctacctg gcgcaccagc 14340
agccggatct ctacccgcag ccggagcgct tcgacccgca ccgcttcctg ggcaagcgca 14400
agtccgccca ggagtacctg ccgttcggcg gcggcacccg ccgctgtctc ggtgccgacc 14460
tcgcgatgct ggagatgcgg atggtggtgg cggcggtgct gcgccggcga gaactgaagt 14520
gcgtcaatcc ggagaccggg gtaccgcagc tgcgcggtcc ggcgatgggt ccgagcgaag 14580

-continued acctgagaat gacggtgacc gagtgtccag catgatctcg gtaccaaatt ccagaaaaga 14640
gacgctgaaa agcgtctttt ttcgttttgg tccaagtatc aaatggctag gatataacct 14700
acacgattag gatagccccg catcaatcag agaaggaggt accaaaatgt gggagccgac 14760
gtctgcgggg tggggtgcgc gggtcgaggg gtgggatctg ggggcgccgt tgggtgcgga 14820
gtgtgcggcg gcgttggtgg agttgttccg tgcgcggcat ctgctggtgt tttcgggtca 14880
gggtttctcg ttggaggagc agatccggtt catggggcat ttgggtccgg tgctgcatga 14940
ggagggttcg gggatcgggt ttgtttcgaa tgtgaaggag ggggctgctc tgggggtgag 15000
tgagctgtct ttccattcgg atacggggca ttgtgcggtg ccgttggagg cggtgtcgct 15060
ttttgctgag gatgttgagg ggtgtgtgac gtcgacgcgg tttgcgaatg tggcggcggc 15120
gtatgggcgt ttgccggcgg gtttgcggtc gcgggttgcg ggactggtgt gtgagaacgc 15180
gatgccggtg tcgttggacg gccggaatgt ggggttgtcg gtggcggagg ggatgccgcg 15240
ggcggagcat ccggtggtgt ggcgtcatcc ggtgtcgggg gagccggggc tgatggtgaa 15300
tgcgaatcag acgacgcgga tcgtgggcct tgagggtgaa gagagccggg ggttgctgga 15360
ggagttgttc tcggtgatgt atgccgagga tgcggtgtat gagcattcct ggcagcaggg 15420
ggatgtggtg atctggcaca acctggcggt tcagcatgcg cggggtggcc tggaaggtaa 15480
tggccggcgg actctgcgcc gggtggcgtt gggtgagaag gggttttggg agcagtgccc 15540
gaccctgcgt tacgccgatt tcaaaaacca gcagaacacc gccgcgtgat aaaaaaaaaa 15600
aacaccctaa cgggtgtttt tttttttttg gtctcccgct ttgtgcgggc tctaacacgt 15660
cctagtatgg taggatgagc aaatcggatt aagaaggagg tacagtaatg acgtacgtaa 15720
tcgcgcagcc ctgtgtcgac ctcaaggaca aggcgtgcat cgaggagtgc ccggtcgact 15780
gcatctacga gggcaagcgg tccttgtaca tccacccgga cgaatgcgtc gactgcggtg 15840
cctgtgagcc ggtctgcccg gtcgaggcca tcttctacga ggacgacaca ccggaggagt 15900
ggaaggacta ctacaaggcg aatgtggagt tcttcgacga gctcggctcg ccgggcggcg 15960
ccgcccggct cggcctgatc gaccgcgacc accccgtcgt cgcggcgcag ccggtccgta 16020
cggccggagc cgcgggcgaa tgatctcggt accaaaaaaa aaaaaaaaga cgctgaaaag 16080
cgtctttttt ttttttggtc ccgctgtctt cactagtagc ggccgctgca ggagtcacta 16140
agggttagtt agttagatta gcagaaagtc aaaagcctcc gaccggaggc ttttgactaa 16200
aacttccctt ggggttatca ttggggctca ctcaaaggcg gtaatcagat aaaaaaaatc 16260
cttagctttc gctaaggaga ctcgctgcgc tcggtcgttc ggctgcggcg agcggtatca 16320
gctcactcaa aggcggtaat acggttatcc acagaatcag gggataacgc aggaaagaac 16380
atgtgagcaa aaggccagca aaaggccagg aaccgtaaaa aggccgcgtt gctggcgttt 16440
ttccataggc tccgcccccc tgacgagcat cacaaaaatc gacgctcaag tcagaggtgg 16500
cgaaacccga caggactata aagataccag gcgtttcccc ctggaagctc cctcgtgcgc 16560
tctcctgttc cgaccctgcc gcttaccgga tacctgtccg cctttctccc ttcgggaagc 16620
gtggcgcttt ctcatagctc acgctgtagg tatctcagtt cggtgtaggt cgttcgctcc 16680
aagctgggct gtgtgcacga accccccgtt cagcccgacc gctgcgcctt atccggtaac 16740
tatcgtcttg agtccaaccc ggtaagacac gacttatcgc cactggcagc agccactggt 16800
aacaggatta gcagagcgag gtatgtaggc ggtgctacag agttcttgaa gtggtggcct 16860
aactacggct acactagaag aacagtattt ggtatctgcg ctctgctgaa gccagttacc 16920
ttcggaaaaa gagttggtag ctcttgatcc ggcaaacaaa ccaccgctgg tagcggtggt 16980

-continued

```
tttttgttt gcaagcagca gattacgcgc agaaaaaaag gatctcaaga agatcctttg  17040
atcttttcta cggggtctga cgctcagtgg aacgaaaact cacgttaagg gattttggtc  17100
atgagattat caaaaaggat cttcacctag atccttttgg ttcatgtgca gctccatcag  17160
caaaagggga tgataagttt atcaccaccg actatttgca acagtgccgt tgatcgtgct  17220
atgatcgact gatgtcatca gcggtggagt gcaatgtcgt gcaatacgaa tggcgaaaag  17280
ccgagctcat cggtcagctt ctcaaccttg gggttacccc cggcggtgtg ctgctggtcc  17340
acagctcctt ccgtagcgtc cggcccctcg aagatgggcc acttggactg atcgaggccc  17400
tgcgtgctgc gctgggtccg ggagggacgc tcgtcatgcc ctcgtggtca ggtctggacg  17460
acgagccgtt cgatcctgcc acgtcgcccg ttacaccgga ccttggagtt gtctctgaca  17520
cattctggcg cctgccaaat gtaaagcgca gcgcccatcc atttgccttt gcggcagcgg  17580
ggccacaggc agagcagatc atctctgatc cattgcccct gccacctcac tcgcctgcaa  17640
gcccggtcgc ccgtgtccat gaactcgatg ggcaggtact tctcctcggc gtgggacacg  17700
atgccaacac gacgctgcat cttgccgagt tgatggcaaa ggttccctat ggggtgccga  17760
gacactgcac cattcttcag gatggcaagt tggtacgcgt cgattatctc gagaatgacc  17820
actgctgtga gcgctttgcc ttggcggaca ggtggctcaa ggagaagtcg cttcagaagg  17880
aaggtccagt cggtcatgcc tttgctcggt tgatccgctc ccgcgacatt gtggcgacag  17940
ccctgggtca actgggccga gatccgttga tcttcctgca tccgccagag gcgggatgcg  18000
aagaatgcga tgccgctcgc cagtcgattg gctgagctca tgagcggaga acgagatgac  18060
gttggagggg caaggtcgcg ctgattgctg gggcaacacg tggagcggat cggggattgt  18120
ctttcttcag ctcgctgatg atatgctgac gctcaatgcc gtttggcctc cgactaacga  18180
aaatcccgca tttggacggc tgatccgatt ggcacggcgg acggcgaatg gcggagcaga  18240
cgctcgtccg gggcaatga gatatgaaaa agcctgaact caccgcgacg tatcgggccc  18300
tggccagcta gctagagtcg acctgcaggt ccccggggat cggtcttgcc ttgctcgtcg  18360
gtgatgtact tcaccagctc cgcgaagtcg ctgttcttga tggagcgcat ggggacgtgc  18420
ttggcaatca cgcgcacccc ccggccgttt tagcggctaa aaaagtcatg gctctgccct  18480
cgggcggacc acgcccatca tgaccttgcc aagctcgtcc tgcttctctt cgatcttcgc  18540
cagcagggcg aggatcgtgg catcaccgaa ccgcgccgtg cgcgggtcgt cggtgagcca  18600
gagtttcagc aggccgccca ggcggcccag gtcgccattg atgcgggcca gctcgcggac  18660
gtgctcatag tccacgacgc ccgtgatttt gtagccctgg ccgacggcca gcaggtaggc  18720
cgacaggctc atgccggccg ccgccgcctt ttcctcaatc gcccttcgtt cgtctggaag  18780
gcagtacacc ttgataggtg ggctgccctt cctggttggc ttggtttcat cagccatccg  18840
cttgccctca tctgttacgc cggcggtagc cggccagcct cgcagagcag gattcccgtt  18900
gagcaccgcc aggtgcgaat aagggacagt gaagaaggaa cacccgctcg cgggtgggcc  18960
tacttcacct atcctgcccg gctgacgccg ttggatacac caaggaaagt ctacacgaac  19020
cctttggcaa aatcctgtat atcgtgcgaa aaaggatgga tataccgaaa aaatcgctat  19080
aatgaccccg aagcagggtt atgcagcgga aaagatccgt cgacctgcag gcatgcaagc  19140
tctagcgatt ccagacgtcc cgaaggcgtg gcgcggcttc cccgtgccgg agcaatcgcc  19200
ctgggtgggt tacacgacgc ccctctatgg cccgtactga cggacacacc gaagccccgg  19260
cggcaaccct cagcggatgc ccggggctt cacgttttcc caggtcagaa gcggttttcg  19320
```

-continued

```
ggagtagtgc cccaactggg gtaacctttg agttctctca gttgggggcg tagggtcgcc  19380
gacatgacac aaggggttgt gaccggggtg gacacgtacg cgggtgctta cgaccgtcag  19440
tcgcgcgagc gcgagaattc gagcgcagca agcccagcga cacagcgtag cgccaacgag  19500
gacaaggcgg ccgaccttca gcgcgaagtc gagcgcgacg gggccggtt caggttcgtc  19560
gggcatttca gcgaagcgcc gggcacgtcg gcgttcggga cggcggagcg cccggagttc  19620
gaacgcatcc tgaacgaatg ccgcgccggg cggctcaaca tgatcattgt ctatgacgtg  19680
tcgcgcttct cgcgcctgaa ggtcatggac gcgattccga ttgtctcgga attgctcgcc  19740
ctgggcgtga cgattgtttc cactcaggaa ggcgtgttcc ggcagggaaa cgtcatggac  19800
ctgattcacc tgattatgcg gctcgacgcg tcgcacaaag aatcttcgct gaagtcggcg  19860
aagattctcg acacgaagaa ccttcagcgc gaattgggcg ggtacgtcgg cgggaaggcg  19920
ccttacggct tcgagcttgt ttcggagacg aaggagatca cgcgcaacgg ccgaatggtc  19980
aatgtcgtca tcaacaagct tgcgcactcg accactcccc ttaccggacc cttcgagttc  20040
gagcccgacg taatccggtg gtggtggcgt gagatcaaga cgcacaaaca ccttcccttc  20100
aagccgggca gtcaagccgc cattcacccg ggcagcatca cggggctttg taagcgcatg  20160
gacgctgacg ccgtgccgac ccggggcgag acgattggga agaaaaccgc ttcaagcgcc  20220
tgggacccgg caaccgttat gcgaatcctt cgggacccgc gtattgcggg cttcgccgct  20280
gaggtgatct acaagaagaa gccggacggc acgccgacca cgaagattga gggttaccgc  20340
attcagcgcg acccgatcac gctccggccg gtcgagcttg attgcggacc gatcatcgag  20400
cccgctgagt ggtatgagct tcaggcgtgg ttggacggca gggggcgcgg caaggggctt  20460
tcccgggggc aagccattct gtccgccatg gacaagctgt actgcgagtg tggcgccgtc  20520
atgacttcga agcgcgggga agaatcgatc aaggactctt accgctgccg tcgccggaag  20580
gtggtcgacc cgtccgcacc tggcagcac gaaggcacgt gcaacgtcag catggcggca  20640
ctcgacaagt tcgttgcgga acgcatcttc aacaagatca ggcacgccga aggcgacgaa  20700
gagacgttgg cgcttctgtg ggaagccgcc cgacgcttcg gcaagctcac tgaggcgcct  20760
gagaagtcgg gcgaacgggc gaaccttgtt gcggagcgcg ccgacgccct gaacgccctt  20820
gaggagctgt acgaggaccg cgcggcaggc gcgtacgacg gacccgttgg caggaagcac  20880
ttccggaagc aacaggcagc gctgacgctc cggcagcaag gggcggagga gcggcttgcc  20940
gaacttgaag ccgccgaagc cccgaagctt ccccttgacc aatggttccc cgaggacgcc  21000
gacgctgacc cgaccggccc taagtcgtgg tgggggcgcg cgtcagtaga cgacaagcgc  21060
gtgttcgtcg ggctgttcgt agacaagatc gttgtcacga agtcgactac gggcaggggc  21120
cagggtaccc cgatcgagaa gcgggcctcc atcacctggg ccaagccgcc cacggacgac  21180
gacgaggacg acgcccagga cggcacggag gacgtagcgg cgtagcgaga cacccgggaa  21240
gcctgatcta cgtctgtcga gaagtttctg atcgaaaagt tcgacagcgt ctccgacctg  21300
atgcagctct cgcagggcga agaatctcgt gctttcagct tcgatgtagg agggcgtgga  21360
tatgtcctgc gggtaaatag ctgcgccgat ggtttctaca aagatcgtcc ggcaaaaaaa  21420
cgggcaaggt gtcaccaccc tgcccttttt ctttaaaacc gaaaagatta cttcgcgttt  21480
gccacctgac gtctaagaaa aggaatattc agcaatttgc ccgtgccgaa gaaaggccca  21540
cccgtgaagg tgagccagtg agttgattgc tacgtaatta gttagttagc ccttagtgac  21600
tcgaagaccc                                                         21610
```

<210> SEQ ID NO 31
<211> LENGTH: 21621
<212> TYPE: DNA
<213> ORGANISM: artificial
<220> FEATURE:
<223> OTHER INFORMATION: PB La2 gene cluster

<400> SEQUENCE: 31
ggagccgggc ggcttcctca tgcttgactt gactaggata aaggggctac aaggaagaag 60
gaggttaaca aatgaccgcc gccatcgtga gtgtcgccgc ccgcccgctg agcacggcgg 120
tgcgccacgg cgacgtggtg ctcgccgacc ggctgcacct ggcgtcgggc gcccgcgagg 180
gccgggtcca ccggctgctc gccggggccc tcagggcaca ggggctgacg gtccacaccg 240
gcggggccgc cgtcgccggc gccgaggcac cccagggcgc cgacgcaccg ctggtggaga 300
tcgccgcgcc ggtccggctc ccggaggcgg acggtgacgc gctgctgtgc ctggtgcgcg 360
acgacaccgg atcggacgcc gtcgaccgcg ccgaggaggc cctggcccgg gtcctgggcg 420
actgggaagc cgcgaagggg gaccgagcgg tggccctggc cgcccccegg tcgttctgcg 480 ccggtgtgga ccgtgccatc gagatcgtcg aacgcgccct cgaccagtac ggcgcccccg 540
tctacgtacg caagcagatc gtccacaacc ggcatgtcgt cgaggacctc gcccgccgcg 600
gcgcggtctt cgtcgaggag cttgacgagg tgccggaggg cgagctggtc gtcttctccg 660
cccacggggt cgccccggcg gtacgtgacg cggcgggcga gcgcggtctg cgagtgatcg 720
acgcgacctg cccgctggtc accaaggtcc atgccgaggc caagcggttc gcgggccgcg 780
gcgacaccgt cgtcctgatc gggcacgccg gtcacgagga ggtcgagggc acgctgggcg 840
aggcgcccga ccgcacggtg ctggtgcaga acgcggcgga ggcggcgcgc ctggaggtcg 900
aggaccccga ggcggtctcc ttcctcatgc agaccacgct ggcgatgtcc gaggccaccg 960
aggtggccca ggccctggcc ggccgcttcc cgtcgatcaa ggcaccgcag tccgaggaca 1020
tctgctacgc ctcgaccaac cggcagcgcg ccgtcgagga gatcgccggg cgggtcgatc 1080
tgctcctggt ggtcggatcg cccaactcct ccaactccgt acgcctgaag gaactcgcgg 1140
agcggatggg cacccccgcc cagctggtgg acgacgcctc gtacgtcggt ctggagcagc 1200
tgcacggggc ccggcggatc ggcctgacgg ccggcgcctc ggccccggac accctcgtcc 1260
aggaaatcgt cgccaatctc cgtgccctcg gacccgtcac ggtcaccgag caccaagtcg 1320
cgacggagaa cgtcaccttc cagctgccca aagagctgag gagcgcccgg aaagaccgcg 1380
cccgcaaaga cttggagaag accgttgaca gctgttgatc tcggtaccaa accaattatt 1440
aaagacgctg aaaagcgtct ttttttgttt cggtcctact cgcgtaggct aaagatgaca 1500
tctttaacat aggatgtgcg caaaaaaaag ggagaggagc gtatttaatg ccgacgacac 1560
cgctgcgtcg tcccacccgg cagctgatgc tcggcggcat gggcgtcggc agccgccacc 1620
ccgtctcggt gcagtcgatg acgaccacgg tgacggccga tgcccaggcc acccttcagc 1680
agatagccga actcaccgcg gcgggctgcg acatcgtccg ggtcgcctgc cccagccggg 1740
acgacgccga agccctcgcg gagatcgccc agaagtcgaa gatccccgtc atcgcggaca 1800
tccacttcca gccgcgctat gtcttcgccg cgatcgaggc gggctgcgcc ggtgtccggg 1860
tcaacccggg caacatcaag gaattcgacg acaagatcaa ggagatcgcg caggccgcga 1920
aggaggccgg caccccgatc cgcatcgggg tcaacgcggg ctcgctcgac ccgaggatcc 1980
tgcggaagtt cggcaaggcg accccggagg ccctggccga atcggcgctg cgcgaggcgg 2040
agctgttcgc ggagcacgac ttccacgact tcaagatctc ggtgaagcac cacgacccga 2100

```
tggtgatgat ccgggcgtac gagctgctgg ccgcgcagtg cgactacccg ctccacctcg   2160
gcgtcaccga ggcgggaccg gccttccagg gcacggtcaa gtcctcggtg gccttcggcg   2220
cgctgctgcg ccagggcatc ggcgacacca tccgcgtctc gctgtccgca ccgcccgtgg   2280
aggaggtcaa ggtcggcatc cagatcctcc agtcgctcgg cctgcgcccc cggcgcctgg   2340
agatcgtctc ctgcccgtcc tgcggccgcg cccaggtgga cgtctacaag ctcgccgaag   2400
aggtgagcgc cgggctcgaa gggcttccgg tgccgctgcg ggtcgccgtc atggctgtg    2460
tcgtcaacgg tcccggcgag gcccgcgagg ccgacctcgg tgtcgcctcc ggcaacggca   2520
aggggcagat cttcgtcaag ggcgaggtcg tcaagaccgt ccccgagtcg aagatcgtcg   2580
agaccctcat cgaagaggca ctgcgcctcg cggacgagat gggggtggac ctcgatgaga   2640
ctggctgatc tcggtaccaa attccagaaa agagacgctg aaaagcgtct tttttcgttt   2700
tggtccaggt cgcgtaggct aaagatgaca tctttaacat aggatgtgcg caaaaaaaag   2760
ggagaggagc gtatttaatg agactggctg acctcaccgg tccgggcgat ctcgccgcac   2820
tgacggagga tcaactccag gcgctggccg cggacatccg ctcctttctc gtggagtccg   2880
tttcgaaggt cggcggacac ctgggcccca acctcggcgt cgtcgagctc accctcgccc   2940
tgcaccgggt cttcgagtcc cccaaggaca ccctgctgtt cgacaccggc caccaggcct   3000
acgtccacaa gctgctcacc ggccggatga aggccttctc gacgctgcgc caggaaggcg   3060
ggctctccgg ctatcccgac cgcagcgagt ccgagcacga tgtcatcgag aactcccatg   3120
cctccacggc cctttcgtac gcagacggca tcgccaaggg cttcggcctg gccggcgccg   3180
cgcaccgcag ggtggtcgcc gtcgtcggcg acggcgcgct gaccggcggg atgagctggg   3240
aggcgctcaa caacatcggc ggcgccccgg accgcccggt gatcatcgtc ctgaacgaca   3300
acggccgttc ctacgccccc accgccggcg ccctcgccac ccacctcggc gagctccggg   3360
cgggccgcgg cggggccggt ctcttcgcga acctgggcct cgcctacctg ggcccggtcg   3420
acggccacga ccgcccggca ctcgagcgcg cactgcgccg ggcggccgca ctcgaccgcc   3480
ccgtggtggt gcactgtgtg acgcagaagg gccacggtta cgcaccggcc gccgaggacc   3540
ccgacgactg ctggcacgcg gtgggcacct tcgaccccga gaccggcggc aagtccgctt   3600
ccggcggccg ctcctggacc gcggtgttcg gtgcggagat gacggaactc ggtgcgcagc   3660
ggcccgacgt ggtcgccctc accgccgcga tgctccagcc cgtgggcctg gccgacttcg   3720
cccgccgctt ccccgaccgg gtcttcgacg tcggcatcgg cgaacagcat gccgccgtct   3780
ccgccgccgg gctggcgcac accgggctgc accccgtcgt ggccgtctac tccaccttcc   3840
tcaaccgcgc cttcgaccag gtgctgatgg atgtggcgct gcaccggcag ccggtgacct   3900
tcgtactcga ccgggcgggt gtcaccggcc ccgatggccc cagccatcac gggatctggg   3960
acgcctcctg gctgtcgctg gtaccggggc tgcgcctggc ggtgccgcgc gatgccgagg   4020
aactcaggac gctgctgcgg gaggcggtcg ccgtcacgga cgggcccacc gtcctccgct   4080
tcccgaaggc acaggccggc ccggccgtgc cggcgctccg ccgggagggg ggcatggacg   4140
tgctgcacga ggcgcccggc gcccgggtgc tgctggtccc gaccggtccg ctcgccgacc   4200
cgtgccttca ggccgcggcc gcgctggacg ccctgggcat cccgtcgacg gtggtggacc   4260
cgcgctggtc cgtccccgta ccggaggggc tgccggagct ggccgcacgg cacgaactcg   4320
tggtgaccgt cgaggacaac ctgagcgacg gcgggctcgg cgcgcgcctg ctgcgacagc   4380
tgtccgaggc cggcacgccc acccccgtac ggaccgtcgg cctgccgacg gagttccttc   4440
cccacggcag caggacggcc ctcctgcgcc ggcatgggct caccgccgac ggcctggtcg   4500
```

```
cacgggtcgg cggatggctg ccacaagcgg ccccccgctg ataaaaaaaa aaaacaccct   4560
aacgggtgtt tttttttttt tggtctcccg ctttgtgcgg gctctaacac gtcctagtat   4620
ggtaggatga gcaaatcgga ttaagaagga ggtacagtaa tgacggactc cctcgcccac   4680
ccgcatacgc gtttcgagcc ggcctccggc gaccctgacg gcccgcgcgg cccccgttcc   4740
ctcgtggtgc tcggctcgac cggctcgatc ggcacccagg cgatcgacat cgtgctgcgc   4800
aatcccgacc gcttccgggt gaccgcgctc tccgcggccg gcggccgggt cgagctgctc   4860
gccgatcagg cgcaccagct gcgggtggcc gccgtcgccg tggcgcgcga ggacgcggtg   4920
cccgcgctgc gtacggcact ggccgaccgc tacggcgcgg gcgagccgct gcccgagatc   4980
ctggccggcc ccgacgcggc caccgagctg gccgcctccc cctgccacac cgtcctcaac   5040
ggcatcaccg gctccatcgg cctcgccccg accctggccg ccctgaaggc gggccgggtg   5100
ctggccctcg ccaacaagga gtcgctgatc gtcggcggcc cgctggtcaa ggccctcgcc   5160
gagcccggcc agatcatccc cgtcgactcc gagcactccg cgctgttcca ggcgctggcc   5220
ggcggcgagc gcgccgaggt ccgcaagctc gtcgtcaccg cttccggcgg tccgttccgc   5280
ggccgtacga agaaggagct ggccggggtc acgcccgagc aggcgctggc ccaccccacc   5340
tggtcgatgg gcccggtcgt caccatcaac tcggcgaccc tcgtcaacaa gggcctggag   5400
gtcatcgagg cgcatctgct gttcgacgtg cccttcgacc gcatcgaggt cgtcgtccac   5460
ccgcagtcct acatccactc gatggtggag ttcaccgacg gctccacgct cgcccaggcc   5520
agcccgcccg acatgcggat gccgatcgcg ctgggcatcg gctggcccga gcgggtcccg   5580
gacgccgcac cgggcgtgga ctggacgaag gcgcagacct gggagttctt cccgctggac   5640
gaggaggcct tcccgtccgt cccgctggcc cgccacgtcg gtgatctggg cggcaccgcc   5700
cccgccgtct tcaacgcggc gaacgaggaa tgcgtggacg cgttcctcaa gggcgggctg   5760
cccttcacag ggattgtgga taccgtcgcc gcagtggtcg ccgaacacgg aacgcccgcc   5820
gggggaactt ccctgagtgt cgcggacgtc ctcgaggcgg agacctgggc gcgcgcccgc   5880
gcccgcgaac tggccgcccg tgcggcacgg acaccttcgg aggctcgcgc atgatcagat   5940
aaaaaaaatc cttagctttc gctaaggatg atttctcgct cttagaggct ggtgtcaact   6000
agatcaccat aggattcacc acgaagatag aaggaggtta taaaatgtca gatccttccc   6060
gcccggtccg caccgccgcg gtgatccccg ccgccggccg cggtgtccgg ctcggtcccg   6120
gcacccccaa ggcgctgcgc acgctgggcg gcacccccat gctggtgcac gccgtccgcg   6180
cgatggccgc ctcgcgcgcg gtctccctca tcgtggtggt ggccccgccc gacggcgccg   6240
ccgaggtcag ccgcctgctc cacgagcacc cgctcgccga acgcaccgag ctcgaggtcg   6300
tccccggcgg cgaaacccgc caggagtccg tacagctcgg tctggcggcg ctcccggaca   6360
ccatcgacgt cgtgctggtg catgacgccg cgcgcccgct ggtcccggtc gacacggtcg   6420
acacggtggt cgcggccgta cgcgccggtg cgccggccgt cgtcccggcg ctgccgctcg   6480
ccgacaccgt caagcaggtc gacccgcagc cgcagggcac cccggagccg gtggtcggca   6540
ccccggagcg gtccctgctg cgcgccgtgc agaccccgca gggcttcgac ctggcgaccc   6600
tgcgcaaggc gcatgacacc gtcgtcgagg gcgagggcgc caccgatgac gccgggctgg   6660
tcgaacggct cggttcgccg gtcgtggtcg tcccgggcca cgaggaagcg ttcaaggtga   6720
cccggccgct ggacctggtc ctggccgagg ccgtactcgc ccgcaggagg gccaccgatg   6780
gctatgtctg attccggcaa ttaaaaaagc ggctaaccac gccgcttttt ttacgtctgc   6840
```

-continued

```
aggagtcaaa tggctaggat ataacctaca cgattaggat agccccatcc accaatacgc   6900
acagaaggag attataaatg acgttcacca cctcgatcac cgtccgggta ccggccaagg   6960
tcaacgtcca gctggccgtc ggcgccgccc gcccggacgg cttccacgac ctggccaacg   7020
tcttcctcgc cgtcggcctc tacgacgagg tcaccgcgac cccgccgag tccctgcgga    7080
tcaccgccga gggccacgac gtcgaccaga tcccgctgga ccggacgaac ctggccgccc   7140
gcgcagccga actgctcgcc gcccggcacg gcatcgagcc gcacgtccac ctccacatca   7200
ccaaggacat ccccgtcgcc ggcggcatgg cgggcggcag cgcggacgcc gccggggccc   7260
tgctggcctg cgacgccctg tggtcgacgg gtgcctcgcg cgaggaactc ctttccctct   7320
gcgccgagtt gggcagcgat gtgccgttca gcctggtggg tggcgcggcc ctgggacgcg   7380
gccgtggcga actcctgacc cccctccccg tcggcggcgc cttccactgg gtcttcgcgg   7440
tcgccgacgg cgggctgtcc accccggccg tctacggcga gttcgaccgg ctgacggcgg   7500
gcaccgaggt gcccgagccc gaggcggacc cagccctgct ggccgccctg gagaccggcg   7560
acgccaccgc gctcgccgcg gccctcacca acgacctcca gcccgcggcc ctgtccctgc   7620
gcccgtccct gaccgcgacg ctggaggccg gcaccgccgc cggcgccctg gccgcgctgg   7680
tctccggctc cgggccgacc accgccttcc tggccaagga cgcggaggcg gcaaaggaag   7740
tggcatcggc gctgctggcg tcggggacct gccgtcaggt gcgggtggcg gattctccgg   7800
cggtgggggc gagggttctt tgatgtcagt ttcacctgtt ttacgtaaaa acccgcttcg   7860
gcgggttttt acttttggta cttgttcaca ttcgaaccgt ctctgctttg acaacatgct   7920
gtgcggtgtt gtaaagtctg gtgtatctaa gtaaggagac atctaatgtc tgacccgacc   7980
ccttccggcg cgctccccgg cgcccctctc gtccccctcg tcggcatcgg cacggatgtg   8040
cacgccttcg agcagggccg ggagctgtgg tgcgcgggtc tgctctggga caccacggag   8100
agcgacggct acggcctggc cggtcacagc gacggcgatg tggccgcgca tgccgcctgt   8160
gacgcactgt tctcggcggc cggcgtcggc gacctgggtg cccacttcgg caccagccgc   8220
cccgagtggt ccggcgcctc cggagtgacc ctgctggccg aggccgcccg gatcgtacgg   8280
gccgagggct tcaccatcgg caatgtcgcg gtgcaggtca tcggcgtacg cccgaaggtc   8340
ggcaagcggc gggacgaggc ccaaaaggcg ctgtcggcgg ccgtcggcgc gccggtctcg   8400
gtctccggga cgacctcgga cgggctgggc ctgacgggcc gcgccgaggg cctggccgcg   8460
gtggccacgg cgatcgtctt ccgtacggcc tgatgacgaa caataaggcc tccctaacgg   8520
ggggcctttt ttattgataa caaaaaggtt gttcacattc gaaccgtctc tgctttgaca   8580
acatgctgtg cggtgttgta aagtctggtg tatctaagta aggagacatc taatgccgat   8640
cacaccggcc aacggacaga ccgccggcga cccggcggtg agcacaccgg gcggcaccgc   8700
cgaaccgatc atgctggagc tggtcgacga ggacggtacg acgatcggca ccgcggagaa   8760
gctcgcggcc caccagcctc ccgggcagct gcaccgggcg ttctccgtct tcctcttcga   8820
cgagaagggg cggctgctgc tccagcgccg ggcactgggg aagtaccact cccccggtgt   8880
gtggtccaac acgtgctgcg gccacccgta tcccggcgag gcgccgttcg tggccgcggc   8940
ccggcgcacc tccgaggagc tgggcctggc acccgccctg ctggccgagg cgggcaccgt   9000
gcgttacaac catcccgacc cggcctccgg ccttgtggag caggagtaca accacctgtt   9060
cgtcgggctg gtgcgggccg agccggcgcc cgatcccgag gagatcggcg agatcgcgtt   9120
cgtgacgccg caggagctgg ccgagcggca tgccgaggcg ccgttctccg cgtggttcat   9180
gaccgtcctg gacgcggcgc gtccggcggt gcgcgagctc acaggactgt cggcgggctg   9240
```

```
gtgatctcgg taccaaaaaa aaaaaaaaag acgctgaaaa gcgtcttttt tttttttggt   9300
ccgcttcagg tcggctggtt ggctgacaaa gtgcgtagga tgactgtgca tcaatcagag   9360
aaggaggtac caaatgacgt cggaactgcc cgccgcacgc ggcgaagggc tgcggagcct   9420
cgtccgcatc caccggctgg aataccccctt tccggtcatc tatctctgcc atgtcctgtg   9480
gggcgcctgc ctcgcggcga cgggtccggg cagcctggcc gccgcgcccg tcctgatcat   9540
gctgttcgcc aatatcgtcg cgatcatctc ccagaacccg ctcaacgccg gtctggacat   9600
ccgggcggac acccacacca gcggcaagga gagcatcgcc cgcgccaccc agcacctcag   9660
cgtccgcacc gcgttcacgt gcgcggcact ggagatggcg ctcgccctcg ggctgtccgt   9720
ctgggtcgcg ctctggctcg gccggccgct cgtcgcggtg gggtggcgc tgtcgatcgt   9780
gctccacctc gcctacaacc tggagccggt ccggctgaag cggcgcggct acgccaaccc   9840
cgcctacttc ggggcgacct tcgccttcct gccgtcgctg tcgacgtatg cggcggtgcg   9900
ggcggacgta ccgctcagcg cgtggctgtt cctcaccggg ctcggcatcc tgctgttcgg   9960
ccgctccctg tggtggtgca tcccggacct gatcggtgac gccaaggccg ggaccgtac  10020
gcccgccgta cagcacggcc cgcgccatgc gctggtggtg gcgtgcctgt ggaccgcgct  10080
cgggctgctg ttcatcggcg ccgggctgtg gccgtacggc gtcctctggg cgctgctcgg  10140
catcctggcg agcgccgcct tcctcgtgga caagatcaag ctgctgcggc acatctcgcg  10200
ggagaacctc ccgcacgagt ccacgatgcg caagcacagc ctctcgctgg cgatgggcgg  10260
cgacctcctg ctctgcgcca tcccgctgct cgcgctctga tcagataaaa aaaatcctta  10320
gctttcgcta aggatgattt ctcgctaccc gtggctactc agcgaataac tcttgtagga  10380
tacataaaaa aaaaagggag aggagcgtat ttaatgctcg aagttcccgc tcagcccacg  10440
cccgcccccc gcgaggccga ggcggccgcg ctgctcgcgg cgaccgtcca cgacccctgg  10500
ggcctggtcg ctccgtcggt gtacgacacc gcccggctgg tctccctcgc cccgtggctc  10560
gacggccacc gggagcgtct cggctatctg gtcgaggagc agaaccagga cggaagctgg  10620
ggcgcacccg acgggtacgg cctggtaccc acgctcagtg cggtggaggc gctgctgacc  10680
gaactcgccc ggccggaatc cggcgcgccg cacccgcccc acgacgacct cgccgcggcc  10740
tgcgccggcg gtctgggcgc cctccaggac ggtctgctcg ccggtccggt gcccgacacc  10800
atcggcgtcg agttcgtcgc gccgtccctg ctcgcggaca tcaacacccg gctggccgcg  10860
ctgaccgagc aggcacccgg caagctcggg gcatggtccg gcaccaccct gacgtcaccg  10920
gcgcccgacc tggacggtgc gctgctggcc ggcgtccggg agatgaccga gcaggcgccg  10980
ctgccggaga agctgtggca cacactggag gccatcaccc gcgacggcac ccgcggtgcc  11040
cggccgcacg agggcgcacc gccgcacaac ggctcggtcg gctgctcccc cgccgccacc  11100
gccgcctggc tgggcgcctc gcccgatccg gccgcgccgg gcgtcgccta tctccgtgac  11160
gtccaggcgc ggttcggcgg gccggtgccc tcgatcaccc cgatcgtcta cttcgagcag  11220
gcgtgggtcc tcaactcgct ggccgcctcc ggcctgcgct acgaggcccc ggccgcgctc  11280
ctcgacagcc tcgaagcggg tctcacggac gagggcacag ccgccgcccc cggtctgccg  11340
agcgactccg acgacaccgc cgccgtcctc ttcgccctgg cgcagcacgg caggacgcac  11400
cgccccgaca gcctgatgca cttccgccgg gacggctact tctcctgctt cggcgtcgag  11460
cgcacccccct ccaccagcac caacgcacac atcctggagg ccctcggcca tcacgtcacg  11520
gtgcgccccg acgacgcggg acgctatggc gcggagatcc ggatgatcag cgactggctg  11580
```

-continued

```
ctggacaacc agctgcccga cggcagctgg atggacaagt ggcacgcctc gccgtactac  11640

gccacggcct gctgtgcgct ggcgctcgcc gagttcggcg gcccgtccgc acgggccgcg  11700

gtcggccggg ccgccgcgtg ggcactggcg acccagcgcg ccgacggctc ctggggacgc  11760

tggcagggca ccacggagga gaccgcgtac atggtgcagc tcctgatgcg tacccgtacc  11820

cccgggagcc cggggaccgt cgcccggtcg gcggcccgcg gctgcgacgc gctgctggcc  11880

cacgacgacc cggcctccta ccccgggctc tggcacgaca aggacatcta cgcgccggtg  11940

accgtcatcc gggcggcgcg gctcgcggca ctggcgctcg gcggcgccga gtccgccgct  12000

tccggaggtg cttgatcaga taaaaaaaat ccttagcttt cgctaaggat gatttctgga  12060

gtagcagggc tccaaaacta acgcctgatg taggatcaga tggctacaag gaagaaggag  12120

gttaacaatg cacgctgaca cagtccagcc cctcgagagc agtgtcgacc tggcccaccg  12180

caacgcctcg cgggccgccg gcctcgtcac gcccgccctg cgggccaccg tcgacacctt  12240

cgacaaccgc atccgcccca tcgtcgccta ccacttcggc tggatggaca ccagcggacg  12300

ccccacggcg aacagcggcg gcaagatgat ccgggcggca ctgaccatcc ttgccgccga  12360

ggcctgcggc ggcgacgccc agcaggccgt acccggcgcc gccgccgtcg aactggtcca  12420

caacttctcg ctgttgcacg acgacgtcat ggaccgcgat ctggagcggc gcggccggcc  12480

cacggtatgg agcaagttcg gcacccccgc ggcgatcctg gcgggcgaca tcctgctggc  12540

gcgcgcctgc ggcatgttcg acgaggcctc cggccaccag ggctgggcga ccaaggccct  12600

gatcgacgcg atcgccgagc tggccgcggg ccagatggcc gacctcgcgc tggagcgccg  12660

cgccacggtg accctggaag aggccctcac cgtctccgag cagaagaccg cggcgctgct  12720

gcgctgcgcc tgcacgctgg gcgcgggact cgtcggcgca cccgacggga ccagccgccg  12780

cttcggcgcc ttcggtatgc acctgggcat ggcgttccag ctggtcgacg acgtactcgg  12840

catatggggc gacccggccg tcaccggcaa gccggtccgc tccgacctgc acaacaagaa  12900

gaagagcatt cccgtcgtcg ccgccctcca cagcggccgg cccggctccg cggaactggc  12960

cgcgctctac gcggacaccg accccatgac ggaggacggc gcccggcgcg ccgccgagct  13020

ggtcgagctg gccggcggcc gcgcctggac cgagagcgag atcgagcggc accgcggcct  13080

cgccgtggcg cagctcgacg ccctcgggct gacggaggcg cagcgggcac ccctgctcgc  13140

cctcgccgac tacgtcgcct tcaggaagca ctgatgtcag tttcacctgt tttacgtaaa  13200

aacccgcttc ggcgggtttt tacttttggt actcgcgtag gctaaagatg acatctttaa  13260

cataggatgt gcgcaaaaaa aagggagagg agcgtattta atgaccaccc gccccacggc  13320

cgcctcgcgc ggcaacaagt accgcttcgc cttccgcacc ctctccttcc tggacgccca  13380

caagaacgac cgctccggtg tggccgagct cagcgggccg cccggccggg cgctcctggt  13440

gtggaagccg gagatcatca gccaggtctt ccgcggcgac cggaacatga cgctggaggg  13500

ctccgacacg ctcggcccgc tggtcggcga cacctcgctg ctgttcgcca acgggccgcg  13560

gcacgccgcg taccgccagg tgatcggccc gcggctgcgc ggccgtccgc tgcgcggcta  13620

cgaggagctg atcgccgagg ccacccgggc ggcgatcgac gaactgcggc cgggcaccga  13680

cttccaggtg cccgactgga cccgcaggct caccctttcag atcgtcagcc agatcatcct  13740

cggcccggtg gaccacggtc tgctgcaccg cttcacctcc tggatcgagg gggtgctggg  13800

ctcgcgcggc cgcaccctcg cctaccgcta tctgcggctg ccgcacgccc tgccgtctcc  13860

ctggcgcacc tttgtgcggc agcgcgagag cctggacaag gagctgctgt gcccggtgag  13920

cggcaagagc gccggcggcg gtgcgggttc cggtgcgccg gagccgtcgc cggccacgct  13980
```

cgccgaggtg ctgcgcagcg gtgaggagcc gctcggcccg ctgggcgacg gcgaactgcg 14040
tgaccagatc gtctcgttgc tgttcgcggg ccacgagacg accgcctcgg cgatctcctg 14100
ggcgctgttc tggctcgcgg agcacgacga ggtgcgccgc gacatcatcg acgagctgaa 14160
ggccacctcc tccagcggtg cggcggcgga ggacgtaccg ctgctggacg cggcctgccg 14220
ggaggtgctg cggatctcgc cgcccgccgt ggtggccggc aaccgtgtgc tcaacgaggg 14280
ccaggagatc gacggggtac cgcacgacgc gggcacccgg ctgacgccgt gcatctacct 14340
ggcgcaccag cagccggatc tctacccgca gccggagcgc ttcgacccgc accgcttcct 14400
gggcaagcgc aagtccgccc aggagtacct gccgttcggc ggcggcaccc gccgctgtct 14460
cggtgccgac ctcgcgatgc tggagatgcg gatggtggtg gcggcggtgc tgcgccggcg 14520
agaactgaag tgcgtcaatc cggagaccgg ggtaccgcag ctgcgcggtc cggcgatggg 14580
tccgagcgaa gacctgagaa tgacggtgac cgagtgtcca gcatgatctc ggtaccaaat 14640
tccagaaaag agacgctgaa aagcgtcttt tttcgttttg gtccaagtat caaatggcta 14700
ggatataacc tacacgatta ggatagcccc gcatcaatca gagaaggagg taccaaaatg 14760
tgggagccga cgtctgcggg gtggggtgcg cgggtcgagg ggtgggatct gggggcgccg 14820
ttgggtgcgg agtgtgcggc ggcgttggtg gagttgttcc gtgcgcggca tctgctggtg 14880
ttttcgggtc agggtttctc gttggaggag cagatccggt tcatggggca tttgggtccg 14940
gtgctgcatg aggagggttc ggggatcggg tttgtttcga atgtgaagga gggggctgct 15000
ctgggggtga gtgagctgtc tttccattcg gatacggggc attgtgcggt gccgttggag 15060
gcggtgtcgc tttttgctga ggatgttgag gggtgtgtga cgtcgacgcg gtttgcgaat 15120
gtggcggcgg cgtatgggcg tttgccggcg ggtttgcggt cgcgggttgc gggactggtg 15180
tgtgagaacg cgatgccggt gtcgttggac ggccggaatg tggggttgtc ggtggcggag 15240
gggatgccgc gggcggagca tccggtggtg tggcgtcatc cggtgtcggg ggagccgggg 15300
ctgatggtga atgcgaatca gacgacgcgg atcgtgggcc ttgagggtga agagagccgg 15360
gggttgctgg aggagttgtt ctcggtgatg tatgccgagg atgcggtgta tgagcattcc 15420
tggcagcagg gggatgtggt gatctggcac aacctggcgg ttcagcatgc gcggggtggc 15480
ctggaaggta atggccggcg gactctgcgc cgggtggcgt tgggtgagaa ggggttttgg 15540
gagcagtgcc cgaccctgcg ttacgccgat ttcaaaaacc agcagaacac cgccgcgtga 15600
taaaaaaaaa aaacacccta acgggtgttt tttttttttt ggtctcccgc tttgtgcggg 15660
ctctaacacg tcctagtatg gtaggatgag caaatcggat taagaaggag gtacagtaat 15720
gacgtacgta atcgcgcagc cctgtgtcga cctcaaggac aaggcgtgca tcgaggagtg 15780
cccggtcgac tgcatctacg agggcaagcg gtccttgtac atccacccgg acgaatgcgt 15840
cgactgcggt gcctgtgagc cggtctgccc ggtcgaggcc atcttctacg aggacgacac 15900
accggaggag tggaaggact actacaaggc gaatgtggag ttcttcgacg agctcggctc 15960
gccgggcggc gccgcccggc tcggcctgat cgaccgcgac caccccgtcg tcgcggcgca 16020
gccggtccgt acggccggag ccgcgggcga atgatctcgg taccaaaaaa aaaaaaaaag 16080
acgctgaaaa gcgtcttttt tttttttggt cccgctgtct tcactagtag cggccgctgc 16140
aggagtcact aagggttagt tagttagatt agcagaaagt caaaagcctc cgaccggagg 16200
cttttgacta aaacttccct tggggttatc attggggctc actcaaaggc ggtaatcaga 16260
taaaaaaaat ccttagcttt cgctaaggag actcgctgcg ctcggtcgtt cggctgcggc 16320

-continued

```
gagcggtatc agctcactca aaggcggtaa tacggttatc cacagaatca ggggataacg  16380
caggaaagaa catgtgagca aaaggccagc aaaaggccag gaaccgtaaa aaggccgcgt  16440
tgctggcgtt tttccatagg ctccgccccc ctgacgagca tcacaaaaat cgacgctcaa  16500
gtcagaggtg gcgaaacccg acaggactat aaagatacca ggcgtttccc cctggaagct  16560
ccctcgtgcg ctctcctgtt ccgaccctgc cgcttaccgg atacctgtcc gcctttctcc  16620
cttcgggaag cgtggcgctt tctcatagct cacgctgtag gtatctcagt tcggtgtagg  16680
tcgttcgctc caagctgggc tgtgtgcacg aaccccccgt tcagcccgac cgctgcgcct  16740
tatccggtaa ctatcgtctt gagtccaacc cggtaagaca cgacttatcg ccactggcag  16800
cagccactgg taacaggatt agcagagcga ggtatgtagg cggtgctaca gagttcttga  16860
agtggtggcc taactacggc tacactagaa gaacagtatt tggtatctgc gctctgctga  16920
agccagttac cttcggaaaa agagttggta gctcttgatc cggcaaacaa accaccgctg  16980
gtagcggtgg tttttttgtt tgcaagcagc agattacgcg cagaaaaaaa ggatctcaag  17040
aagatccttt gatcttttct acggggtctg acgctcagtg gaacgaaaac tcacgttaag  17100
ggattttggt catgagatta tcaaaaagga tcttcaccta gatcctttg gttcatgtgc  17160
agctccatca gcaaaagggg atgataagtt tatcaccacc gactatttgc aacagtgccg  17220
ttgatcgtgc tatgatcgac tgatgtcatc agcggtggag tgcaatgtcg tgcaatacga  17280
atggcgaaaa gccgagctca tcggtcagct tctcaacctt ggggttaccc ccggcggtgt  17340
gctgctggtc cacagctcct tccgtagcgt ccggcccctc gaagatgggc cacttggact  17400
gatcgaggcc ctgcgtgctg cgctgggtcc gggagggacg ctcgtcatgc cctcgtggtc  17460
aggtctggac gacgagccgt tcgatcctgc cacgtcgccc gttacaccgg accttggagt  17520
tgtctctgac acattctggc gcctgccaaa tgtaaagcgc agcgcccatc catttgcctt  17580
tgcggcagcg gggccacagg cagagcagat catctctgat ccattgcccc tgccacctca  17640
ctcgcctgca agcccggtcg cccgtgtcca tgaactcgat gggcaggtac ttctcctcgg  17700
cgtgggacac gatgccaaca cgacgctgca tcttgccgag ttgatggcaa aggttcccta  17760
tggggtgccg agacactgca ccattcttca ggatggcaag ttggtacgcg tcgattatct  17820
cgagaatgac cactgctgtg agcgctttgc cttggcggac aggtggctca aggagaagtc  17880
gcttcagaag gaaggtccag tcggtcatgc ctttgctcgg ttgatccgct cccgcgacat  17940
tgtggcgaca gccctgggtc aactgggccg agatccgttg atcttcctgc atccgccaga  18000
ggcgggatgc gaagaatgcg atgccgctcg ccagtcgatt ggctgagctc atgagcggag  18060
aacgagatga cgttggaggg gcaaggtcgc gctgattgct ggggcaacac gtggagcgga  18120
tcggggattg tctttcttca gctcgctgat gatatgctga cgctcaatgc cgtttggcct  18180
ccgactaacg aaaatcccgc atttggacgg ctgatccgat tggcacggcg gacggcgaat  18240
ggcggagcag acgctcgtcc gggggcaatg agatatgaaa aagcctgaac tcaccgcgac  18300
gtatcgggcc ctggccagct agctagagtc gacctgcagg tccccgggga tcggtcttgc  18360
cttgctcgtc ggtgatgtac ttcaccagct ccgcgaagtc gctgttcttg atggagcgca  18420
tggggacgtg cttggcaatc acgcgcaccc cccggccgtt ttagcggcta aaaaagtcat  18480
ggctctgccc tcgggcggac cacgcccatc atgaccttgc caagctcgtc ctgcttctct  18540
tcgatcttcg ccagcagggc gaggatcgtg gcatcaccga accgcgccgt gcgcgggtcg  18600
tcggtgagcc agagtttcag caggccgccc aggcggccca ggtcgccatt gatgcgggcc  18660
agctcgcgga cgtgctcata gtccacgacg cccgtgattt tgtagccctg gccgacggcc  18720
```

-continued agcaggtagg ccgacaggct catgccggcc gccgccgcct tttcctcaat cgcccttcgt 18780
tcgtctggaa ggcagtacac cttgataggt gggctgccct tcctggttgg cttggtttca 18840
tcagccatcc gcttgccctc atctgttacg ccggcggtag ccggccagcc tcgcagagca 18900
ggattcccgt tgagcaccgc caggtgcgaa taagggacag tgaagaagga acacccgctc 18960
gcgggtgggc ctacttcacc tatcctgccc ggctgacgcc gttggataca ccaaggaaag 19020
tctacacgaa ccctttggca aaatcctgta tatcgtgcga aaaaggatgg atataccgaa 19080
aaaatcgcta taatgacccc gaagcagggt tatgcagcgg aaaagatccg tcgacctgca 19140
ggcatgcaag ctctagcgat tccagacgtc ccgaaggcgt ggcgcggctt ccccgtgccg 19200
gagcaatcgc cctgggtggg ttacacgacg cccctctatg gcccgtactg acggacacac 19260
cgaagccccg gcggcaaccc tcagcggatg ccccggggct tcacgttttc ccaggtcaga 19320
agcggttttc gggagtagtg ccccaactgg ggtaaccttt gagttctctc agttgggggc 19380
gtagggtcgc cgacatgaca caaggggttg tgaccggggt ggacacgtac gcgggtgctt 19440
acgaccgtca gtcgcgcgag cgcgagaatt cgagcgcagc aagcccagcg acacagcgta 19500
gcgccaacga ggacaaggcg gccgaccttc agcgcgaagt cgagcgcgac gggggccggt 19560
tcaggttcgt cgggcatttc agcgaagcgc cgggcacgtc ggcgttcggg acggcggagc 19620
gcccggagtt cgaacgcatc ctgaacgaat gccgcgccgg gcggctcaac atgatcattg 19680
tctatgacgt gtcgcgcttc tcgcgcctga aggtcatgga cgcgattccg attgtctcgg 19740
aattgctcgc cctgggcgtg acgattgttt ccactcagga aggcgtgttc cggcagggaa 19800
acgtcatgga cctgattcac ctgattatgc ggctcgacgc gtcgcacaaa gaatcttcgc 19860
tgaagtcggc gaagattctc gacacgaaga accttcagcg cgaattgggc gggtacgtcg 19920
gcgggaaggc gccttacggc ttcgagcttg tttcggagac gaaggagatc acgcgcaacg 19980
gccgaatggt caatgtcgtc atcaacaagc ttgcgcactc gaccactccc cttaccggac 20040
ccttcgagtt cgagcccgac gtaatccggt ggtggtggcg tgagatcaag acgcacaaac 20100
accttccctt caagccgggc agtcaagccg ccattcaccc gggcagcatc acggggcttt 20160
gtaagcgcat ggacgctgac gccgtgccga cccggggcga gacgattggg aagaaaaccg 20220
cttcaagcgc ctgggacccg gcaaccgtta tgcgaatcct tcgggacccg cgtattgcgg 20280
gcttcgccgc tgaggtgatc tacaagaaga agccggacgg cacgccgacc acgaagattg 20340
agggttaccg cattcagcgc gacccgatca cgctccggcc ggtcgagctt gattgcggac 20400
cgatcatcga gcccgctgag tggtatgagc ttcaggcgtg gttggacggc agggggcgcg 20460
gcaaggggct ttcccggggg caagccattc tgtccgccat ggacaagctg tactgcgagt 20520
gtggcgccgt catgacttcg aagcgcgggg aagaatcgat caaggactct taccgctgcc 20580
gtcgccggaa ggtggtcgac ccgtccgcac ctgggcagca cgaaggcacg tgcaacgtca 20640
gcatggcggc actcgacaag ttcgttgcgg aacgcatctt caacaagatc aggcacgccg 20700
aaggcgacga agagacgttg gcgcttctgt gggaagccgc ccgacgcttc ggcaagctca 20760
ctgaggcgcc tgagaagtcg ggcgaacggg cgaaccttgt tgcggagcgc gccgacgccc 20820
tgaacgccct tgaggagctg tacgaggacc gcgcggcagg cgcgtacgac ggacccgttg 20880
gcaggaagca cttccggaag caacaggcag cgctgacgct ccggcagcaa ggggcggagg 20940
agcggcttgc cgaacttgaa gccgccgaag ccccgaagct tccccttgac caatggttcc 21000
ccgaggacgc cgacgctgac ccgaccggcc ctaagtcgtg gtgggggcgc gcgtcagtag 21060

-continued

```
acgacaagcg cgtgttcgtc gggctgttcg tagacaagat cgttgtcacg aagtcgacta  21120

cgggcagggg ccagggtacc ccgatcgaga agcgggcctc catcacctgg gccaagccgc  21180

ccacggacga cgacgaggac gacgcccagg acggcacgga ggacgtagcg gcgtagcgag  21240

acacccggga agcctgatct acgtctgtcg agaagtttct gatcgaaaag ttcgacagcg  21300

tctccgacct gatgcagctc tcgcagggcg aagaatctcg tgctttcagc ttcgatgtag  21360

gagggcgtgg atatgtcctg cgggtaaata gctgcgccga tggtttctac aaagatcgtc  21420

cggcaaaaaa acgggcaagg tgtcaccacc ctgccctttt tctttaaaac cgaaaagatt  21480

acttcgcgtt tgccacctga cgtctaagaa aaggaatatt cagcaatttg cccgtgccga  21540

agaaaggccc acccgtgaag gtgagccagt gagttgattg ctacgtaatt agttagttag  21600

cccttagtga ctcgaagacc c                                           21621
```

RECOMBINANT CELLS AND METHODS FOR BIOSYNTHESIS OF ENT-ATISERENOIC ACID

CROSS-REFERENCE TO RELATED APPLICATION

This application claims priority to U.S. Provisional Patent Application No. 62/311,596, filed Mar. 22, 2016, which is incorporated herein by reference.

SEQUENCE LISTING

This application contains a Sequence Listing electronically submitted via EFS-Web to the United States Patent and Trademark Office as an ASCII text file entitled "11005390101_SequenceListing_ST25.txt" having a size of 76 kilobytes and created on Mar. 22, 2017. The information contained in the Sequence Listing is incorporated by reference herein.

SUMMARY

This disclosure describes recombinant cells and methods for microbial biosynthesis of ent-atiserenoic acid. Thus, in one aspect, this disclosure describes a recombinant cell genetically modified to exhibit increased biosynthesis of ent-atiserenoic acid compared to a comparable control cell. In some cases, the recombinant cell can include a host cell modified to include at least one heterologous polynucleotide encoding at least one enzyme in a biosynthetic pathway that produces ent-atiserenoic acid. In some cases, the recombinant cell can include a host cell and at least one heterologous enzyme in a biosynthetic pathway that produces ent-atiserenoic acid.

In some embodiments, the recombinant cell can be, or be derived from a *Streptomyces* spp. host cell.

In some embodiments, the comparable control cell comprises a wild-type cell that lacks the genetic modification that increases biosynthesis of ent-atiserenoic acid.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 22. Genotype of the full cluster constructs. P[#] means promoter and the number in the bracket indicates the expression strength. The higher the number, higher the expected expression is. RBS[#] is the ID of ribosomal binding sites. All RBS selected for this work are strong RBSs with different sequences. T[#] is the ID of transcriptional terminator used. All terminators are strong terminators with different sequences.

DETAILED DESCRIPTION OF ILLUSTRATIVE EMBODIMENTS

Figure 1:
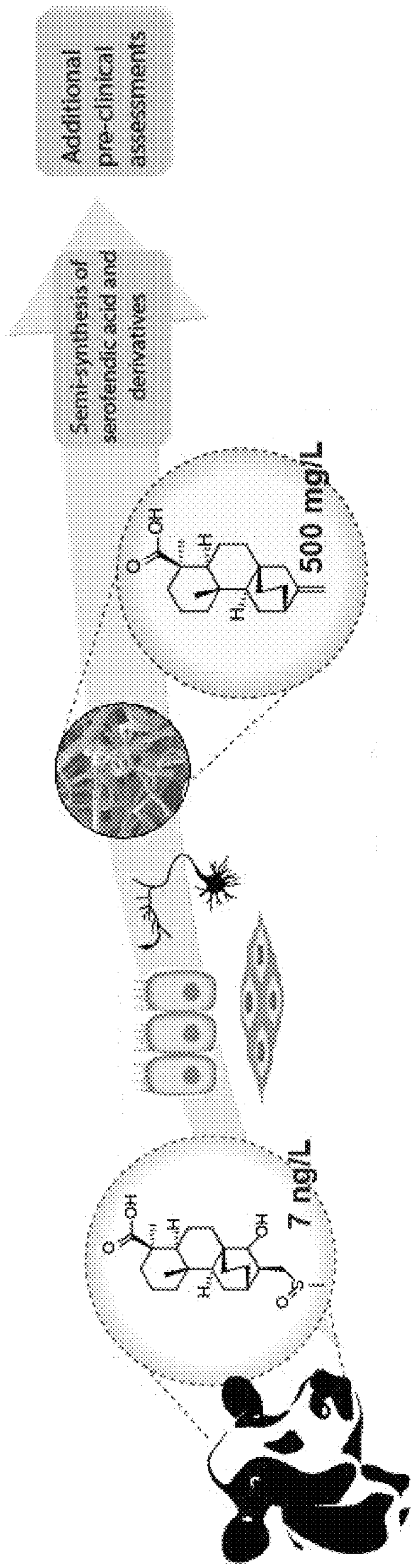
FIG. 1. Overview of serofendic acid discovery, bioactivity, and microbial method to enhance production titers for further drug-assessment.

This disclosure describes recombinant cells and methods for microbial production of ent-atiserenoic acid (eAA), which is used as a source for serofendic acid (SA) synthesis. Serofendic acid is an endogenous factor found in fetal calf serum (FCS) that exhibits activity decreasing damage to neurons from radical insults. Thus, this disclosure also describes a method of biosynthesizing ent-atiserenoic acid. Generally, the method includes culturing a recombinant cell genetically modified to exhibit increased biosynthesis of ent-atiserenoic acid. In some cases, the method can further include converting the ent-atiserenoic acid to serofendic acid.

Serofendic acid exhibits activity at concentration as low as 1 nM that decreases cytotoxicity induced by reactive oxygen species in nerve cell culture, cardiomyocte culture, epithelial cell culture, and animal models. However, further assessment is limited by the limited availability of serofendic acid. Currently, serofendic acid can be obtained by extracting the compound from fetal calf serum or de novo chemical synthesis. It requires as much as 250 L of fetal calf serum to isolate 1.5 mg serofendic acid. Chemical synthesis of serofendic acid includes more than 15 steps with a low yields. Thus, neither method is sustainable for serofendic acid production.

This disclosure describes microbial fermentation to biosynthesize ent-atiserenoic acid using a genetically-modified microbe. In one exemplary embodiment, a recombinant *Streptomyces* spp. strain in engineered to include coding regions of nine enzymes required to biosynthesize ent-atiserenoic acid. The exemplary engineered strain produced 40 mg/L ent-atiserenoic acid. The ent-atiserenoic acid isolated from microbial fermentation can be used to synthesize serofendic acid. Additional embodiments also are described.

While described herein in the context of an exemplary embodiment in which the recombinant cell is, or is derived from, a *Streptomyces* spp., the recombinant cells and methods described herein can involve the use of other host cells that can be transformed with heterologous nucleic acids and express heterologous polypeptides encoded by the heterologous nucleic acids. As used herein "derived from" in connection with a microbe simply allows for the host cell to possess one or more genetic modifications before being modified to exhibit increased biosynthesis of ent-atiserenoic acid. Thus, the term "recombinant cell" encompasses a "host cell" that may contain nucleic acid material from more than one species before being modified to exhibit ent-atiserenoic acid. In various alternative exemplary embodiments, the host cell can be, or be derived from, *Streptomyces coelicolor, Streptomyces* sp. GS-93, or *Streptomyces* sp. 3211.

Also, while described herein in the context of an exemplary embodiment in which a host cell is genetically modified to include particular heterologous polynucleotides that encode particular heterologous enzymes involved in the biosynthesis of ent-atiserenoic acid, the recombinant cells and methods described herein can involve the use of other polynucleotides and/or other enzymes that perform similar or identical functions to those expressly exemplified. Alternative heterologous polynucleotides and alternative heterologous enzymes include those that, when transformed into a host cell, cause the host cell to exhibit increased biosynthesis of ent-atiserenoic acid.

Figure 2:
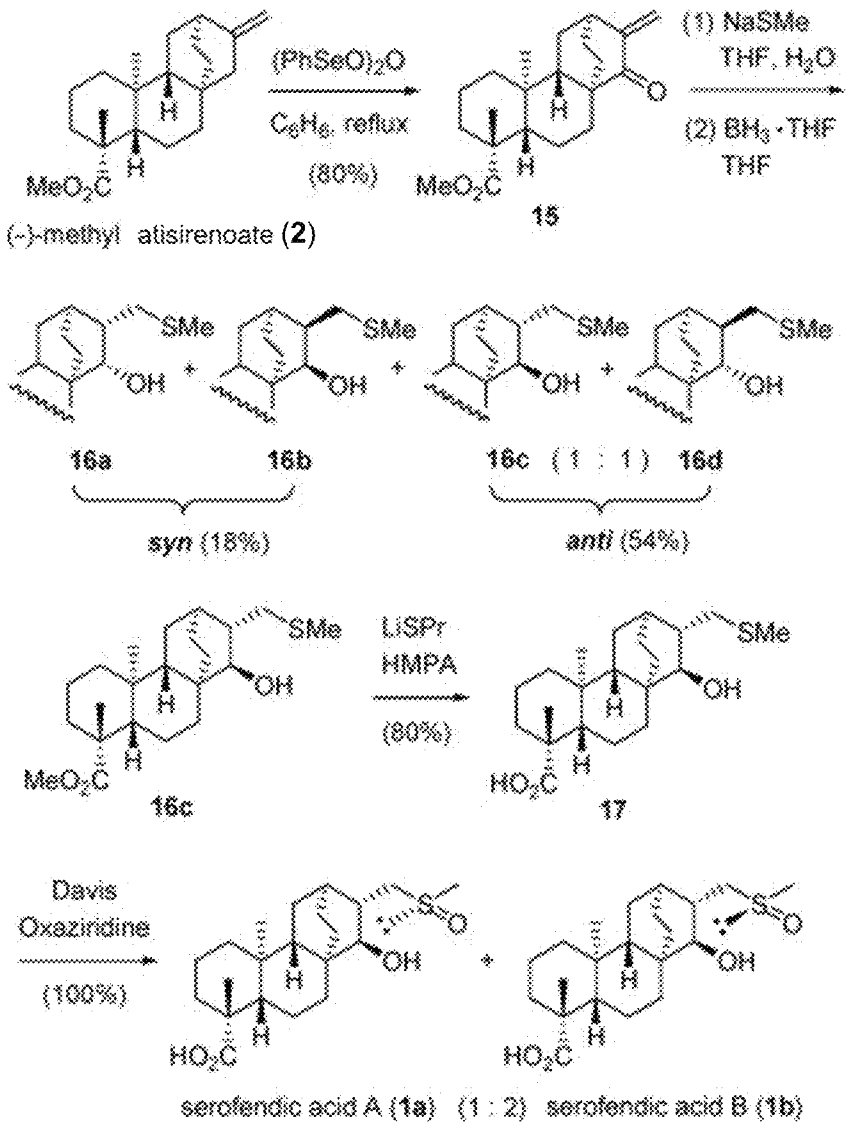
FIG. 2. The last four steps of total chemical synthesis of serofendic acid. The (−)-methyl atisirenoate (2) is the methylated analog of ent-atiserenoic acid.
Figure 3:
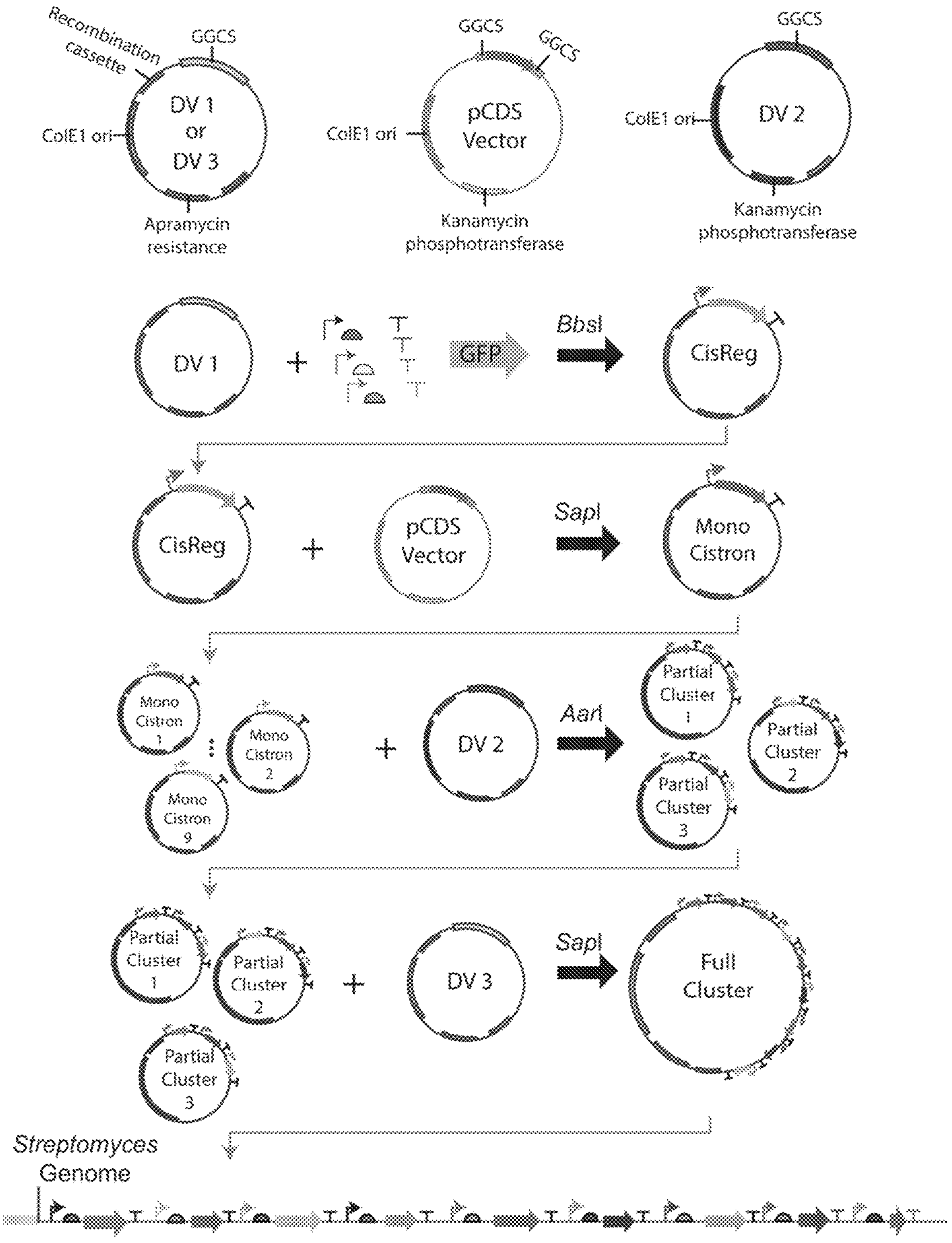
FIG. 3. Schematic diagram of the high-throughput assembly pipeline. Abbreviations: DV: destination vectors. GGCS: golden gate cloning sites. Cisreg is built by mixing promoters (colored arrows), ribosomal binding sites, terminators, coding sequence of egfp, and DVI for standard golden gate assembly using BbsI type IIS restriction enzyme. Monocistronic parts is built by mixing CisReg and pCDS containing desired gene for standard golden gate assembly using SapI type IIS restriction enzyme. Partial cluster is built by mixing monocistronic parts and destination vector 2 using AarI type IIS restriction enzyme in standard golden gate assembly. The full cluster is built by mixing partial clusters and destination vector 3 using SapI type IIS restriction enzyme in standard golden gate assembly. Finally, the full cluster in DV3, which is an integrative vector, can be introduced and integrated in *Streptomyces* genomes using standard conjugation protocol for heterologous expression.
Figure 4:
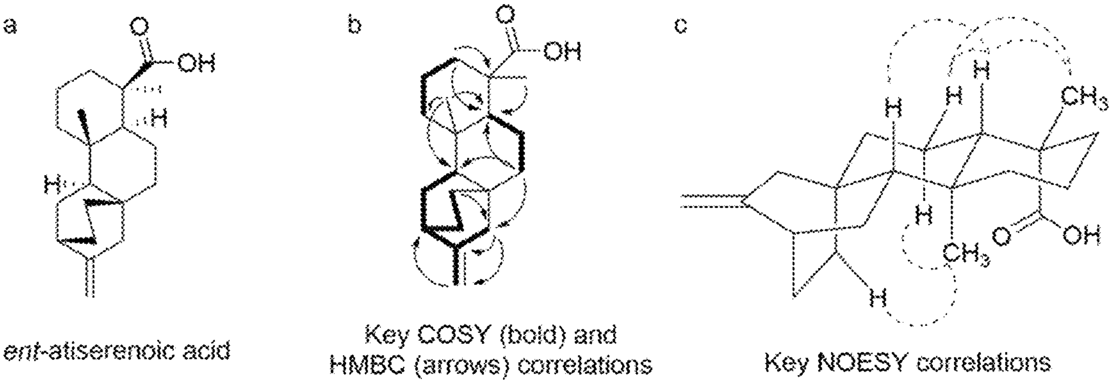
FIG. 4. Structure determination of ent-atiserenoic acid by 1 d and 2 d NMR.
Figure 5:
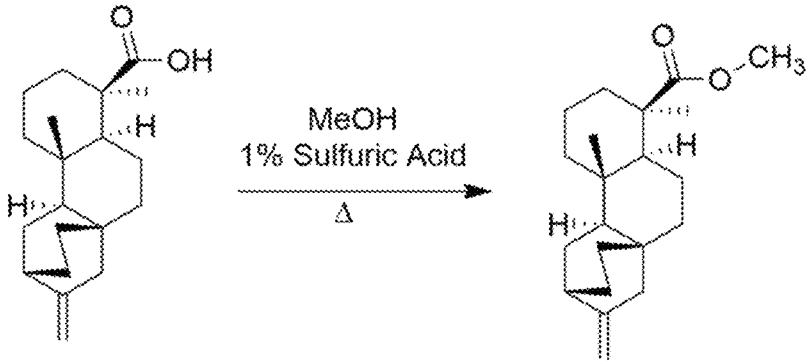
FIG. 5. Synthetic conversion of ent-atiserenoic acid to methylatiserenoate.
Figure 6:
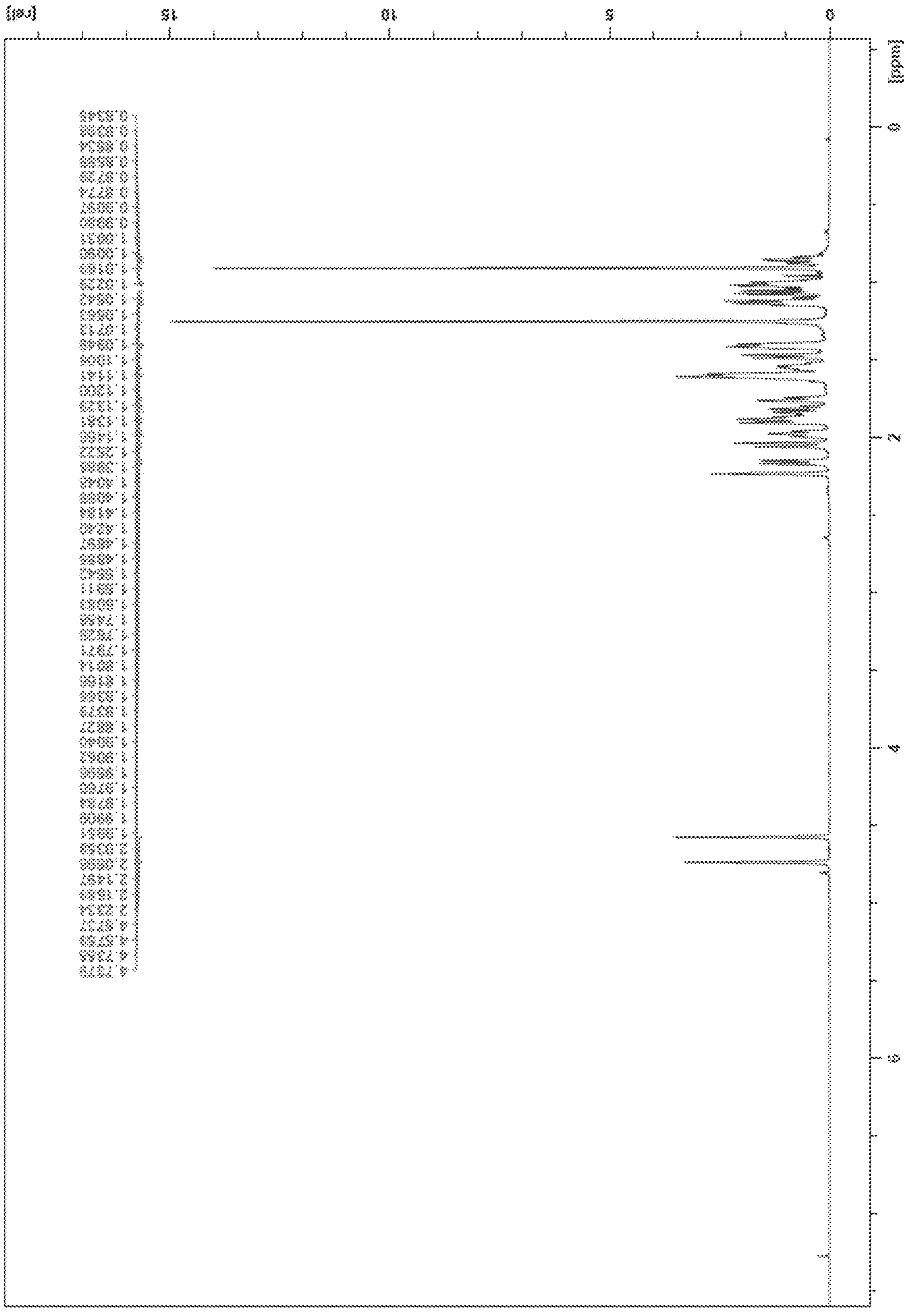
FIG. 6. ent-atiserenoic acid proton spectrum.
Figure 7:
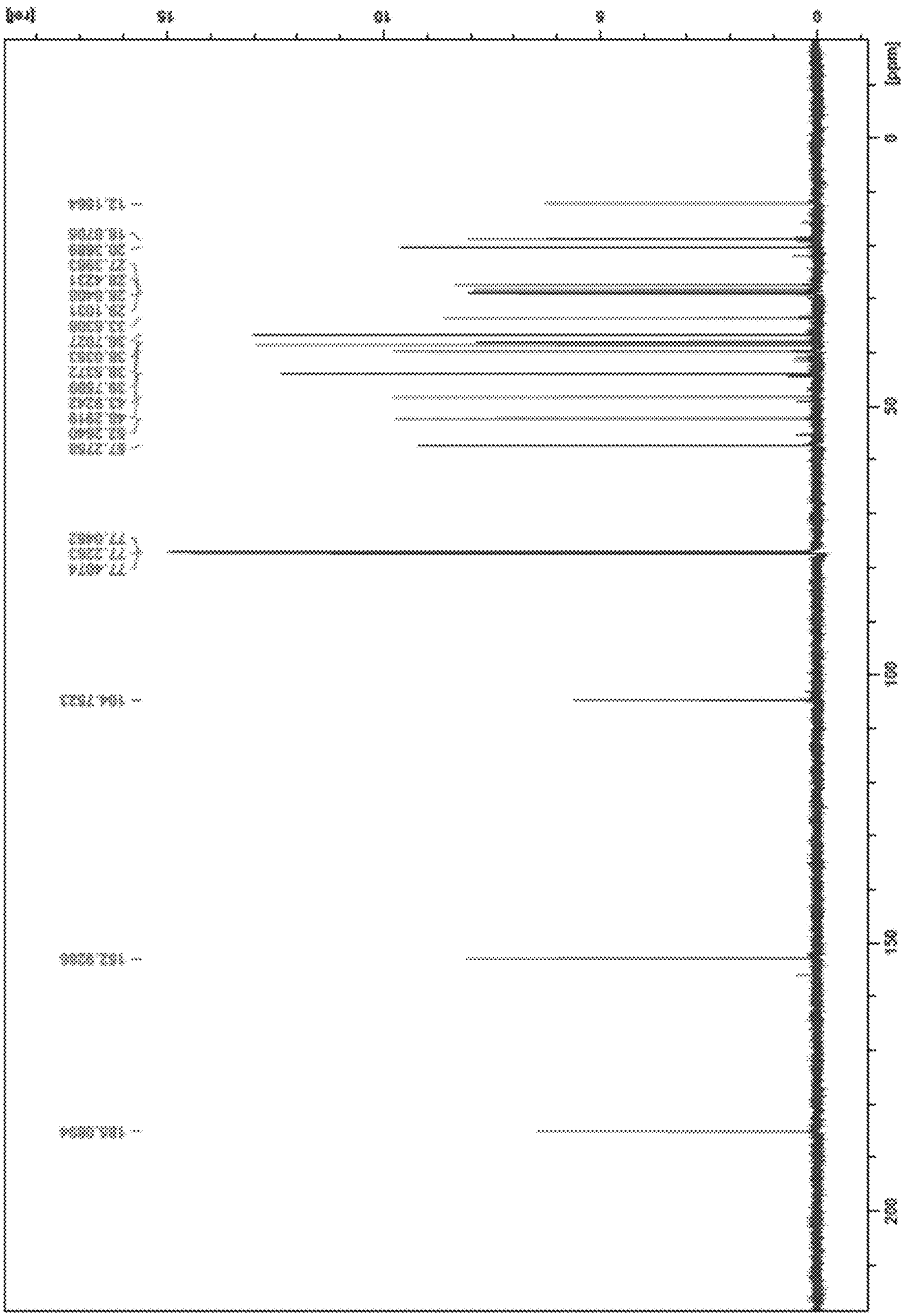
FIG. 7. ent-atiserenoic acid carbon spectrum.

Ent-atiserenoic acid (eAA) is a late stage intermediate in the synthesis of serofendic acid (SA). As shown in FIG. 2, methylatiserenoate (2) is the fourth to the last intermediate in final synthesis of serofendic acid. Microbial production of ent-atiserenoic acid enables a larger scale of serofendic acid semi-synthesis. Ent-atiserenoic acid is readily converted to 2 using solvolysis (FIG. 5). In certain embodiments, the production titer of ent-atiserenoic acid using microbial method can be as high as 500 mg/L, which can serve as an excellent source of precursors for serofendic acid synthesis and significantly reduce the steps and reagents required to produce serofendic acid.

Serofendic acid was originally isolated from the ether extract of fetal calf serum. While isolatable from fetal calf serum, serofendic acid is not detectable in adult bovine serum. The physiological concentration of serofendic acid is approximately in the tens of nanomolar level. The physiological role of serofendic acid is unclear.

Initial in vitro experiments showed serofendic acid protected cultured cortical neurons against acute glutamate neurotoxicity in a concentration-dependent and time-dependent manner at concentrations as low as 1 nM. The protective effect significantly increased when the cells were pretreated with serofendic acid for as short as 30 minutes prior to glutamate exposure.

Furthermore, serofendic acid decreased neurotoxic action of ionomycin, a calcium ionophore, and radical insults generated by NO and $H_2O_2$ donors. It was first speculated that the methylsulfoxide group of serofendic acid directly scavenges free radicals generated in neurotoxic events. However, it did not display direct radical scavenging activities against NO. In addition, serofendic acid does not directly inhibit glutamate receptors. Thus, serofendic acid may selectively attenuate toxicity without inhibiting the physiological roles of NO and glutamate receptors in signaling cascades.

Serofendic acid has also been tested in primary cultures of auditory neurons, astrocytes, cardiomyocytes as well as animal models of ischemic injuries. Serofendic acid is capable of protecting the cell types against oxidative stress-induced cell death. In vivo pharmacological studies indicated that serofendic acid afforded protection against cerebral ischemic-reperfusion injuries despite the low blood-brain barrier permeability (2.1 nmol/hour).

The activity of serofendic acid is still effective at the same level when RNA synthesis and de novo protein synthesis are inhibited. Without wishing to be bound by any particular theory or mechanism, these data suggest that serofendic acid's mode of action may be more likely to be mediated by protein interactions rather than transcriptional or translational regulations. Moreover, serofendic acid promotes neuron survival against neurotrophin deprivation, promotes stellation of astrocytes via cAMP-mediated and cGMP-mediated pathways, and inhibits TNF-α production in astrocytes. These observations revealed multifaceted effect of serofendic acid in promoting cell survival, but the underlying mechanisms were not entirely understood.

Current sources of serofendic acid are fetal calf serum and chemical synthesis. However, both sources are cost-prohibitive. 250 L of fetal calf serum are required to isolate 1.7 mg of serofendic acid. Moreover, harvesting fetal calf serum for biomedical research raises ethical questions. On the other hand, de novo chemical synthesis of serofendic acid requires more than steps with very low yield and thus requires much more initial precursors to generate sufficient amount of serofendic acid. Despite promising bioactivities of serofendic acid, the limited availability of serofendic acid has limited further therapeutic evaluation of serofendic acid.

This disclosure describes a microbial production source of ent-atiserenoic acid, a late intermediate that can be converted to serofendic acid and analogs. The microbial production of ent-atiserenoic acid allows for semi-synthesis of serofendic acid using ent-atiserenoic acid as a starting point for an abbreviated synthetic process compared to the current total synthesis process. Yield of serofendic acid is therefore increased because the microbial biosynthesis bypasses chemical synthesis steps that significantly decrease the final serofendic acid yield.

Figure 23:
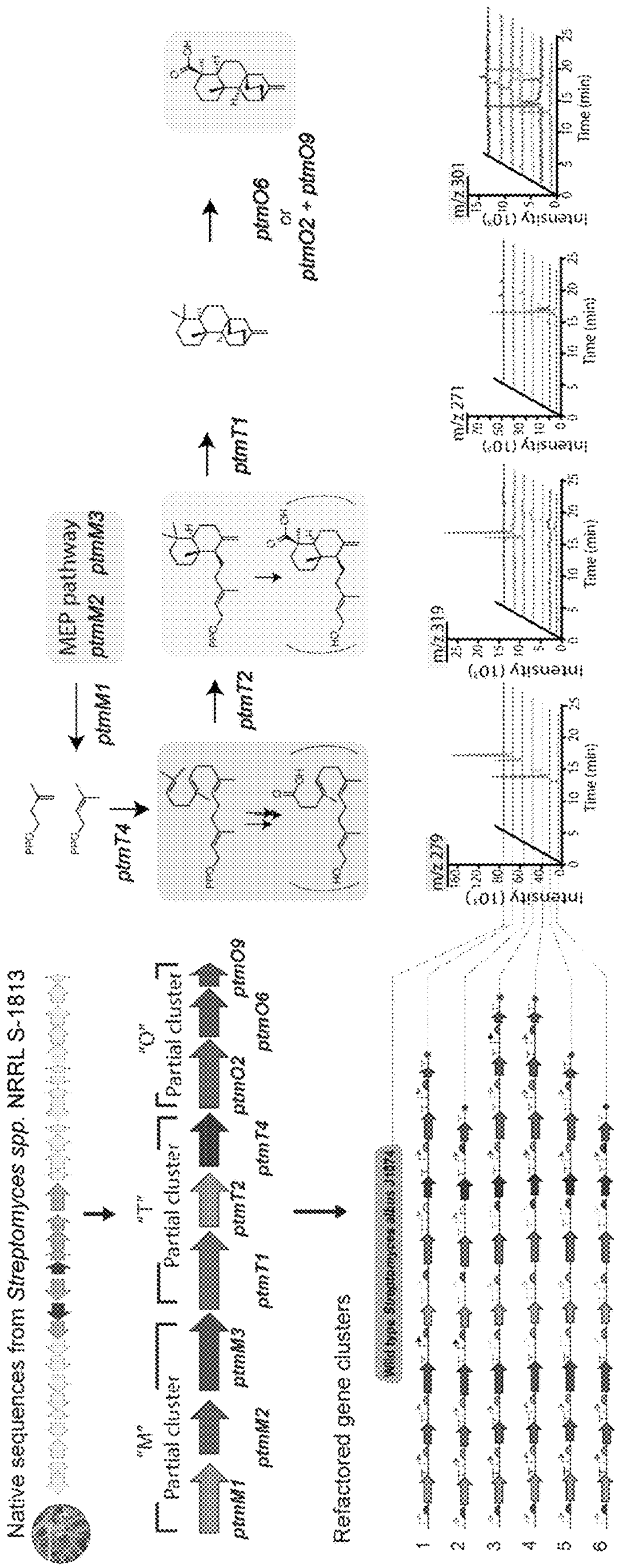
FIG. 23. Overview of six full cluster construct design (left) and the extracted ion chromatograms at m/z 279 (indicating the mass of ionized geranylgernyl diphosphate derivatives), 319 (indicating mass of ionized ent-copalol), 271 (indicating the mass of atiserene), and 301 (indicating the mass of eAA). The top right depicts the biosynthetic pathway of eAA reconstituted by nine-gene assembly of ptmM1, ptmM2, ptmM3, ptmT1, ptmT2, ptmT4, ptmO2 and ptmO9 and/or ptmO6.
Figure 24:
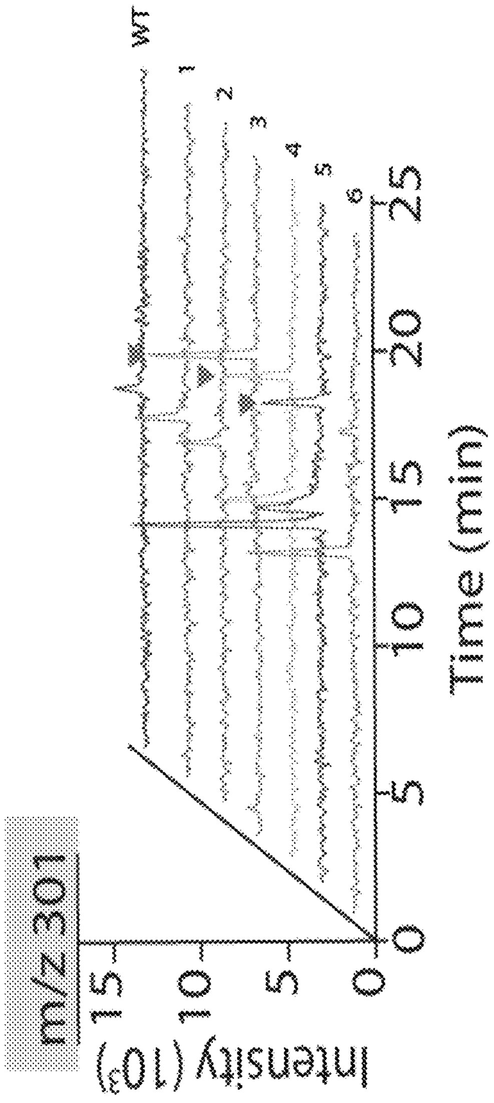
FIG. 24. Enlarged extracted ion chromatogram at m/z 301 value, the mass of negatively ionized ent-atiserenoic acid. Triangles indicate the ent-atiserenoic acid peak, which is unique in crude extracts from strain 3, 4, and 5. The retention time is ~16.5 minutes.
Figure 26:
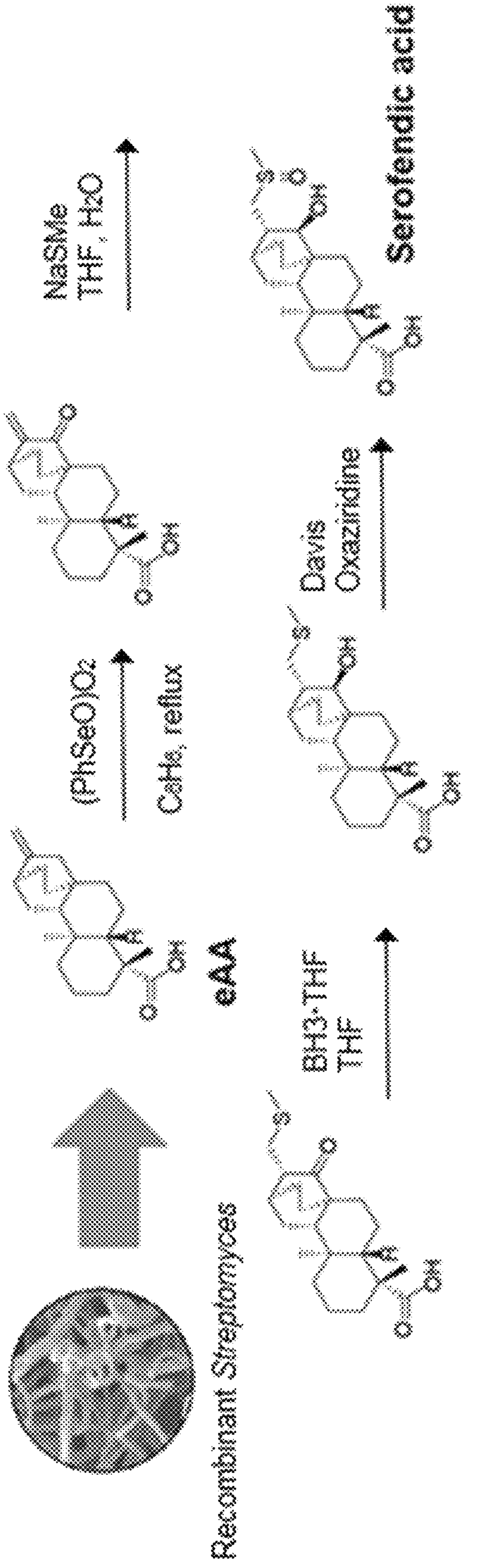
FIG. 26. Synthesis of serofendic acid from recombinantly-produced ent-atiserenoic acid.
Figure 25:
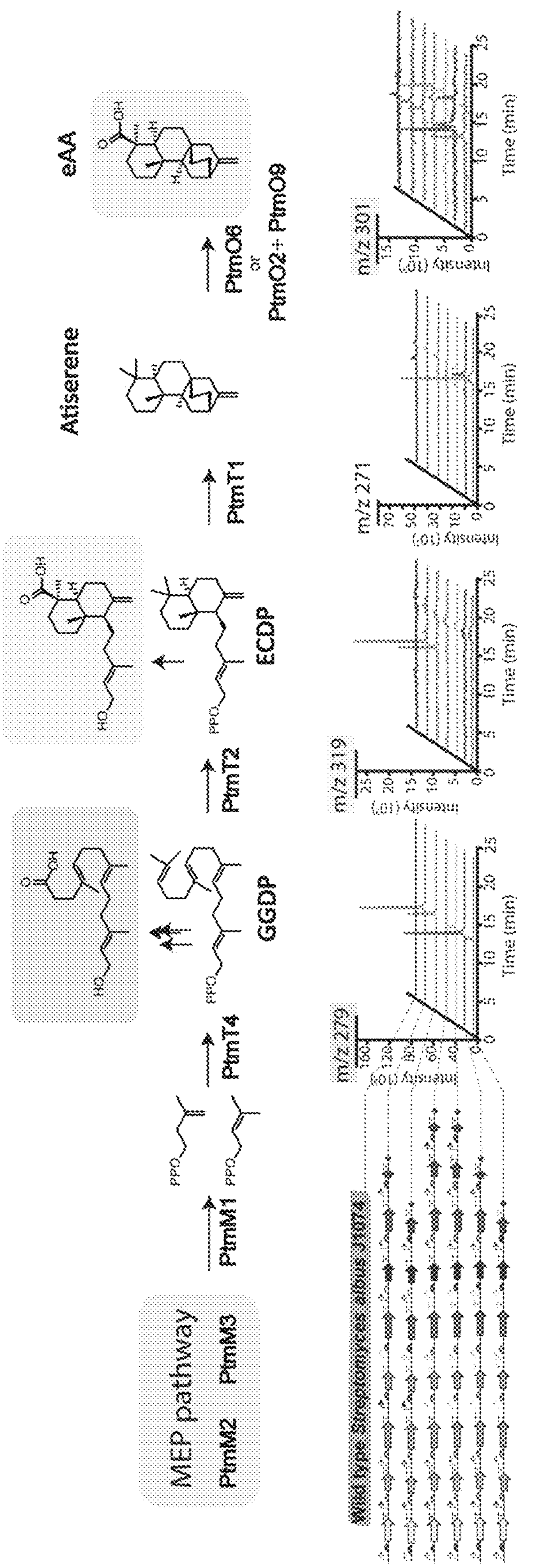
FIG. 25. Chemical structures of isolated metabolites and showing NMR correlations.

FIG. 22 and FIG. 23 show the construction of engineered recombinant cells. Six full clusters were conjugated in to *S. albus* J1074 and the crude extracts of the fermentation were analyzed by LC/MS. Three out of six strains (third, fourth, and fifth full cluster constructs) were observed to have unique peaks in extracted ion chromatogram of m/z 319 value (highlighted in green), which is the m/z value of ionized ent-atiserenoic acid. The retention time of ent-atiserenoic acid peak is approximately at 16.5 minutes (FIG. 22 and FIG. 23). FIG. 24 shows the ion chromatogram at m/z value of 301, the mass of negatively ionized ent-atiserenoic acid.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of Engineered Pathway for Ent-Atiserenoic Acid Biosynthesis

The genomic DNA of *Streptomyces* NRRL S-1813 was extracted using standard extraction methods. A total of nine coding regions encoding enzymes in a synthetic pathway for ent-atiserenoic acid biosynthetic were cloned using PCR amplification. The coding sequences (CDSs) of nine genes were ptmM1, ptmM2, ptmM3, ptmT2, ptmT4, ptmO2, ptmO6, and ptmO9. The primer sequences (Table 1) contained AarI restriction recognition sites to make the AarI site flanking the CDSs. The internal restriction sites of AarI and SapI Type IIS restriction enzymes were removed during cloning. Each coding region was cloned into cloning vector pCDS using standard AarI reaction. The sequence of all DNA constructs were verified using Sanger sequencing.

TABLE 1

Primer sequences used in this study.

| Primer | Sequence | SEQ ID NO |
|---|---|---|
| MSptmT1F | ATTACACCTGCTTATA ATGACGTCGGAACTGCCCGC | 1 |
| MSptmT1rrs1R | ATTACACCTGCTTAT GTGCCGCGCAcGTGAACGCGGTGCG | 2 |
| MSptmT1rrs1F | ATTACACCTGCTTAT GCACTGGAGATGGCGCTCGCCC | 3 |
| MSptmT1R | ATTACACCTGCTTATA TCAGAGCGCGAGCAGCGGGATG | 4 |
| MSptmO2F | ATTACACCTGCTTATA ATGACCACCCGCCCCACGGC | 5 |
| MSptmO2R | ATTACACCTGCTTATA TCATGCTGGACACTCGGTCAC | 6 |
| MSptmT2F | ATTACACCTGCTTATA ATGCTCGAAGTTCCCGCTCAG | 7 |
| MSptmT2R | ATTACACCTGCTTATA TCAAGCACCTCCGGAAGCGGC | 8 |
| MSptmO6F | ATTACACCTGCTTATA ATGTGGGAGCCGACGTCTGC | 9 |
| MSptmO6R | ATTACACCTGCTTATA TCACGCGGCGGTGTTCTGCTG | 10 |
| MSptmT4F | ATTACACCTGCTTATA ATGCACGCTGACACAGTCCAG | 11 |
| MSptmT4rrs1R | ATTACACCTGCTTAT CGACGGGAATGgaCTTCTTCTTGTTGTG | 12 |
| MSptmT4rrs1F | ATTACACCTGCTTAT GTCGTCGCCGCCCTCCACAGC | 13 |
| MSptmT4R | ATTACACCTGCTTATA TCAGTGCTTCCTGAAGGCGAC | 14 |
| MSptmM1F | ATTACACCTGCTTATA ATGACCGCCGCCATCGTGAG | 15 |
| MSptmM1R | ATTACACCTGCTTATA TCAACAGCTGTCAACGGTCTTC | 16 |
| MSptmM2F | ATTACACCTGCTTATA ATGCCGACGACACCGCTGCG | 17 |
| MSptmM2rrs1R | ATTACACCTGCTTAT GTGCTCCGCGAAcAGCTCCGCCTC | 18 |
| MSptmM2rrs1F | ATTACACCTGCTTAT GCACGACTTCCACGACTTCAAG | 19 |
| MSptmM2R | ATTACACCTGCTTATA TCAGCCAGTCTCATCGAGGTC | 20 |
| MSptmM3F | ATTACACCTGCTTATA ATGAGACTGGCTGACCTCAC | 21 |
| MSptmM3rrs1R | ATTACACCTGCTTAT GTGGCCGGTGTCGAAcAGCAGGGTG | 22 |
| MSptmM3rrs1F | ATTACACCTGCTTAT CCACCAGGCCTACGTCCACAAG | 23 |
| MSptmM3R | ATTACACCTGCTTATA TCAGCGcGGGGCCGCTTGTG | 24 |
| MSptmT2nestF | GGCTCCCACACCAGCCCAGCCACCAGCCAG | 25 |
| MSptmT2nestR | CATCGAGGGGCATGGGAAGGCCTTCTG | 26 |

TABLE 1-continued

Primer sequences used in this study.

| Primer | Sequence | SEQ ID NO |
|---|---|---|
| MSptmo9F | ATTACACCTGCTTATA ATGACGTACGTAATCGCGCAGC | 27 |
| MSptmO9R | ATTACACCTGCTTATA TCATTCGCCCGCGGCTCCGGCC | 28 |

CisREG and Monocistron Construction.

A library of CisREG cloning vectors that each contained a promoter, a ribosomal binding site, eGPF CDS, and a transcriptional terminator was assembled using BbsI type IIS assembly, PRC, and ligation. Then, the monocistrons were built using standard SapI Type IIS assembly reaction. Briefly, individual coding regions in the pCDS were mixed with equimolar of CisREG, with 10 U of T4 ligase and SapI restriction enzyme. The reaction was cycled between 37° C. and 16° C. for at least two hours, with last step of heat-inactivating the enzymes for 10 minutes. The CisTRON parts were transformed into *E. coli* DH5alpha and plated on an apramycin plate. The clones were verified using colony PCR with gene specific primers.

Partial Cluster Assembly.

Standard AarI type IIS assembly was used to construct a partial cluster from one, two, or three monocistronic parts. A total of three libraries of partial clusters (termed "M" clusters, "T" clusters, and "0" clusters) were assembled. The partial cluster constructs were transformed into *E. coli* DHSalpha and plated on a kanamycin plate. The clones were verified using colony PCR with gene specific primers Full Cluster Assembly.

Full clusters were assembled using standard SapI type IIS assembly from libraries of three partial clusters. The full cluster constructs were transformed into *E. coli* DH5alpha and plated on apramycin plate. The clones were verified using colony PCR with gene specific primers Heterologous Production in *S. albus* J1074 with Isolated Yields of 45 mg/L

*Streptomyces* Conjugation.

A total of eight full clusters were assembled and conjugated into *Streptomyces* using standard protocol. Briefly, individual full clusters were transformed into *E. coli* conjugation donor strain ET 12567 [pUCZS002]. Individual colonies were verified using colony PCR. Successful transformants were grown to confluence in 2 mL overnight cultures supplemented with apramycin. Frozen spore stock of *S. albus* J1074 were quickly thawed, heat shocked at 50° C. for 10 minutes, supplemented with TSB medium with 10% sucrose, and incubated in 30° C. shaker for at least two hours. In the meantime, the *E. coli* donor strain containing the full cluster was washed with LB+20 mM magnesium chloride two times to remove antibiotics. After final centrifugation, the cell pellet was resuspended with 500 L of the *Streptomyces* germinated spore solution. The *Streptomyces-E. coli* solution was spotted on IWL-4 plates supplemented with 20 mM magnesium chloride, and dried completely over the surface. The plates were incubated overnight at 30° C. On the following day, the spot of *Streptomyces-E. coli* mixture was re-streaked on IWL-4 plates with 25 μg/mL nalidixic acid and 50 μg/mL apramycin plate to obtain single *Streptomyces* exconjugants. The plates were incubated for two to three days or until colonies appeared on the plate. The exconjugants were verified with colony PCR with gene-specific primers.

Small Scale Fermentation.

The exconjugants were grown in 3 mL seed culture in R2YE supplemented with apramycin at 30° C. shaker for 2-3 days. Once the culture reached confluence, 1:100 inoculation of each exconjugant was performed to start 3 mL seed cultures in ISM-3 medium supplemented with apramycin, incubating in 30° C. shaker for 2-3 days or until reached confluence. The ISM-3 seed cultures were used to inoculate 50 mL PCNM media (6 g/L yeast extract, 15 g/L malt extract, 6 g/L dextrose, 20 g/L MOPS sodium salt, 5 mL trace elements) with 1.5 g amberlite resin in 250 mL baffled flask. The fermentations were incubated in 30° C. shaker for 10 days.

Two-Liter Fermentation of Strain #4.

Single colonies of exconjugant containing #4 full cluster (strain 4) were grown in 3 mL seed culture in R2YE medium (Shepherd et al., 2010, *Curr Protoc Microbiol. CHAPTER*, Unit-10E.1. http://doi.org/10.1002/9780471729259.mc10e01s18) supplemented with apramycin at 30° C. shaker for 2-3 days. Once the culture reached confluence, 3 mL seed cultures in ISM-3 medium (15 g/L yeast extract, 10 g/L malt extract, 0.244 g/L $MgSO_4$, 0.3 g/L $FeCl_3.6H_2O$, 20 g/L dextrose, pH 7.0) supplemented with apramycin were started by 1:100 inoculation from R2YE cultures and incubated in 30° C. shaker for 2-3 days or until reached confluence. The ISM-3 seed cultures were used to inoculate four 500 mL PCNM media with 15 g amberlite resin in two-liter baffled flasks. The fermentations were incubated in 30° C. shaker for 10 days.

Solid-Liquid Extraction.

The fermentations were poured into 50 mL conical tubes and centrifuged. The supernatants were saved in another 50 mL conical tube for later analysis. The resin and the cell pellets of the fermentation were washed with $ddH_2O$ three times. After the final centrifugation, the water was removed from the resin as much as possible, frozen at −80° C., and lyophilized overnight. Once the resin and the cell pellet were freeze-dried, they were extracted with 10 mL methanol for three times. The methanol extracts were dried down using vacuum distillation. The final samples were resuspended in 1 mL methanol to obtain concentrated extracts.

Purification of Ent-Atiserenoic Acid.

The concentrated extracts were subjected to column chromatography using silica gel as the solid phase, and a mixture of chloroform and methanol as the mobile phase. The samples were fractionated and each fraction was analyzed by TLC. The fractions containing compound with similar $R_f$ value to ent-atiserenoic acid were combined and dried down using vacuum distillation. The dried compounds were weighed and resuspended in 1-5 mL of methanol. The structure of eAA was further analyzed using NMR.

LC/MS Analysis.

The injection samples were prepared by diluting each concentrated extracts 100-fold in methanol (10 μL concentrated extract in 990 μL methanol). The dilution samples were centrifuged in max speed, and the supernatants were transferred to LC/MS capped glass vials. The LC/MS buffer system used was 100% acetonitrile and 0.1% formic acid. The other buffer system was 100% acetonitrile and 10 mM ammonium formate (pH 8.3). The instrument used was plus single quadrupole Mass spectrometer. The total negative ion chromatogram was collected and analyzed in DIONEX Chromeleon Chromatography Data System (CDS) software, version 7.

Structure Determination of Ent-Atiserenoic Acid by NMR Spectroscopy

Figure 8:
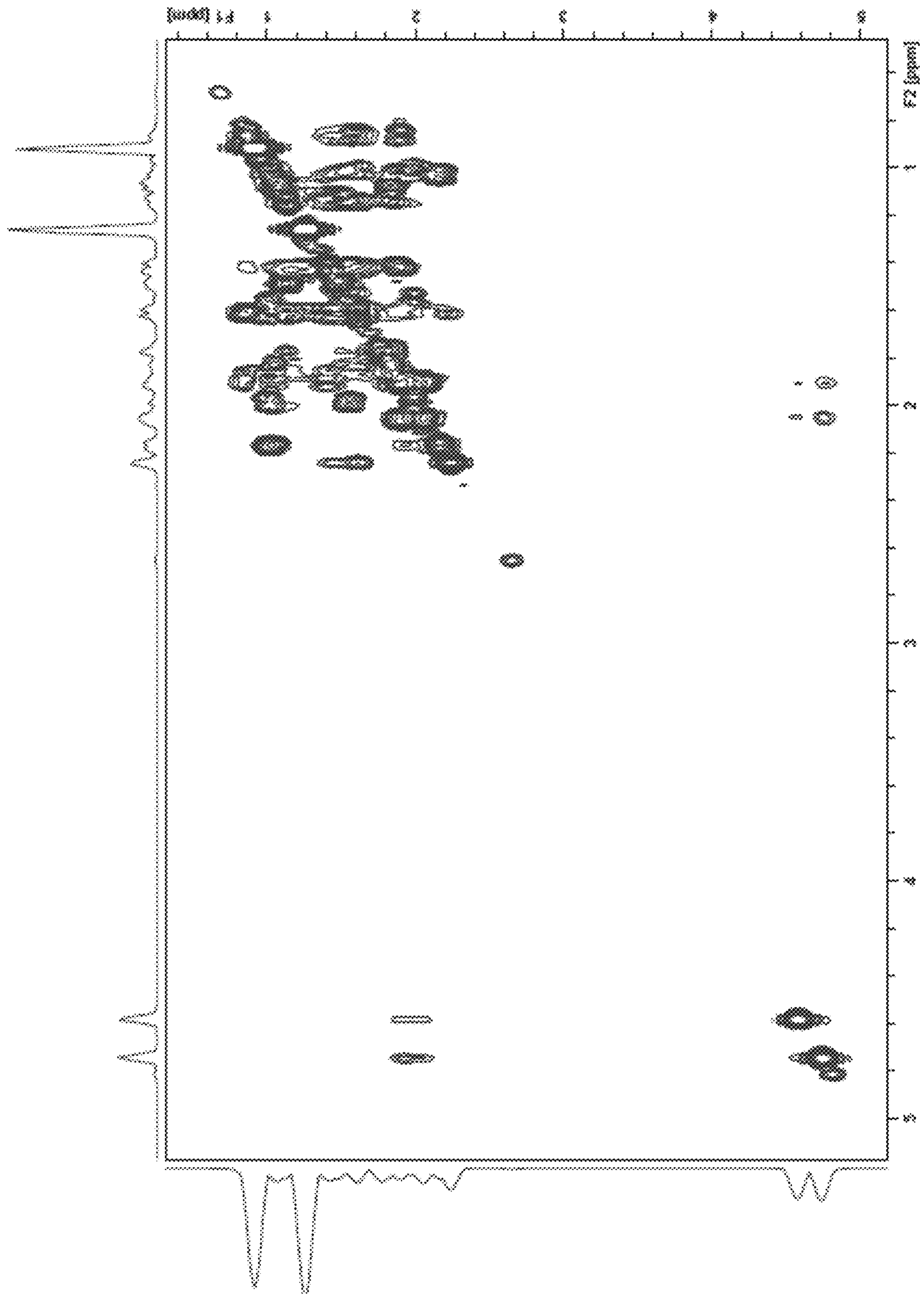
FIG. 8. ent-atiserenoic acid COSY spectrum.
Figure 9:
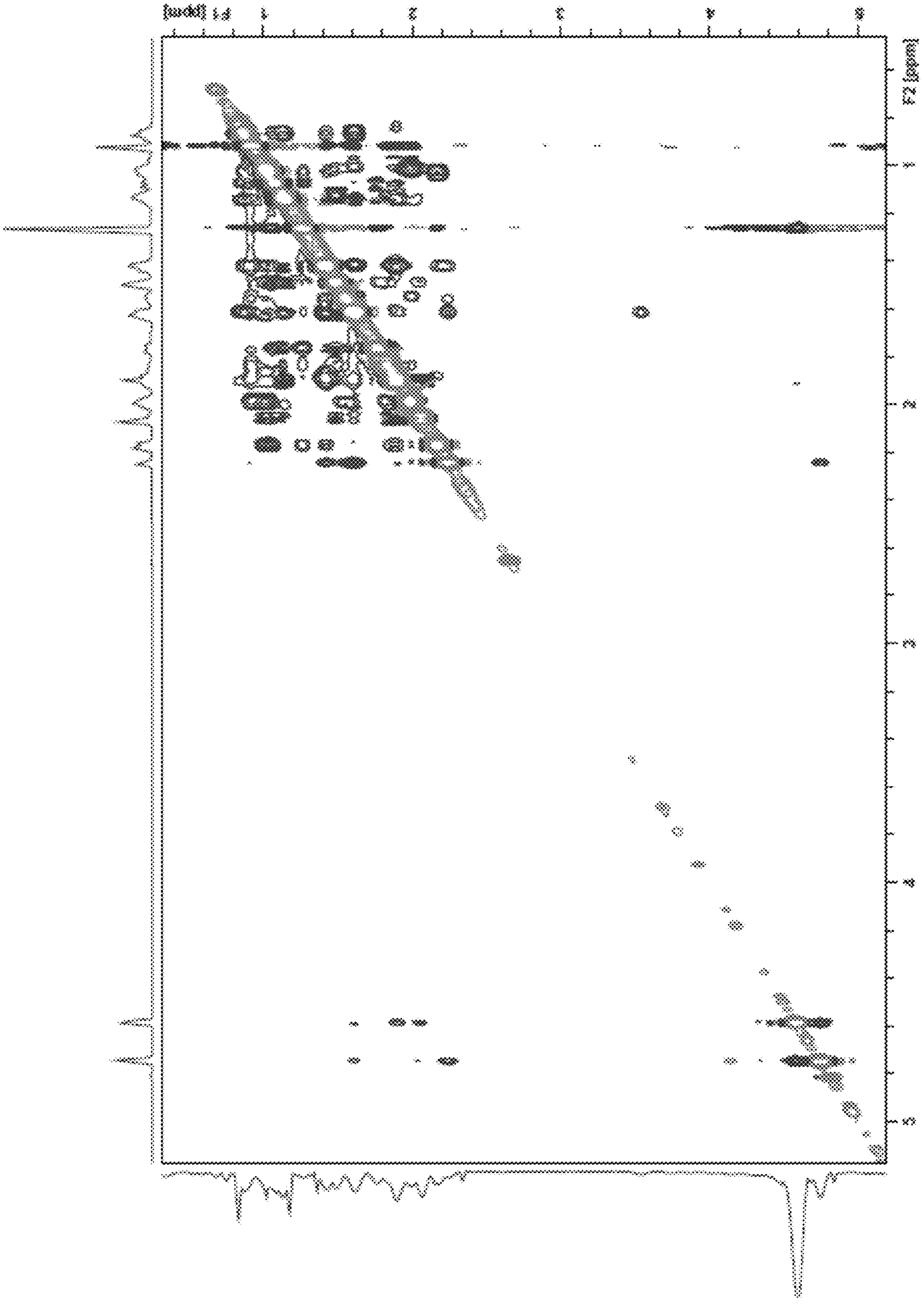
FIG. 9. ent-atiserenoic acid NOESY spectrum.
Figure 10:
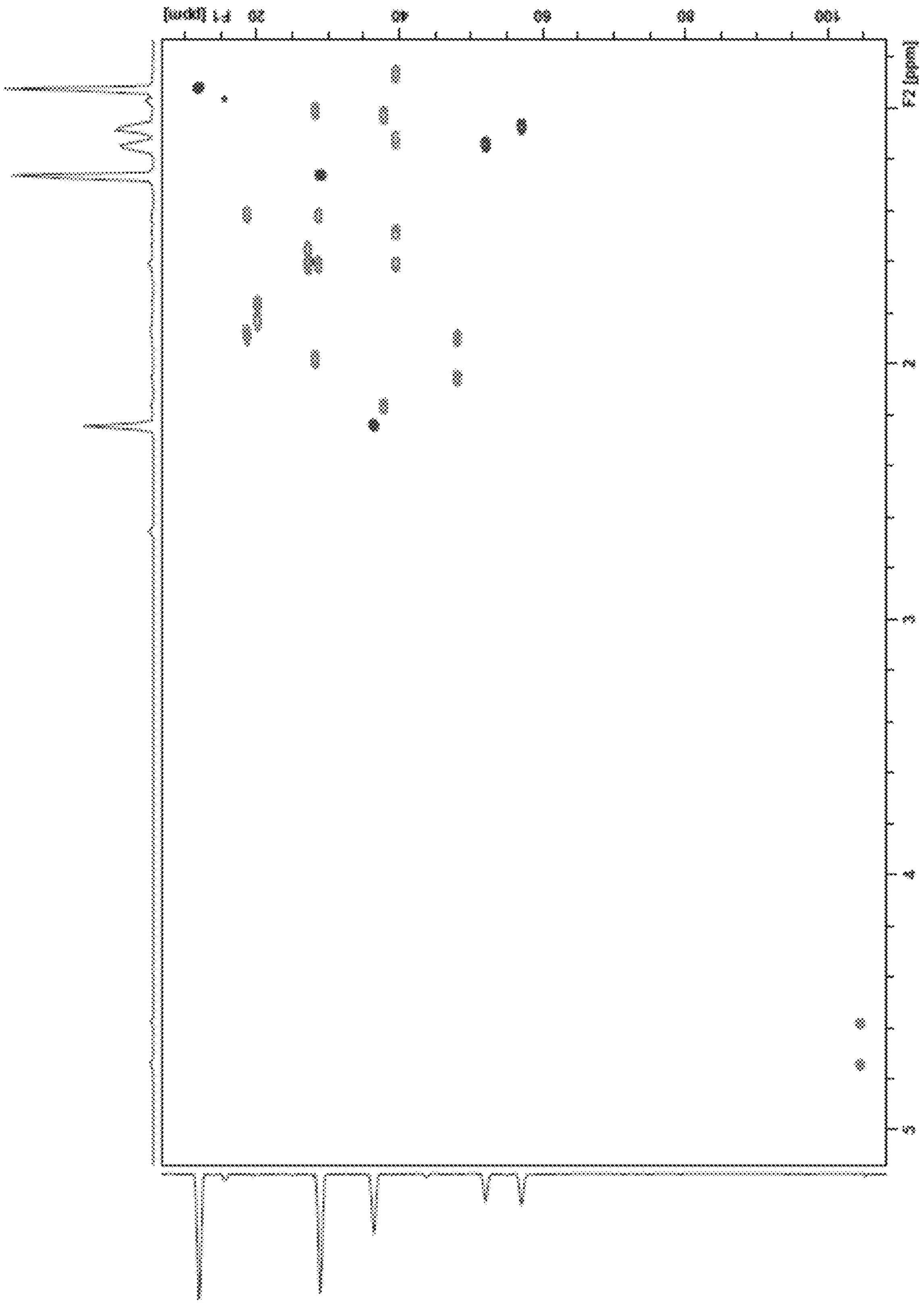
FIG. 10. ent-atiserenoic acid HSQC spectrum.
Figure 11:
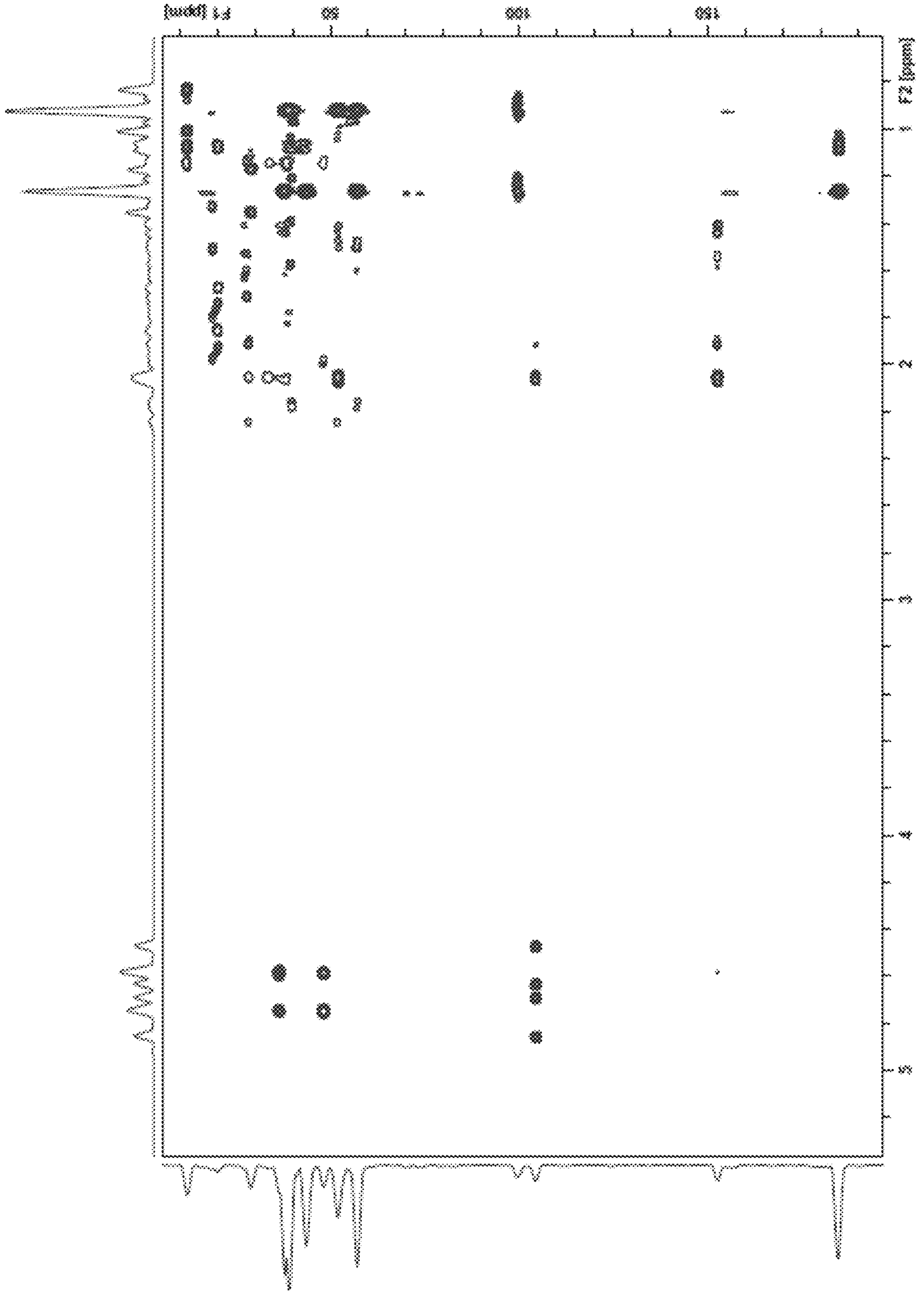
FIG. 11. ent-atiserenoic acid HMBC spectrum.
Figure 12:
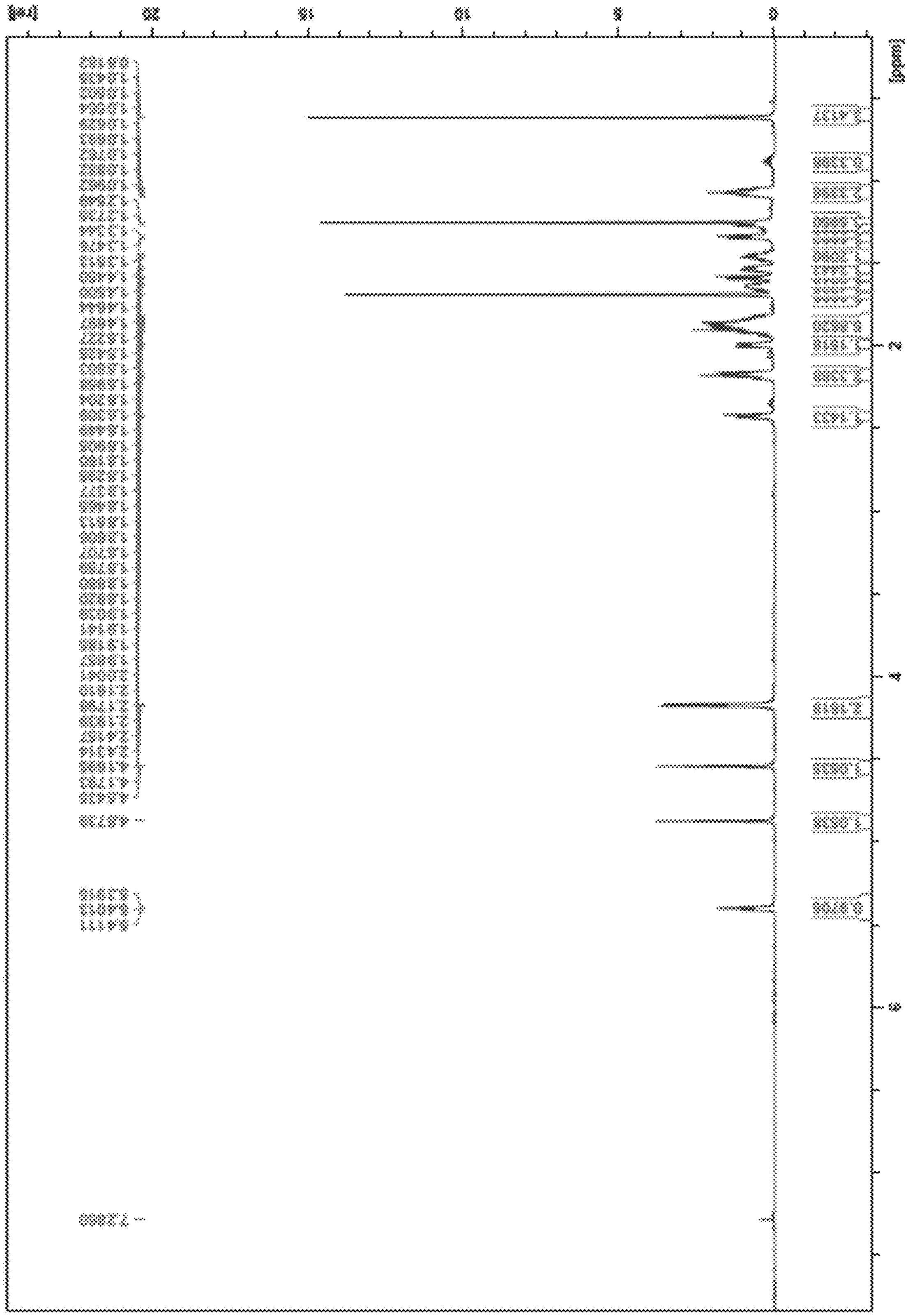
FIG. 12. SH-c proton spectrum.
Figure 13:
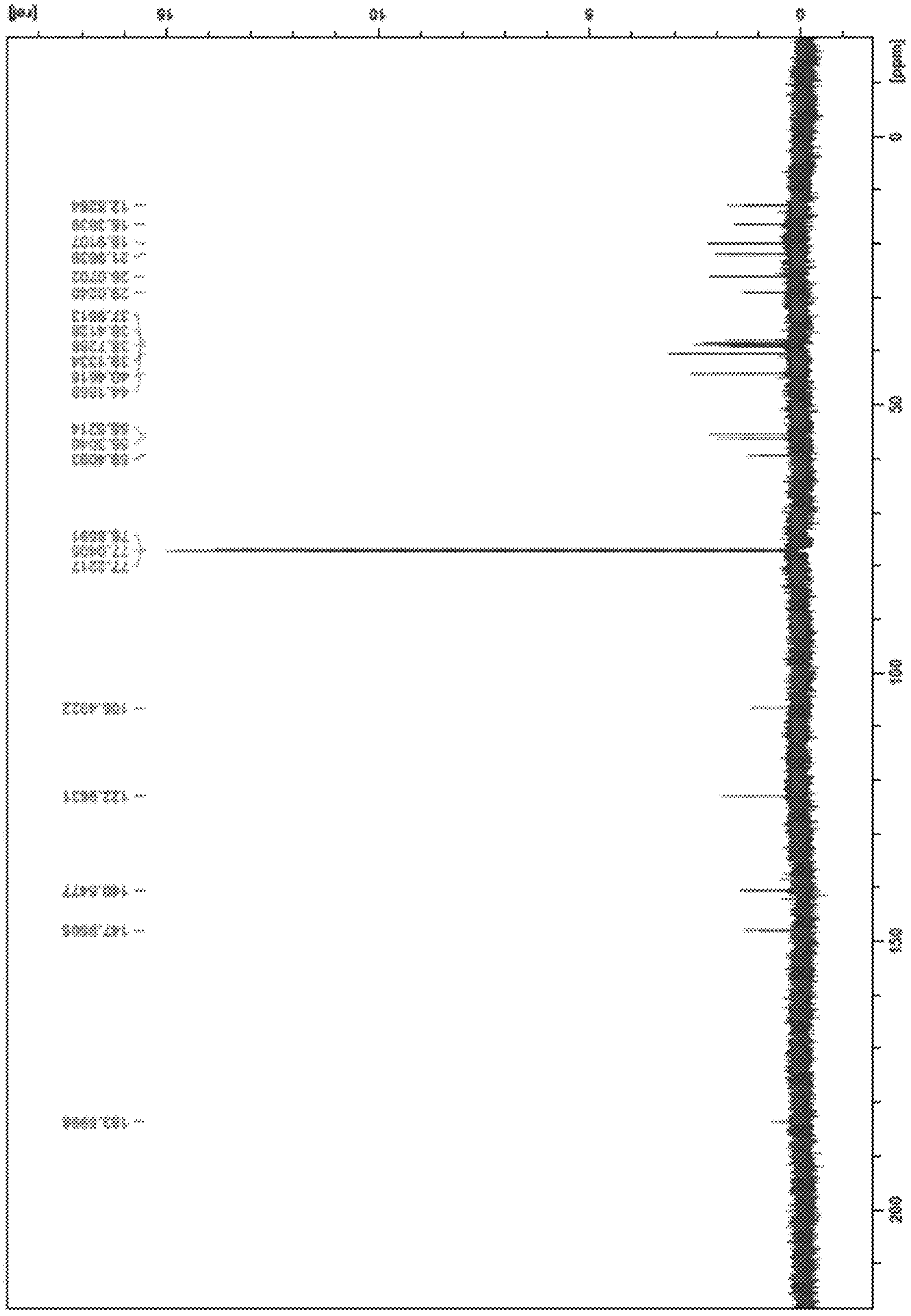
FIG. 13. SH-c carbon spectrum.
Figure 14:
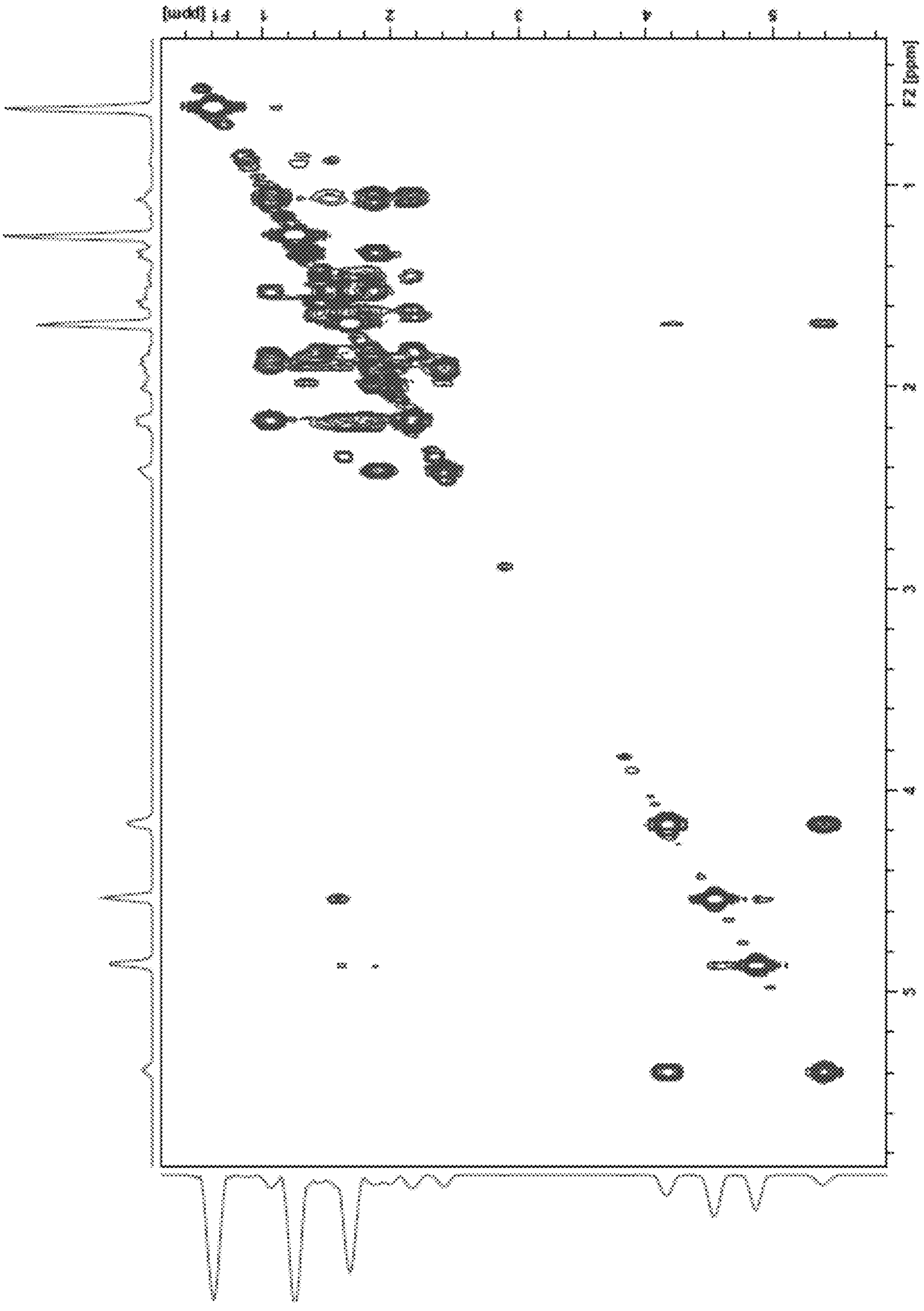
FIG. 14. SH-C COSY spectrum.
Figure 15:
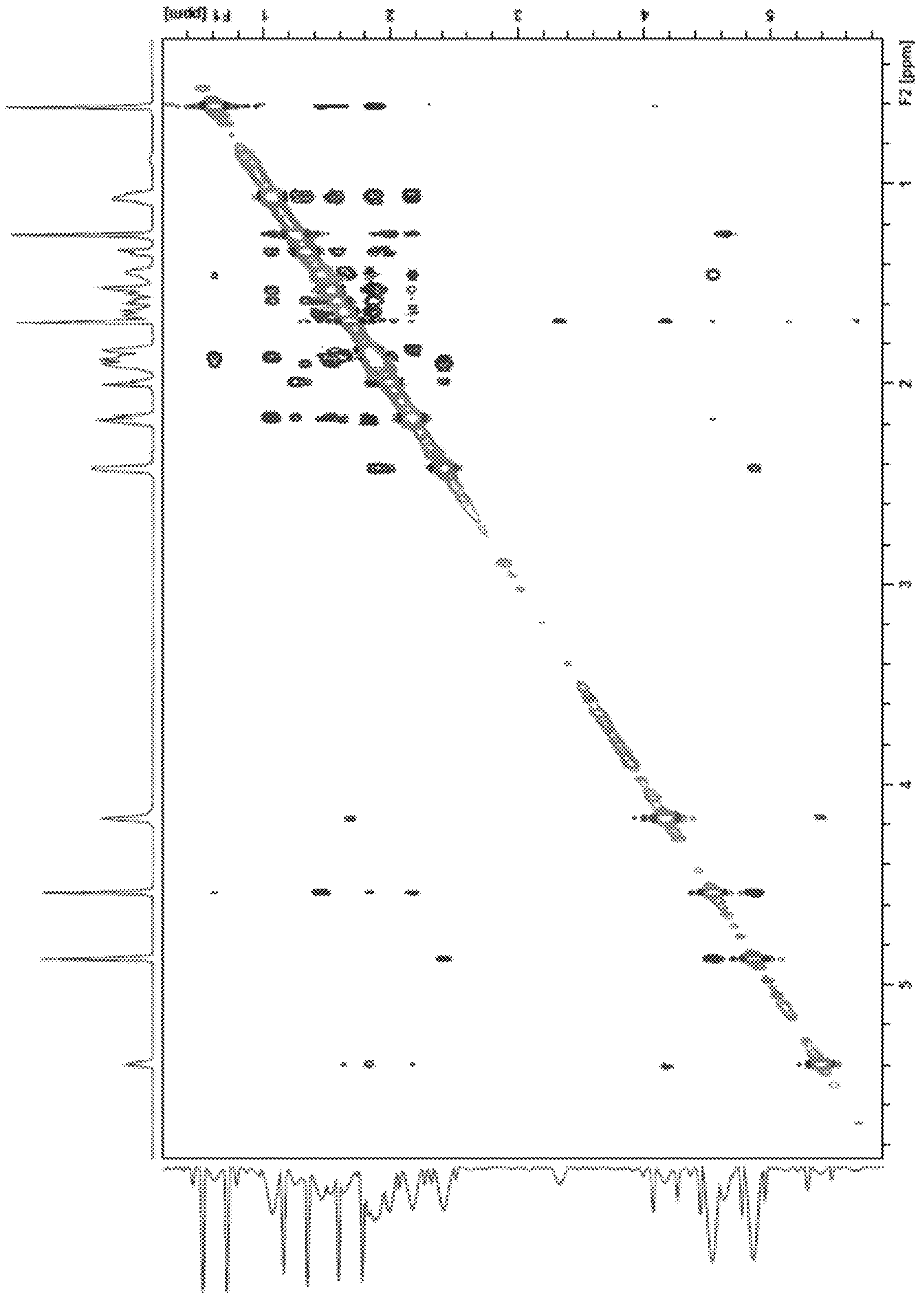
FIG. 15. SH-c NOESY spectrum.
Figure 16:
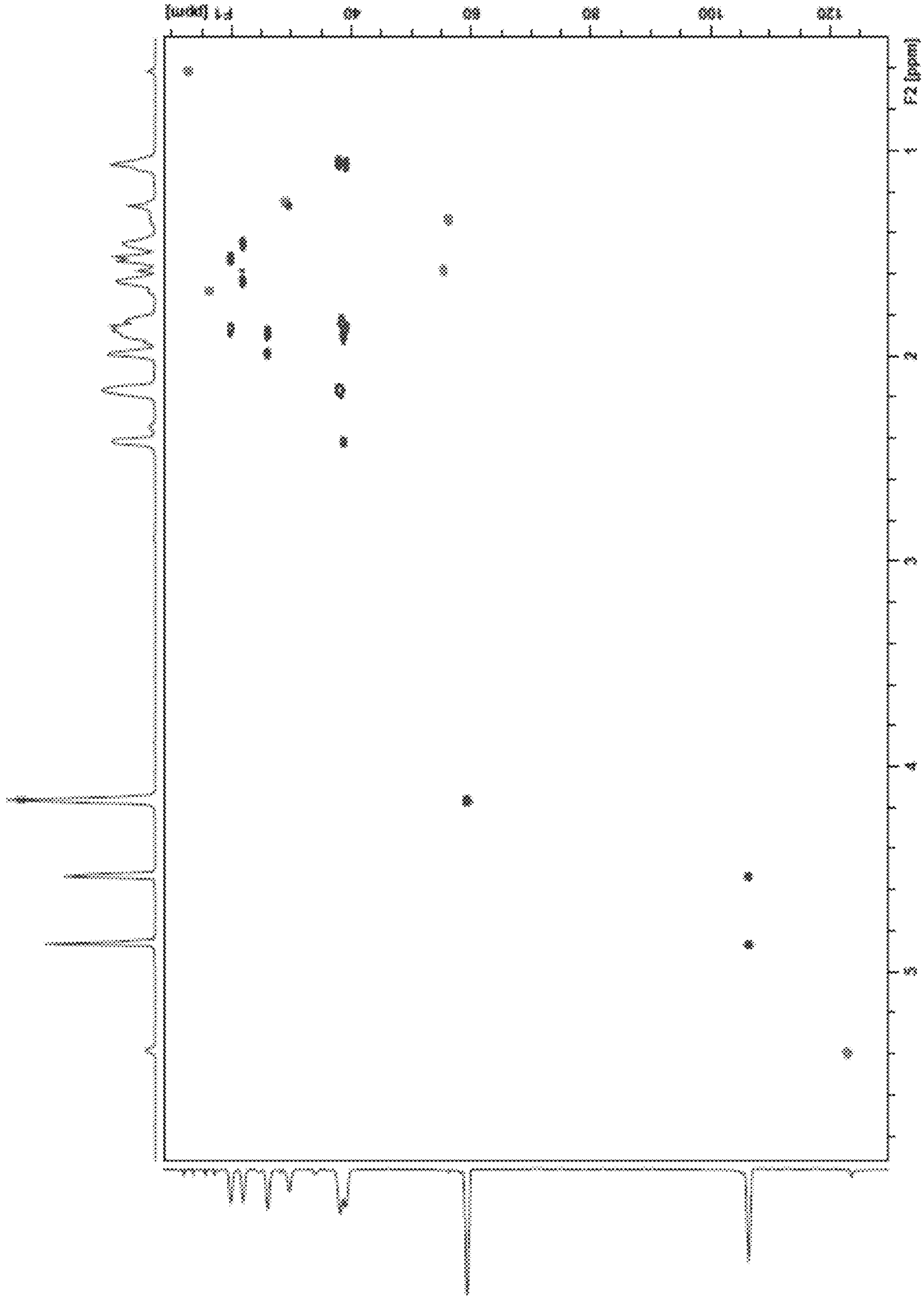
FIG. 16. SH-C HSQC spectrum
Figure 17:
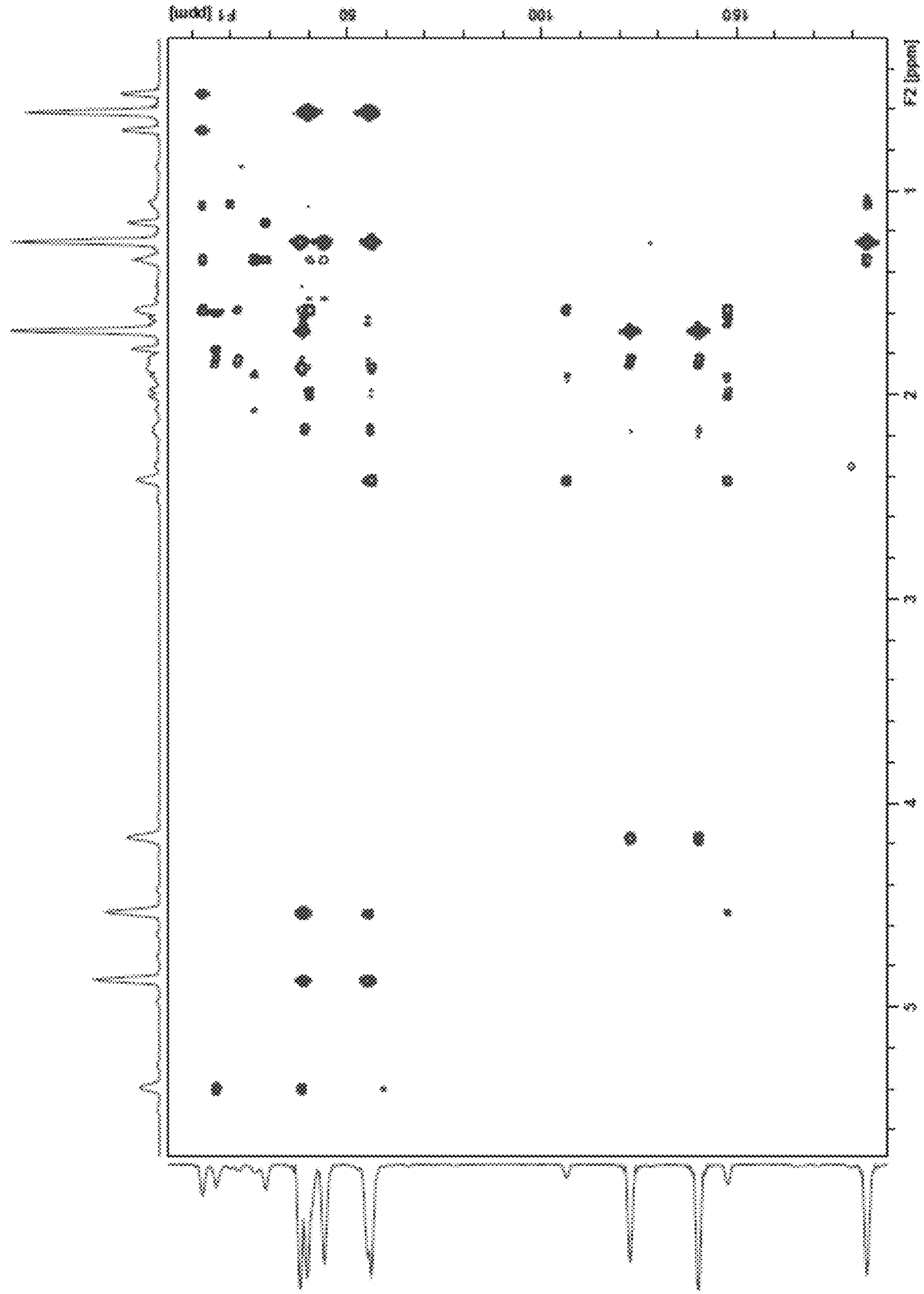
FIG. 17. SH-c HSQC spectrum.
Figure 18:
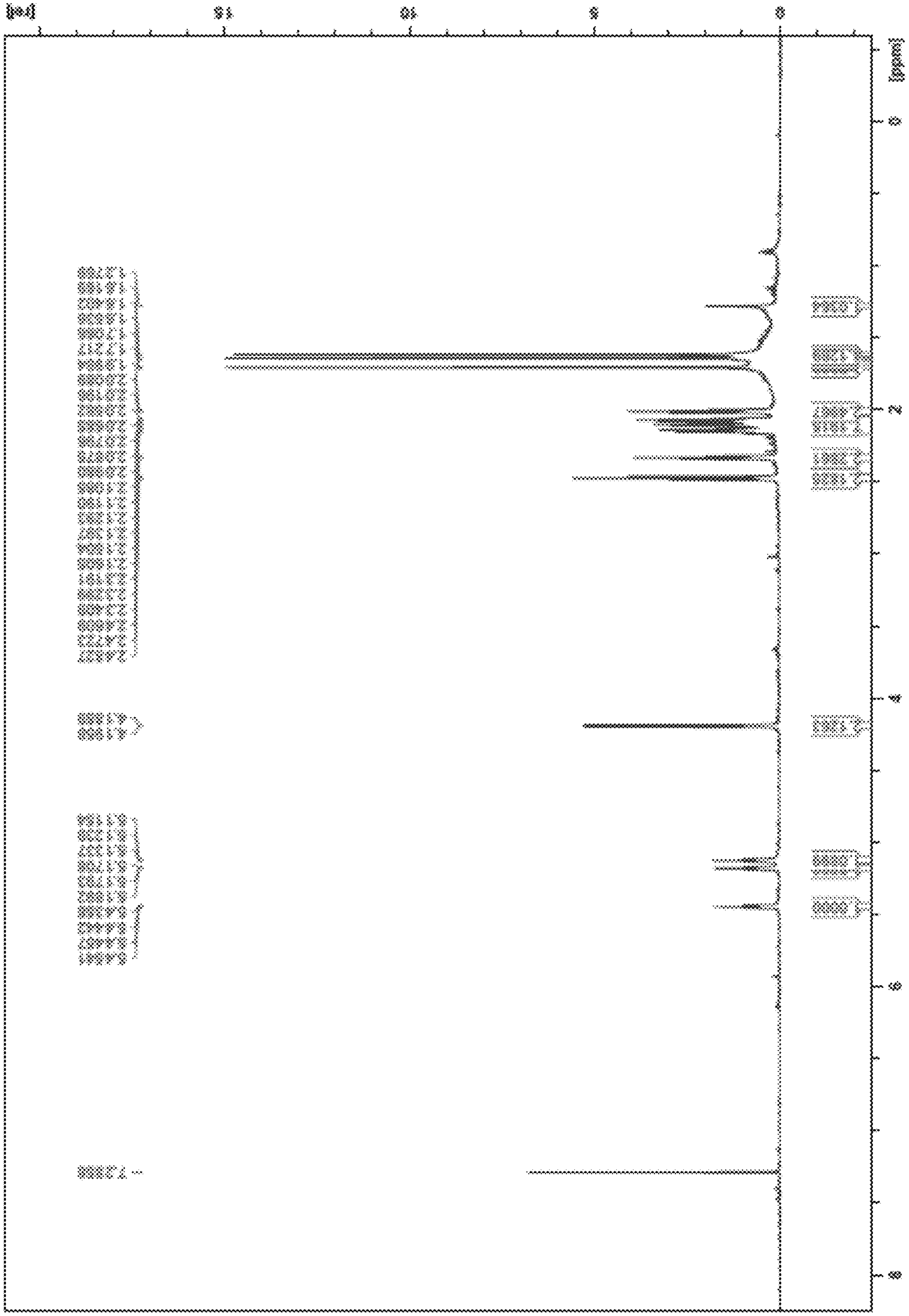
FIG. 18. SH-B proton spectrum.
Figure 19:
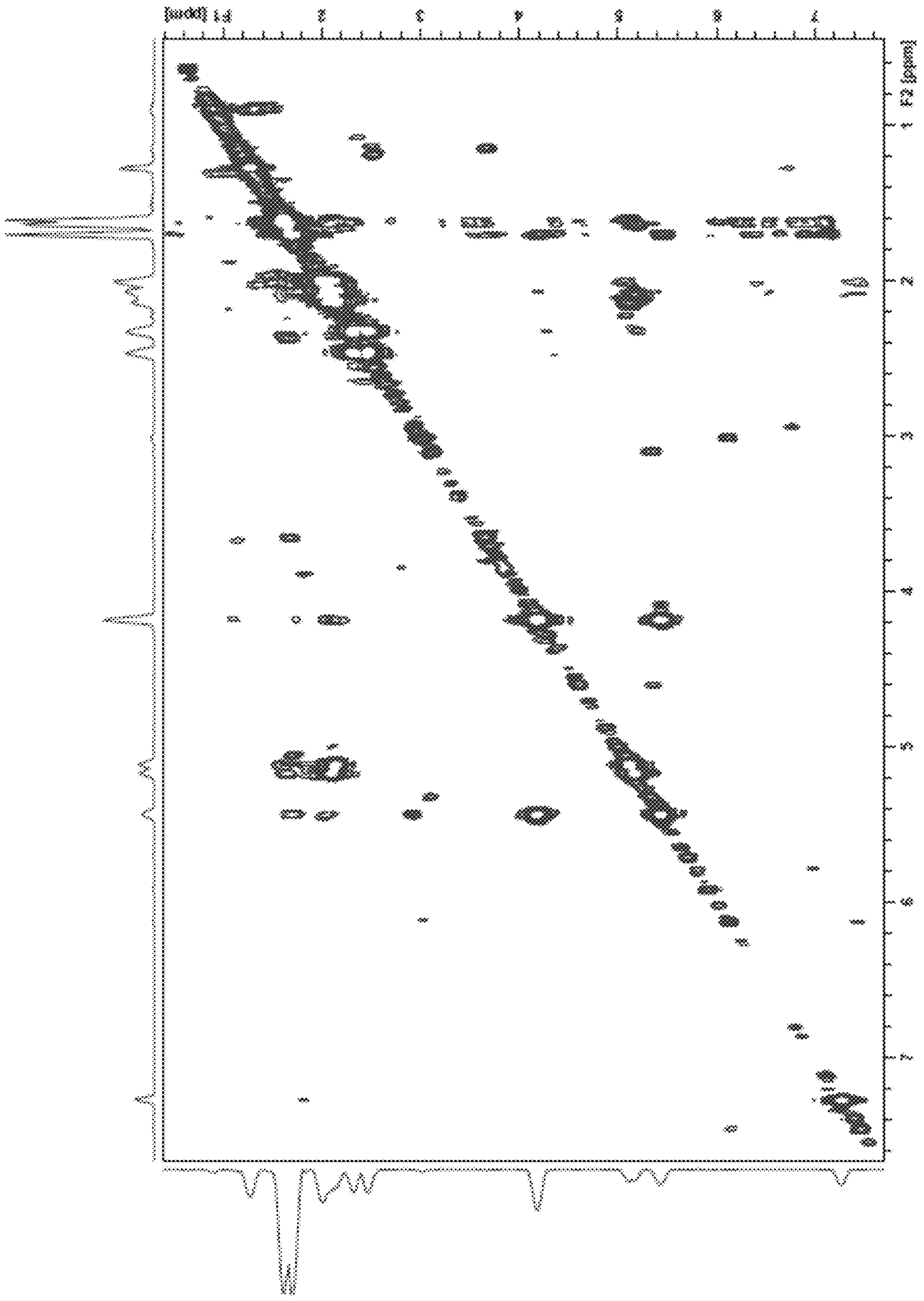
FIG. 19. SH-B COSY spectrum.
Figure 20:
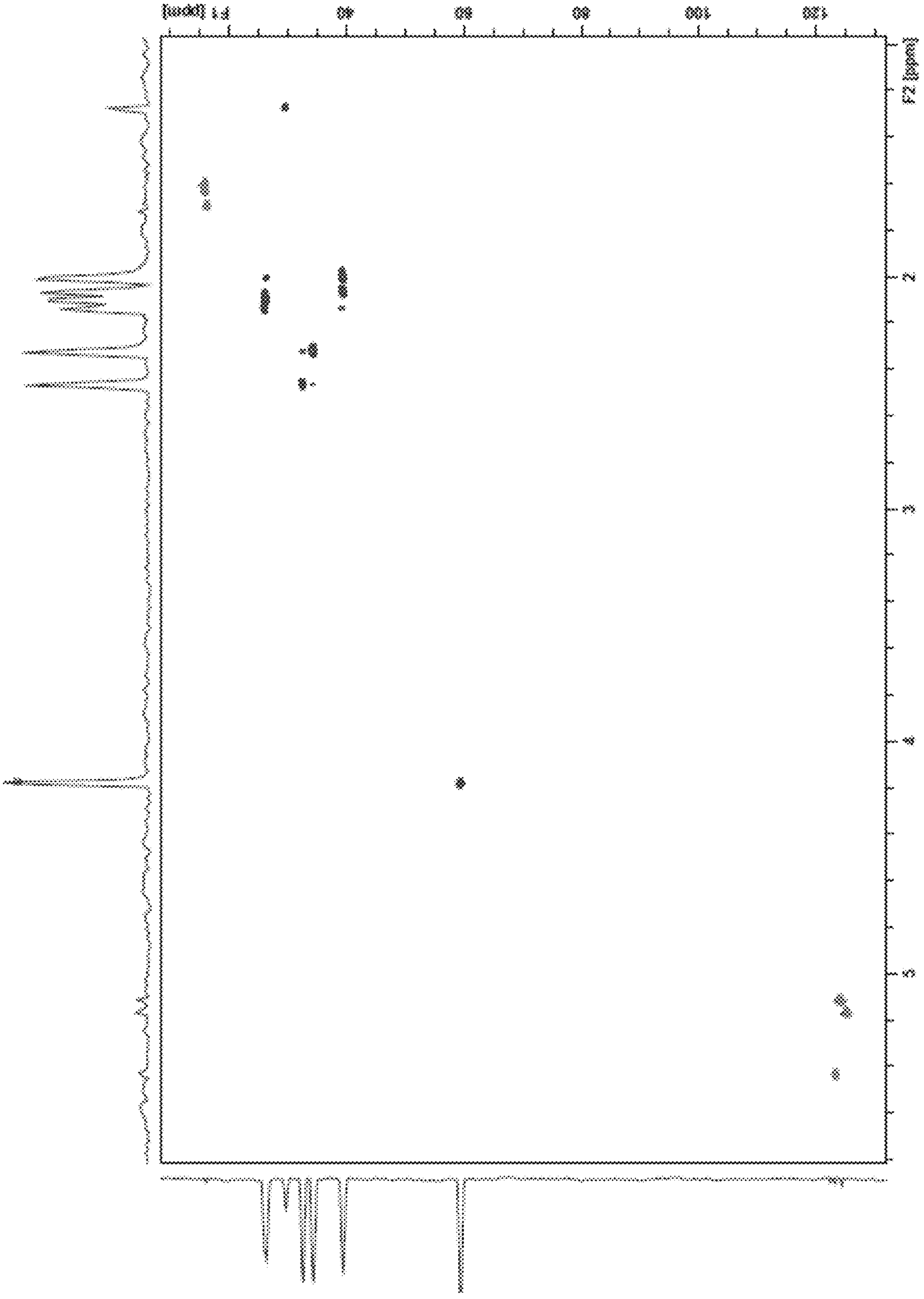
FIG. 20. SH-b HSQC spectrum.
Figure 21:
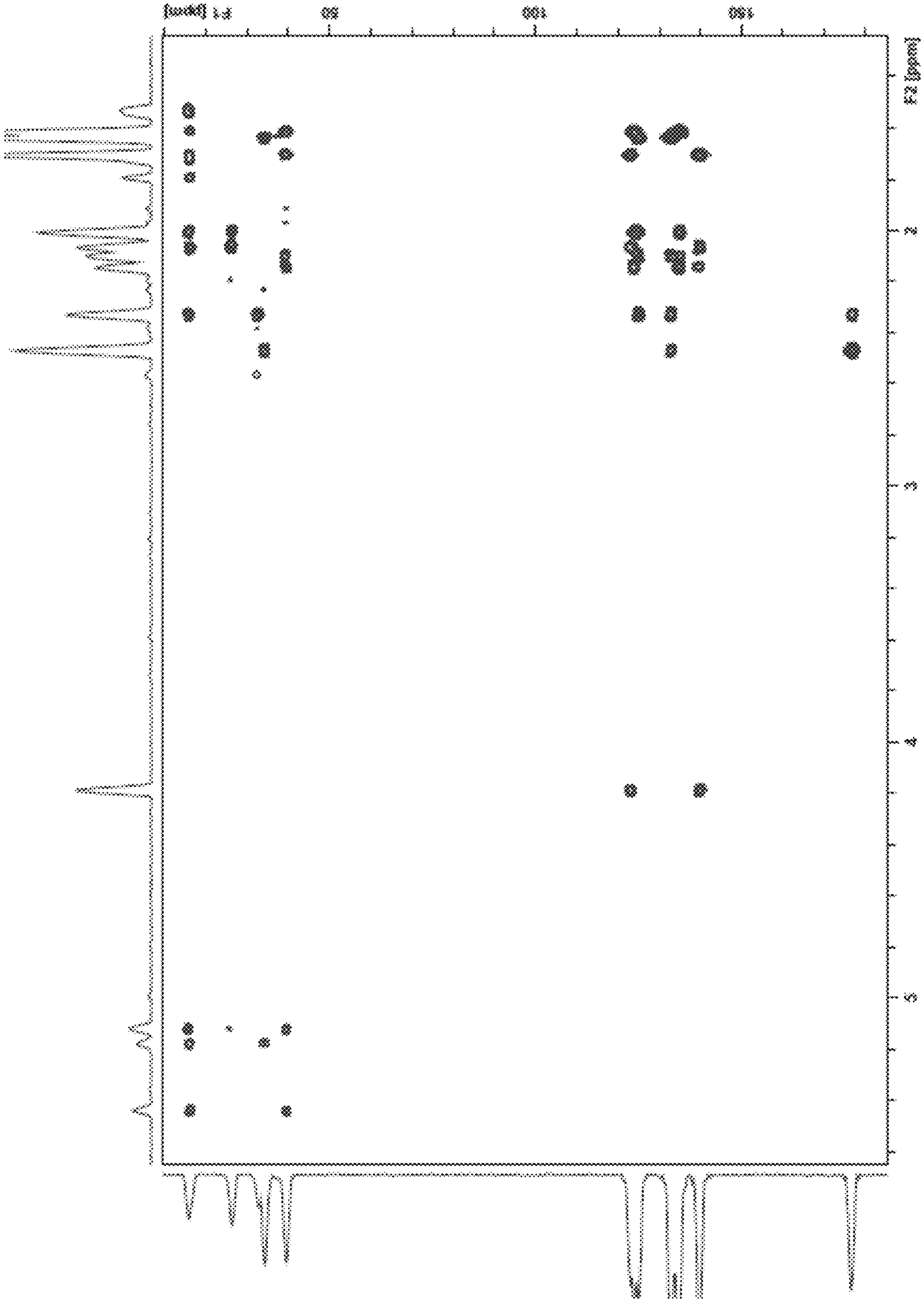
FIG. 21. SH-B HMBC spectrum.

Purified material with a mass spectrum ([M-H]=301.2 amu) of a diterpene-acid was analyzed by 1D ($^1$H and $^{13}$C) and 2D (COSY, NOESY, HSQC, HMBC) NMR spectroscopy to determine the chemical structure. The carbon spectrum showed chemical shifts for 20 carbon atoms, including three downfield shifts corresponding to a carboxylic acid (δC=184.91 ppm), and two olefinic carbons (δC=152.76 ppm and 104.58), the latter of which is shown to bear two protons by HSQC, and thus is an exocyclic methylene. In addition, the carbon spectrum and HSQC results show two methyls, nine methylenes, three methines, and three quaternary carbons. The proton spectrum showed two singlet methyl peaks, suggesting the methyl groups are connected to quaternary carbons, and these data together support that of an atiserene-based diterpene scaffold in which one of the methyl groups is oxidized to a carboxylic acid. This is confirmed by annotating COSY and HMBC correlations (FIG. 8 and FIG. 11). The relative stereochemistry of the molecule was confirmed by NOESY correlations around the constrained ring structure (FIG. 9).

The three dimensional structure, coupled to the biosynthetic origin from a confirmed ent-atiserene synthase allow us to assign the absolute stereochemistry as ent-atiserenoic acid. The structures of shunt metabolites SH_B and SH_C were determined with similar 2 d correlations, and by comparison to reported chemical shifts reported in the REAXYS database.

Synthesis of Methylatiserenoate by Solvolysis

Heating ent-atiserenoic acid in methanol with 1% sulfuric acid afforded a new product, methylatiserenoate, with a longer retention time by HPLC.

Example 2

An ent-atiserenoic acid gene cluster, PB20 (genotype: scarA P[5] RBS[5] ptmM1 T1 scarB P[6] RBS[8] ptmM2 T[3] scarD P[12] RBS[10] ptmM3 T[2] scare P[9] RBS[7] dxr T4 scarF synP ispD T[5] scarA synP ispE T[6] scarB P[9] RBS[9] ispF T[7] scarD P[10] RBS[8]idi T[9] scarE; SEQ ID NO:30), was introduced into *Streptomyces ceolicolor, Streptomyces* sp. GS-93, or *Streptomyces* sp.3211 with standard intergenic conjugation protocol. The exconjugants were selected on apramycin supplemented IWL-4 solid media. A total of 10 colonies were inoculated in 2.4 mL R2YE and ISM3 media and fermented for four days in a 24-well plate. At the day of harvest, the entire 24-well plate was centrifuged in a tabletop centrifuge at top speed for 30 minutes. Ten-fold dilution of the extraction was prepared by adding 100 μL supernatant to 900 μL methanol. Individual extraction was analyzed by reverse phase LCMS (buffer system: 10 mM ammonium formate, pH 8.3; 100% acetonitrile). Ent-atiserenoic acid yield is shown in Table 2.

TABLE 2

Ent-atiserenoic acid yield using alternative *Streptomyces* spp. host cells

| Strain | Medium | AUC | ug/mL (10-fold dilution) | mg/L |
|---|---|---|---|---|
| *Streptomyces ceolicolor* (1) | ISM3 | 5062.2086 | 0.5620 | 5.6200 |
| *Streptomyces ceolicolor* (2) | ISM3 | 748.581 | 0.3352 | 3.3518 |
| *Streptomyces* sp. GS-93 (3) | ISM3 | 4197.0967 | 0.5165 | 5.1651 |
| *Streptomyces* sp. GS-93 (4) | ISM3 | 4379.9766 | 0.5261 | 5.2613 |

TABLE 2-continued

Ent-atiserenoic acid yield using alternative *Streptomyces* spp. host cells

| Strain | Medium | AUC | ug/mL (10-fold dilution) | mg/L |
|---|---|---|---|---|
| *Streptomyces* sp. GS-93 (5) | ISM3 | 2128.1586 | 0.4077 | 4.0772 |
| *Streptomyces* sp. GS-93 (6) | ISM3 | 2915.8914 | 0.4491 | 4.4914 |
| *Streptomyces* sp. 3211 (7) | ISM3 | 13898.2826 | 1.0266 | 10.2662 |
| *Streptomyces* sp. 3211 (8) | ISM3 | 32368.5556 | 1.9978 | 19.9782 |
| *Streptomyces* sp. 3211 (9) | ISM3 | 27700.9468 | 1.7524 | 17.5238 |
| *Streptomyces* sp. 3211 (10) | ISM3 | 23643.9778 | 1.5391 | 15.3906 |
| *Streptomyces ceolicolor* (1) | R2YE | 223.1946 | 0.3076 | 3.0756 |
| *Streptomyces ceolicolor* (2) | R2YE | 610.3554 | 0.3279 | 3.2791 |
| *Streptomyces* sp. GS-93 (3) | R2YE | 370.1540 | 0.3153 | 3.1528 |
| *Streptomyces* sp. GS-93 (4) | R2YE | 668.9889 | 0.3310 | 3.3100 |
| *Streptomyces* sp. GS-93 (5) | R2YE | 567.0887 | 0.3256 | 3.2564 |
| *Streptomyces* sp. GS-93 (6) | R2YE | 991.7168 | 0.3480 | 3.4797 |
| *Streptomyces* sp. 3211 (7) | R2YE | 5536.3695 | 0.5869 | 5.8693 |
| *Streptomyces* sp. 3211 (8) | R2YE | 7982.4549 | 0.7156 | 7.1555 |
| *Streptomyces* sp. 3211 (9) | R2YE | 7946.4374 | 0.7137 | 7.1366 |
| *Streptomyces* sp. 3211 (10) | R2YE | 7645.9898 | 0.6979 | 6.9786 |

Example 3

An ent-atiserenoic acid gene cluster, PB La2 (genotype: P[11] RBS[10] ptmM1 T[1] P[4]RBS[6] ptmM2 T[3] P[4] RBS[6] ptmM3 T[2] P[12] RBS[9] dxr T[4] P[6] RBS[8] ispD T[5]P[5] RBS[5] ispE T[6] synP ispF T[7] synp idi T[9]; SEQ ID NO:31), was introduced into *Streptomyces albus* J1074 with standard intergenic conjugation protocol. A seed culture of the PB L2a-containing strain was grown in R2YE and then ISM3 for three days and used to inoculate 6×500 mL (total of 3 L) ISM3 cultures. Ent-atiserenoic acid production was assessed by collecting 5 mL of fermentation broth daily for seven days.

The cultures were separated into three groups and samples taken in duplicate: feed 0 (no feeding, take 5 mL sample daily); feed 1 (starting at 36 hours, supplement the culture with 5 g of glucose in the form of 10 mL glucose solution twice per day; take 5 mL sample daily); feed 2 (starting at 36 hours, supplement the culture with 10 g of glucose in the form of 20 mL glucose solution, 5 g yeast extract+malt extract, and 50 uL trace element per day; take 5 mL sample daily).

Each 5 mL sample was extracted by adding 5 mL methanol to 5 mL fermentation broth containing cell pellet and resin. The extraction mixture was incubated in a shaker for three hours. Subsequently, the extraction was diluted by 400-fold, then prepared as follows: the first dilution was prepared by adding 50 μL extraction to 950 μL methanol. The final dilution (400×) was made by taking 50 μL of first dilution to 950 μL methanol. The final dilution of the extract was analyzed by reverse phase LCMS (buffer system: 10 mM ammonium formate, pH 8.3; 100% acetonitrile.) The raw peak intensity of each sample was back calculated to concentration of ent-atiserenoic acid in the 400-fold diluted extraction by the standard curve (equation: [Peak intensity]= 18793×[μg/mL ent-atiserenoic acid]). The original concentration of ent-atiserenoic acid production is calculated by diluted concentration×400. Results are shown in Table 3.

TABLE 3

| Concentration of ent-atiserenoic acid by *S. albus* PB La2 | | | | | | |
|---|---|---|---|---|---|---|
| Day | Feed 0a | Feed 0b | Feed 1a | Feed 1b | Feed 2a | Feed 2b |
| 1 | 1.681477 | 11.70649 | 7.832704 | 0 | 4.831586 | 0 |
| 2 | 19.30506 | 94.14144 | 40.41931 | 32.26733 | 40.31288 | 16.55936 |
| 3 | 49.78449 | 59.55409 | 128.3669 | 41.46225 | 72.40994 | 15.47385 |
| 4 | 349.5983 | 199.7127 | 170.6806 | 147.7359 | 76.00702 | 34.43835 |
| 5 | 140.116 | 231.5969 | 133.9861 | 134.5395 | 126.4088 | 52.57277 |
| 6 | 925.3233 | 706.114 | 491.0977 | 524.2165 | 396.3816 | 406.5556 |
| 7 | 665.7372 | 385.4627 | 438.5463 | 503.8259 | 430.522 | 454.0414 |

Example 4

To identify enzymes that may be used in place of ent-atiserene synthase ptmM1 (accession number: ACO31274.1), the amino acid sequence of ent-atiserene synthase ptmM1 was obtained from Uniprot and subjected to BLAST analysis against the nr database (NCBI). The analysis identified the amino acid sequences identified below. A sequence alignment was performed by ClustalW multiple alignment application (1000 bootstraps) to calculate protein distance matrix. The phylogenetic analysis was performed using PHYLIP (University of Washington, Seattle, Wash.), and the phylogenetic tree was plotted in FigTree. A list of the sequences (accession number, protein name, species of origin) follows:

ACO3 1274.1 PtmT1 [*Streptomyces platensis*]

AHY18940.1 ent-atiserene synthase [*Streptomyces platensis*]

AHY18941.1 ent-atiserene synthase [*Streptomyces platensis*]

AHY18942.1 ent-atiserene synthase [*Streptomyces platensis*]

AHY18944.1 ent-atiserene synthase [*Streptomyces platensis*]

AHY18945.1 ent-atiserene synthase [*Streptomyces platensis*]

ADD83014.1 PtnT1 [*Streptomyces platensis*]

WP_030985278.1 hypothetical protein [*Streptomyces* sp. NRRL S-1813]

WP_030080417.1 hypothetical protein [*Streptomyces decoyicus*]

ACZ86631.1 hypothetical protein Sros_3708 [*Streptosporangium roseum* DSM 43021]

WP_005454079.1 4-hydroxybenzoate polyprenyltransferase [*Saccharomonospora cyanea*]

WP_005462072.1 4-hydroxybenzoate polyprenyltransferase [*Saccharomonospora glauca*]

WP_008028525.1 bacteriochlorophyll/chlorophyll synthetase [*Rhodobacter* sp. SW2]

WP_008280363.1 chlorophyll a synthase [*Roseovarius* sp. TM1035]

WP_009152840.1 4-hydroxybenzoate polyprenyltransferase-like prenyltransferase [*Saccharomonospora marina*]

WP_009455902.1 MULTISPECIES: homogentisate phytyltransferase [*Fischerella*]

WP_010997598.1 homogentisate phytyltransferase [*Nostoc* sp. PCC 7120]

WP_011908055.1 bacteriochlorophyll/chlorophyll a synthase [*Rhodobacter sphaeroides*]

WP_012616483.1 bacteriochlorophyll/chlorophyll synthetase [*Chloroflexus aggregans*]

WP_012796323.1 4-hydroxybenzoate polyprenyltransferase [*Saccharomonospora viridis*]

WP_016861644.1 homogentisate phytyltransferase [*Fischerella muscicola*]

WP_016874172.1 homogentisate phytyltransferase [*Chlorogloeopsis fritschii*]

WP_017310301.1 homogentisate phytyltransferase [*Fischerella* sp. PCC 9339]

WP_017319040.1 homogentisate phytyltransferase [*Mastigocladopsis repens*]

WP_017323227.1 homogentisate phytyltransferase [*Cyanobacterium* PCC 7702]

WP_017655775.1 homogentisate phytyltransferase [*Fortiea contorta*]

WP_017987983.1 hypothetical protein [*Amycolatopsis methanolica*]

WP_020420680.1 hypothetical protein [*Amycolatopsis* sp. ATCC 39116]

WP_022573875.1 chlorophyll synthase [Rhodobacteraceae bacterium HIMB 11]

ESW60080.1 bacteriochlorophyll/chlorophyll a synthase [*Rhodobacter* sp. CACIA14H1]

WP_024876751.1 4-hydroxybenzoate polyprenyltransferase [*Saccharomonospora* sp. CNQ490]

WP_026722928.1 homogentisate phytyltransferase [*Fischerella* sp. PCC 9431]

WP_027930452.1 hypothetical protein [*Amycolatopsis thermoflava*]

WP_029637774.1 homogentisate phytyltransferase [[*Scytonema hofmanni*] UTEX B 1581]

WP_030080417.1 hypothetical protein [*Streptomyces decoyicus*]

WP_030470347.1 hypothetical protein [*Lechevalieria aerocolonigenes*]

WP_031170430.1 hypothetical protein [*Streptosporangium roseum*]

KFL36038.1 hypothetical protein N788_05700 [*Arenimonas donghaensis* DSM 18148=HO3-R19]

WP_033358256.1 prenyltransferase [*Dactylosporangium aurantiacum*]

WP_034224802.1 4-hydroxybenzoate octaprenyltransferase [*Arenimonas donghaensis*]

WP_034260342.1 hypothetical protein [*Actinospica robiniae*]

WP_036015193.1 hypothetical protein [*Lentzea albidocapillata*]

WP_037261197.1 bacteriochlorophyll/chlorophyll a synthase [*Roseivivax halodurans*]

WP_037275502.1 prenyltransferase [*Rhodococcus rhodnii*]

WP_037308517.1 4-hydroxybenzoate polyprenyltransferase [*Saccharomonospora viridis*]

WP_007027364.1 4-hydroxybenzoate polyprenyltransferase-like prenyltransferase [*Saccharomonospora paurometabolica*]

WP_037571185.1 hypothetical protein [*Streptacidiphilus oryzae*]

WP_038007406.1 MULTISPECIES: bacteriochlorophyll/chlorophyll a synthase [*Thalassobacter*]

WP_039688771.1 bacteriochlorophyll/chlorophyll a synthase [*Tateyamaria* sp. ANG-S 1]

KIF37224.1 tocopherol phytyltransferase [*Hassallia byssoidea* VB512170]

WP_043143946.1 bacteriochlorophyll/chlorophyll a synthase [*Mameliella alba*]

WP_043655945.1 hypothetical protein [*Streptosporangium roseum*]

WP_043843101.1 hypothetical protein [*Amycolatopsis taiwanensis*]

WP_045313759.1 hypothetical protein [*Lechevalieria aerocolonigenes*]

WP_048599939.1 bacteriochlorophyll/chlorophyll a synthase [*Nereida ignava*]

WP_050530946.1 bacteriochlorophyll/chlorophyll a synthase [*Aestuariivita atlantica*]

WP_050930602.1 bacteriochlorophyll/chlorophyll a synthase [*Aestuariivita boseongensis*]

WP_053458409.1 homogentisate phytyltransferase [*Hapalosiphon* sp. MRB220]

WP_053738288.1 hypothetical protein [*Nocardia* sp. NRRL S-836]

KPP92134.1 chlorophyll synthase ChlG [Rhodobacteraceae bacterium HLUCCA08]

KPQ08812.1 chlorophyll synthase ChlG [Rhodobacteraceae bacterium HLUCCA09]

WP_057290696.1 4-hydroxybenzoate octaprenyltransferase [*Noviherbaspirillum* sp. Root 189]

WP_058123499.1 bacteriochlorophyll/chlorophyll a synthase [*Thalassobacter stenotrophicus*]

KU066555.1 cytochrome B562 [Alphaproteobacteria bacterium BRH_c36]

WP_062242826.1 homogentisate phytyltransferase [*Fischerella* sp. NIES-3754]

WP_062280982.1 MULTISPECIES: bacteriochlorophyll/chlorophyll a synthase [*Rhizobium*]

AOE07831.1 chlorophyll a synthase ChlG [uncultured bacterium]

WP_067765775.1 tocopherol phytyltransferase [*Nostoc* sp. NIES-3756]

WP_068353150.1 bacteriochlorophyll/chlorophyll a synthase [Rhodobacteraceae bacterium SB2]

WP_068361717.1 bacteriochlorophyll/chlorophyll a synthase [*Jannaschia* sp. EhC01]

WP_069210025.1 bacteriochlorophyll/chlorophyll a synthase [*Ruegeria* sp. PBVC088]

SDJ29593.1 chlorophyll synthase [*Lutimaribacter saemankumensis*]

SDC 18937.1 4-hydroxybenzoate polyprenyltransferase [*Prauserella marina*]

SDN46345.1 4-hydroxybenzoate polyprenyltransferase [*Streptomyces guanduensis*]

SDM79676.1 4-hydroxybenzoate polyprenyltransferase [*Lentzea violacea*]

SDX17745.1 4-hydroxybenzoate polyprenyltransferase [*Amycolatopsis xylanica*]

SES 11996.1 4-hydroxybenzoate polyprenyltransferase [*Phycicoccus cremeus*]

SER92449.1 4-hydroxybenzoate polyprenyltransferase [*Lentzea flaviverrucosa*]

SFJ85297.1 chlorophyll synthase [*Jannaschia pohangensis*]

SFA93839.1 4-hydroxybenzoate polyprenyltransferase [*Amycolatopsis marina*]

SFJ98404.1 4-hydroxybenzoate polyprenyltransferase [*Amycolatopsis sacchari*]

SFI62503.1 4-hydroxybenzoate polyprenyltransferase [*Streptosporangium canum*]

SFR25443.1 4-hydroxybenzoate polyprenyltransferase [*Lentzea waywayandensis*]

WP_071974050.1 bacteriochlorophyll/chlorophyll a synthase [*Sulfitobacter* sp. AMI-DI]

OJW42097.1 4-hydroxybenzoate polyprenyltransferase [*Thiobacillus* sp. 65-1059]

OJW84228.1 4-hydroxybenzoate polyprenyltransferase [*Thiobacillus* sp. 65-1402]

WP_072630499.1 bacteriochlorophyll/chlorophyll a synthase [*Planktotalea frisia*]

WP_072778091.1 bacteriochlorophyll/chlorophyll a synthase [*Marivita hallyeonensis*]

WP_072785392.1 4-hydroxybenzoate polyprenyltransferase [*Duganella sacchari*]

WP_052583874.1 4-hydroxybenzoate polyprenyltransferase, partial [*Actinopolyspora iraqiensis*]

WP_005443975.1 prenyltransferase UbiA [*Saccharomonospora azurea*]

EID53416.1 UbiA prenyltransferase family protein [*Saccharomonospora xinjiangensis* XJ-54]

EHK84863.1 4-hydroxybenzoate polyprenyltransferase-like prenyltransferase [*Saccharomonospora azurea* SZMC 14600]

EHK80706.1 4-hydroxybenzoate polyprenyltransferase-like prenyltransferase [*Saccharomonospora azurea* SZMC 14600]

EHY90523.1 4-hydroxybenzoate polyprenyltransferase-like prenyltransferase [*Saccharomonospora azurea* NA-128]

ABA23079.1 homogentisate phytyltransferase [*Anabaena variabilis* ATCC 29413]

WP_073555048.1 homogentisate phytyltransferase [*Fischerella major*]

WP_074201873.1 4-hydroxybenzoate polyprenyltransferase [*Sulfurivirga caldicuralii*]

WP_074621517.1 bacteriochlorophyll/chlorophyll a synthase [*Mameliella alba*]

WP_075787276.1 bacteriochlorophyll/chlorophyll a synthase [*Rhodovulum sulfidophilum*]

WP_076630627.1 bacteriochlorophyll/chlorophyll a synthase [*Tateyamaria omphalii*]

Example 5

Semi-Synthesis of Serofendic Acid

Reaction 1

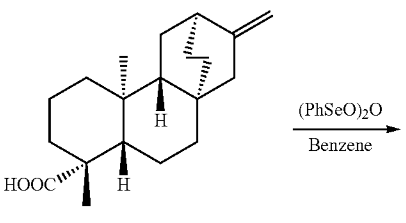

$C_{20}H_{30}O_2$
Intermediate 1

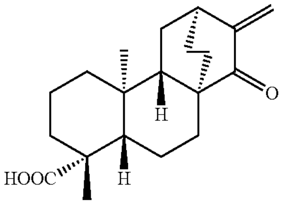

$C_{20}H_{28}O_3$
Intermediate 2

One molar equivalent of $(PhSeO)_2O$ (1.19 mg/mg intermediate 1) was added to a 5 mM solution of intermediate 1 in benzene (0.66 mL/mg intermediate 1) and refluxed for four hours. Ethyl acetate was added prior to rotary evaporation, which was followed by flash chromatography using 10:1 hexane-ethyl acetate. Fractions containing the intermediate 2 were identified by TLC.

Reaction 2

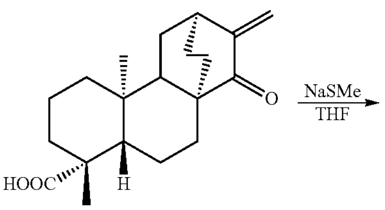

$C_{20}H_{28}O_3$
Intermediate 2

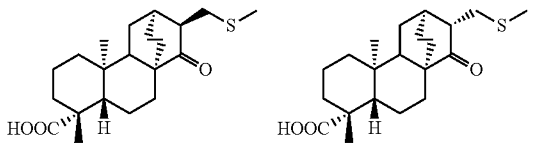

$C_{21}H_{32}O_3S$
Intermediates 3

One molar equivalent of NaSMe (15% in water, m/v; 1.48 μL/mg intermediate 2) was added to a 50 mM solution of intermediate 2 in THF (0.63 mL/mg intermediate 2) at room temperature. After 15 minutes, the reaction was diluted by a factor of five with NaCl brine. The product was extracted with ethyl acetate. The organic layer was washed with NaCl brine and dried with $CaCl_2$. Solvent was removed by rotary evaporation, and the product was purified by flash chromatography using 10:1 hexane-ethyl acetate. Fractions containing the intermediates 3 were identified by TLC.

Reaction 3

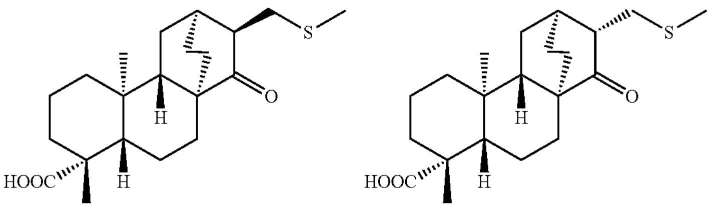

$C_{21}H_{32}O_3S$
Intermediates 3

-continued

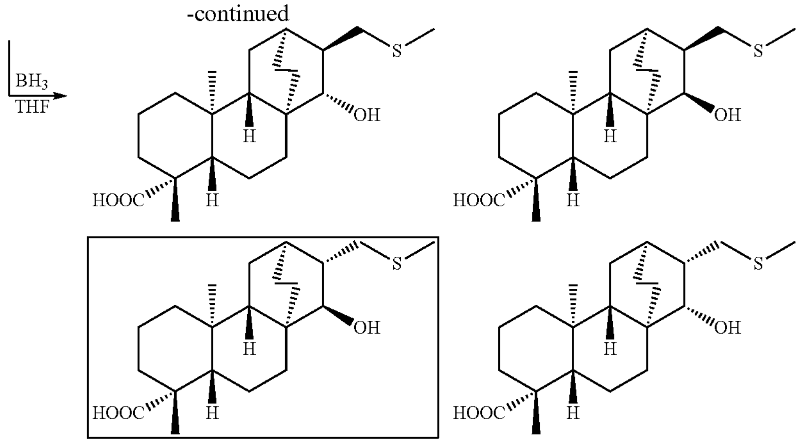

$C_{21}H_{34}O_3S$
Intermediates 4

A solution of intermediates 3 in THF was stirred at 0° C. Using a syringe, 370 μL of 1 M $BH_3$ in THF was added over 10 minutes. After one hour, 1 mL methanol and 1 mL 10% HCl were sequentially added. The product was extracted with petroleum ether. The organic layer was dried with $CaCl_2$, and solvent was removed by rotary evaporation. The product was purified by flash chromatography using 5:1 hexane-ethyl acetate. Fractions containing intermediates 4 were identified by TLC.

Reaction 4

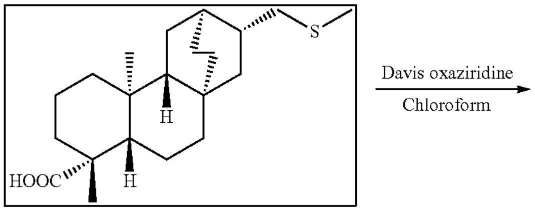

$C_{21}H_{34}O_3S$
Intermediate 4

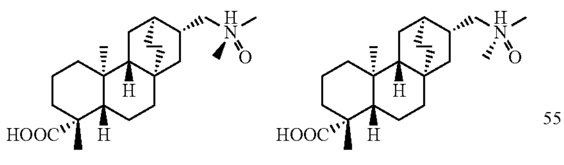

$C_{22}H_{36}O_4S^{2*}$
Serofendic acids

A solution with 100 mM intermediate 4 and 130 mM Davis oxaziridine in chloroform was stirred at room temperature for one hour. One mL petroleum ether and 1 mL 10% HCl were sequentially added. The aqueous layer was removed and extracted with petroleum ether. The organic extract was combined with the organic layer from the reaction and dried with $CaCl_2$, and solvent was removed by rotary evaporation. The product was purified by flash chromatography using a solvent gradient from ethyl acetate to 10:1 dichloromethane-methanol.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text
DNA sequence of Strain #3

(SEQ ID NO: 29)

GCTCTTCggagCCGGGCGGCTTCCTCATGCTTGACTTGACTAGGATAAAGGGGCTACAAGGAAG

AAGGAGGTTAACAaatgACCGCCGCCATCGTGAGTGTCGCCGCCCGCCCGCTGAGCACGGCGGT

GCGCCACGGCGACGTGGTGCTCGCCGACCGGCTGCACCTGGCGTCGGGCGCCCGCGAGGGCCGG

GTCCACCGGCTGCTCGCCGGGGCCCTCAGGGCACAGGGGCTGACGGTCCACACCGGCGGGGCCG

CCGTCGCCGGCGCCGAGGCACCCCAGGGCGCCGACGCACCGCTGGTGGAGATCGCCGCGCCGGT

CCGGCTCCCGGAGGCGGACGGTGACGCGCTGCTGTGCCTGGTGCGCGACGACACCGGATCGGAC

GCCGTCGACCGCGCCGAGGAGGCCCTGGCCCGGGTCCTGGGCGACTGGGAAGCCGCGAAGGGGG

ACCGAGCGGTGGCCCTGGCCGCCCCCCGGTCGTTCTGCGCCGGTGTGGACCGTGCCATCGAGAT

CGTCGAACGCGCCCTCGACCAGTACGGCGCCCCCGTCTACGTACGCAAGCAGATCGTCCACAAC

CGGCATGTCGTCGAGGACCTCGCCCGCCGCGGCGCGGTCTTCGTCGAGGAGCTTGACGAGGTGC

CGGAGGGCGAGCTGGTCGTCTTCTCCGCCCACGGGGTCGCCCCGGCGGTACGTGACGCGGCGGG

CGAGCGCGGTCTGCGAGTGATCGACGCGACCTGCCCGCTGGTCACCAAGGTCCATGCCGAGGCC

AAGCGGTTCGCGGGCCGCGGCGACACCGTCGTCCTGATCGGGCACGCCGGTCACGAGGAGGTCG

AGGGCACGCTGGGCGAGGCGCCCGACCGCACGGTGCTGGTGCAGAACGCGGCGGAGGCGGCGCG

CCTGGAGGTCGAGGACCCCGAGGCGGTCTCCTTCCTCATGCAGACCACGCTGGCGATGTCCGAG

GCCACCGAGGTGGCCCAGGCCCTGGCCGGCCGCTTCCCGTCGATCAAGGCACCGCAGTCCGAGG

ACATCTGCTACGCCTCGACCAACCGGCAGCGCGCCGTCGAGGAGATCGCCGGGCGGGTCGATCT

GCTCCTGGTGGTCGGATCGCCCAACTCCTCCAACTCCGTACGCCTGAAGGAACTCGCGGAGCGG

ATGGGCACCCCCGCCCAGCTGGTGGACGACGCCTCGTACGTCGGTCTGGAGCAGCTGCACGGGG

CCCGGCGGATCGGCCTGACGGCCGGCGCCTCGGCCCCGGACACCCTCGTCCAGGAAATCGTCGC

CAATCTCCGTGCCCTCGGACCCGTCACGGTCACCGAGCACCAAGTCGCGACGGAGAACGTCACC

TTCCAGCTGCCCAAAGAGCTGAGGAGCGCCCGGAAAGACCGCGCCCGCAAAGACTTGGAGAAGA

CCGTTGACAGCTGTtgatCTCGGTACCAAACCAATTATTAAAGACGCTGAAAAGCGTCTTTTTT

TGTTTCGGTCCtacttactCGCGTAGGCTAAAGATGACATCTTTAACATAGGATGTGCGCAAAA

AAAAGGGAGAGGAGCGTATTTaatGCCGACGACACCGCTGCGTCGTCCCACCCGGCAGCTGATG

CTCGGCGGCATGGGCGTCGGCAGCCGCCACCCCGTCTCGGTGCAGTCGATGACGACCACGGTGA

CGGCCGATGCCCAGGCCACCCTTCAGCAGATAGCCGAACTCACCGCGGCGGGCTGCGACATCGT

CCGGGTCGCCTGCCCCAGCCGGGACGACGCCGAAGCCCTCGCGGAGATCGCCCAGAAGTCGAAG

ATCCCCGTCATCGCGGACATCCACTTCCAGCCGCGCTATGTCTTCGCCGCGATCGAGGCGGGCT

GCGCCGGTGTCCGGGTCAACCCGGGCAACATCAAGGAATTCGACGACAAGATCAAGGAGATCGC

GCAGGCCGCGAAGGAGGCCGGCACCCCGATCCGCATCGGGGTCAACGCGGGCTCGCTCGACCCG

AGGATCCTGCGGAAGTTCGGCAAGGCGACCCCGGAGGCCCTGGCCGAATCGGCGCTGCGCGAGG

CGGAGCTCTTCGCGGAGCACGACTTCCACGACTTCAAGATCTCGGTGAAGCACCACGACCCGAT

GGTGATGATCCGGGCGTACGAGCTGCTGGCCGCGCAGTGCGACTACCCGCTCCACCTCGGCGTC

ACCGAGGCGGGACCGGCCTTCCAGGGCACGGTCAAGTCCTCGGTGGCCTTCGGCGCGCTGCTGC

GCCAGGGCATCGGCGACACCATCCGCGTCTCGCTGTCCGCACCGCCCGTGGAGGAGGTCAAGGT

CGGCATCCAGATCCTCCAGTCGCTCGGCCTGCGCCCCCGGCGCCTGGAGATCGTCTCCTGCCCG

TCCTGCGGCCGCGCCCAGGTGGACGTCTACAAGCTCGCCGAAGAGGTGAGCGCCGGGCTCGAAG

GGCTTCCGGTGCCGCTGCGGGTCGCCGTCATGGGCTGTGTCGTCAACGGTCCCGGCGAGGCCCG

-continued

CGAGGCCGACCTCGGTGTCGCCTCCGGCAACGGCAAGGGGCAGATCTTCGTCAAGGGCGAGGTC

GTCAAGACCGTCCCCGAGTCGAAGATCGTCGAGACCCTCATCGAAGAGGCACTGCGCCTCGCGG

ACGAGATGGGGGTGGACCTCGATGAGACTGGCTgatCTCGGTACCAAATTCCAGAAAAGAGACG

CTGAAAAGCGTCTTTTTTCGTTTTGGTCCaggtTCAAATGGCTAGGATATAACCTACACGATTA

GGATAGCCCCGCATCAATCAGAGAAGGAGGTACCAAaATGAGACTGGCTGACCTCACCGGTCCG

GGCGATCTCGCCGCACTGACGGAGGATCAACTCCAGGCGCTGGCCGCGGACATCCGCTCCTTTC

TCGTGGAGTCCGTTTCGAAGGTCGGCGGACACCTGGGCCCCAACCTCGGCGTCGTCGAGCTCAC

CCTCGCCCTGCACCGGGTCTTCGAGTCCCCCAAGGACACCCTGCTCTTCGACACCGGCCACCAG

GCCTACGTCCACAAGCTGCTCACCGGCCGGATGAAGGCCTTCTCGACGCTGCGCCAGGAAGGCG

GGCTCTCCGGCTATCCCGACCGCAGCGAGTCCGAGCACGATGTCATCGAGAACTCCCATGCCTC

CACGGCCCTTTCGTACGCAGACGGCATCGCCAAGGGCTTCGGCCTGGCCGGCGCCGCGCACCGC

AGGGTGGTCGCCGTCGTCGGCGACGGCGCGCTGACCGGCGGGATGAGCTGGGAGGCGCTCAACA

ACATCGGCGGCGCCCCGGACCGCCCGGTGATCATCGTCCTGAACGACAACGGCCGTTCCTACGC

CCCCACCGCCGGCGCCCTCGCCACCCACCTCGGCGAGCTCCGGGCGGGCCGCGGCGGGGCCGGT

CTCTTCGCGAACCTGGGCCTCGCCTACCTGGGCCCGGTCGACGGCCACGACCGCCCGGCACTCG

AGCGCGCACTGCGCCGGGCGGCCGCACTCGACCGCCCCGTGGTGGTGCACTGTGTGACGCAGAA

GGGCCACGGTTACGCACCGGCCGCCGAGGACCCCGACGACTGCTGGCACGCGGTGGGCACCTTC

GACCCCGAGACCGGCGGCAAGTCCGCTTCCGGCGGCCGCTCCTGGACCGCGGTGTTCGGTGCGG

AGATGACGGAACTCGGTGCGCAGCGGCCCGACGTGGTCGCCCTCACCGCCGCGATGCTCCAGCC

CGTGGGCCTGGCCGACTTCGCCCGCCGCTTCCCCGACCGGGTCTTCGACGTCGGCATCGGCGAA

CAGCATGCCGCCGTCTCCGCCGCCGGGCTGGCGCACACCGGGCTGCACCCCGTCGTGGCCGTCT

ACTCCACCTTCCTCAACCGCGCCTTCGACCAGGTGCTGATGGATGTGGCGCTGCACCGGCAGCC

GGTGACCTTCGTACTCGACCGGGCGGGTGTCACCGGCCCCGATGGCCCCAGCCATCACGGGATC

TGGGACGCCTCCTGGCTGTCGCTGGTACCGGGGCTGCGCCTGGCGGTGCCGCGCGATGCCGAGG

AACTCAGGACGCTGCTGCGGGAGGCGGTCGCCGTCACGGACGGGCCCACCGTCCTCCGCTTCCC

GAAGGCACAGGCCGGCCCGGCCGTGCCGGCGCTCCGCCGGGAGGGGGGCATGGACGTGCTGCAC

GAGGCGCCCGGCGCCCGGGTGCTGCTGGTCCCGACCGGTCCGCTCGCCGACCCGTGCCTTCAGG

CCGCGGCCGCGCTGGACGCCCTGGGCATCCCGTCGACGGTGGTGGACCCGCGCTGGTCCGTCCC

CGTACCGGAGGGGCTGCCGGAGCTGGCCGCACGGCACGAACTCGTGGTGACCGTCGAGGACAAC

CTGAGCGACGGCGGGCTCGGCGCGCGCCTGCTGCGACAGCTGTCCGAGGCCGGCACGCCCACCC

CCGTACGGACCGTCGGCCTGCCGACGGAGTTCCTTCCCCACGGCAGCAGGACGGCCCTCCTGCG

CCGGCATGGGCTCACCGCCGACGGCCTGGTCGCACGGGTCGGCGGATGGCTGCCACAAGCGGCC

CCCCGCTGACTCGGTACCAAACCAATTATTAAAGACGCTGAAAAGCGTCTTTTTTTGTTTCGGT

CCgcttCAGGTCGGCTGGTTGGCTGACAAAGTGCGTAGGATGACTGTGCATCAATCAGAGAAGG

AGGTACCAAATGACGTCGGAACTGCCCGCCGCACGCGGCGAAGGGCTGCGGAGCCTCGTCCGCA

TCCACCGGCTGGAATACCCCTTTCCGGTCATCTATCTCTGCCATGTCCTGTGGGGCGCCTGCCT

CGCGGCGACGGGTCCGGGCAGCCTGGCCGCCGCGCCCGTCCTGATCATGCTGTTCGCCAATATC

GTCGCGATCATCTCCCAGAACCCGCTCAACGCCGGTCTGGACATCCGGGCGGACACCCACACCA

GCGGCAAGGAGAGCATCGCCCGCGCCACCCAGCACCTCAGCGTCCGCACCGCGTTCACCTGCGC

GGCACTGGAGATGGCGCTCGCCCTCGGGCTGTCCGTCTGGGTCGCGCTCTGGCTCGGCCGGCCG

CTCGTCGCGGTGGGGGTGGCGCTGTCGATCGTGCTCCACCTCGCCTACAACCTGGAGCCGGTCC

-continued

GGCTGAAGCGGCGCGGCTACGCCAACCCCGCCTACTTCGGGGCGACCTTCGCCTTCCTGCCGTC
GCTGTCGACGTATGCGGCGGTGCGGGCGGACGTACCGCTCAGCGCGTGGCTGTTCCTCACCGGG
CTCGGCATCCTGCTGTTCGGCCGCTCCCTGTGGTGGTGCATCCCGGACCTGATCGGTGACGCCA
AGGCCGGGGACCGTACGCCCGCCGTACAGCACGGCCCGCGCCATGCGCTGGTGGTGGCGTGCCT
GTGGACCGCGCTCGGGCTGCTGTTCATCGGCGCCGGGCTGTGGCCGTACGGCGTCCTCTGGGCG
CTGCTCGGCATCCTGGCGAGCGCCGCCTTCCTCGTGGACAAGATCAAGCTGCTGCGGCACATCT
CGCGGGAGAACCTCCCGCACGAGTCCACGATGCGCAAGCACAGCCTCTCGCTGGCGATGGGCGG
CGACCTCCTGCTCTGCGCCATCCCGCTGCTCGCGCTCTGAtCAGATAAAAAAAATCCTTAGCTT
TCGCTAAGGATGATTTCTcgctACCCGTGGCTACTCAGCGAATAACTCTTGTAGGATACATAAA
AAAAAAAGGGAGAGGAGCGTATTTaATGCTCGAAGTTCCCGCTCAGCCCACGCCCGCCCCCCGC
GAGGCCGAGGCGGCCGCGCTGCTCGCGGCGACCGTCCACGACCCCTGGGGCCTGGTCGCTCCGT
CGGTGTACGACACCGCCCGGCTGGTCTCCCTCGCCCCGTGGCTCGACGGCCACCGGGAGCGTCT
CGGCTATCTGGTCGAGGAGCAGAACCAGGACGGAAGCTGGGGCGCACCCGACGGGTACGGCCTG
GTACCCACGCTCAGTGCGGTGGAGGCGCTGCTGACCGAACTCGCCCGGCCGGAATCCGGCGCGC
CGCACCCGCCCCACGACGACCTCGCCGCGGCCTGCGCCGGCGGTCTGGGCGCCCTCCAGGACGG
TCTGCTCGCCGGTCCGGTGCCCGACACCATCGGCGTCGAGTTCGTCGCGCCGTCCCTGCTCGCG
GACATCAACACCCGGCTGGCCGCGCTGACCGAGCAGGCACCCGGCAAGCTCGGGGCATGGTCCG
GCACCACCCTGACGTCACCGGCGCCCGACCTGGACGGTGCGCTGCTGGCCGGCGTCCGGGAGAT
GACCGAGCAGGCGCCGCTGCCGGAGAAGCTGTGGCACACACTGGAGGCCATCACCCGCGACGGC
ACCCGCGGTGCCCGGCCGCACGAGGGCGCACCGCCGCACAACGGCTCGGTCGGCTGCTCCCCCG
CCGCCACCGCCGCCTGGCTGGGCGCCTCGCCCGATCCGGCCGCGCCGGGCGTCGCCTATCTCCG
TGACGTCCAGGCGCGGTTCGGCGGGCCGGTGCCCTCGATCACCCCGATCGTCTACTTCGAGCAG
GCGTGGGTCCTCAACTCGCTGGCCGCCTCCGGCCTGCGCTACGAGGCCCCGGCCGCGCTCCTCG
ACAGCCTCGAAGCGGGTCTCACGGACGAGGGCACAGCCGCCGCCCCCGGTCTGCCGAGCGACTC
CGACGACACCGCCGCCGTCCTCTTCGCCCTGGCGCAGCACGGCAGGACGCACCGCCCCGACAGC
CTGATGCACTTCCGCCGGGACGGCTACTTCTCCTGCTTCGGCGTCGAGCGCACCCCCTCCACCA
GCACCAACGCACACATCCTGGAGGCCCTCGGCCATCACGTCACGGTGCGCCCCGACGACGCGGG
ACGCTATGGCGCGGAGATCCGGATGATCAGCGACTGGCTGCTGGACAACCAGCTGCCCGACGGC
AGCTGGATGGACAAGTGGCACGCCTCGCCGTACTACGCCACGGCCTGCTGTGCGCTGGCGCTCG
CCGAGTTCGGCGGCCCGTCCGCACGGGCCGCGGTCGGCCGGGCCGCCGCGTGGGCACTGGCGAC
CCAGCGCGCCGACGGCTCCTGGGGACGCTGGCAGGGCACCACGGAGGAGACCGCGTACATGGTG
CAGCTCCTGATGCGTACCCGTACCCCCGGGAGCCCGGGGACCGTCGCCCGGTCGGCGGCCCGCG
GCTGCGACGCGCTGCTGGCCCACGACGACCCGGCCTCCTACCCCGGGCTCTGGCACGACAAGGA
CATCTACGCGCCGGTGACCGTCATCCGGGCGGCGCGGCTCGCGGCACTGGCGCTCGGCGGCGCC
GAGTCCGCCGCTTCCGGAGGTGCTTGAtTCCGGCAATTAAAAAAGCGGCTAACCACGCCGCTTT
TTTTACGTCTGCAggagTAGCAGGGCTCCAAAACTAACGCCTGATGTAGGATCAGATGGCTACA
AGGAAGAAGGAGGTTAACAaTGCACGCTGACACAGTCCAGCCCCTCGAGAGCAGTGTCGACCTG
GCCCACCGCAACGCCTCGCGGGCCGCCGGCCTCGTCACGCCCGCCCTGCGGGCCACCGTCGACA
CCTTCGACAACCGCATCCGCCCCATCGTCGCCTACCACTTCGGCTGGATGGACACCAGCGGACG
CCCCACGGCGAACAGCGGCGGCAAGATGATCCGGGCGGCACTGACCATCCTTGCCGCCGAGGCC -continued

TGCGGCGGCGACGCCCAGCAGGCCGTACCCGGCGCCGCCGCCGTCGAACTGGTCCACAACTTCT

CGCTGTTGCACGACGACGTCATGGACCGCGATCTGGAGCGGCGCGGCCGGCCCACGGTATGGAG

CAAGTTCGGCACCCCCGCGGCGATCCTGGCGGGCGACATCCTGCTGGCGCGCGCCTGCGGCATG

TTCGACGAGGCCTCCGGCCACCAGGGCTGGGCGACCAAGGCCCTGATCGACGCGATCGCCGAGC

TGGCCGCGGGCCAGATGGCCGACCTCGCGCTGGAGCGCCGCGCCACGGTGACCCTGGAAGAGGC

CCTCACCGTCTCCGAGCAGAAGACCGCGGCGCTGCTGCGCTGCGCCTGCACGCTGGGCGCGGGA

CTCGTCGGCGCACCCGACGGGACCAGCCGCCGCTTCGGCGCCTTCGGTATGCACCTGGGCATGG

CGTTCCAGCTGGTCGACGACGTACTCGGCATATGGGGCGACCCGGCCGTCACCGGCAAGCCGGT

CCGCTCCGACCTGCACAACAAGAAGAAGAGCATTCCCGTCGTCGCCGCCCTCCACAGCGGCCGG

CCCGGCTCCGCGGAACTGGCCGCGCTCTACGCGGACACCGACCCCATGACGGAGGACGGCGCCC

GGCGCGCCGCCGAGCTGGTCGAGCTGGCCGGCGGCCGCGCCTGGACCGAGAGCGAGATCGAGCG

GCACCGCGGCCTCGCCGTGGCGCAGCTCGACGCCCTCGGGCTGACGGAGGCGCAGCGGGCACCC

CTGCTCGCCCTCGCCGACTACGTCGCCTTCAGGAAGCACTGAtGTCAGTTTCACCTGTTTTACG

TAAAAACCCGCTTCGGCGGGTTTTTACTTTTGGtactCGCGTAGGCTAAAGATGACATCTTTAA

CATAGGATGTGCGCAAAAAAAAGGGAGAGGAGCGTATTTaATGACCACCCGCCCCACGGCCGCC

TCGCGCGGCAACAAGTACCGCTTCGCCTTCCGCACCCTCTCCTTCCTGGACGCCCACAAGAACG

ACCGCTCCGGTGTGGCCGAGCTCAGCGGGCCGCCCGGCCGGGCGCTCCTGGTGTGGAAGCCGGA

GATCATCAGCCAGGTCTTCCGCGGCGACCGGAACATGACGCTGGAGGGCTCCGACACGCTCGGC

CCGCTGGTCGGCGACACCTCGCTGCTGTTCGCCAACGGGCCGCGGCACGCCGCGTACCGCCAGG

TGATCGGCCCGCGGCTGCGCGGCCGTCCGCTGCGCGGCTACGAGGAGCTGATCGCCGAGGCCAC

CCGGGCGGCGATCGACGAACTGCGGCCGGGCACCGACTTCCAGGTGCCCGACTGGACCCGCAGG

CTCACCCTTCAGATCGTCAGCCAGATCATCCTCGGCCCGGTGGACCACGGTCTGCTGCACCGCT

TCACCTCCTGGATCGAGGGGGTGCTGGGCTCGCGCGGCCGCACCCTCGCCTACCGCTATCTGCG

GCTGCCGCACGCCCTGCCGTCTCCCTGGCGCACCTTTGTGCGGCAGCGCGAGAGCCTGGACAAG

GAGCTGCTGTGCCCGGTGAGCGGCAAGAGCGCCGGCGGCGGTGCGGGTTCCGGTGCGCCGGAGC

CGTCGCCGGCCACGCTCGCCGAGGTGCTGCGCAGCGGTGAGGAGCCGCTCGGCCCGCTGGGCGA

CGGCGAACTGCGTGACCAGATCGTCTCGTTGCTGTTCGCGGGCCACGAGACGACCGCCTCGGCG

ATCTCCTGGGCGCTGTTCTGGCTCGCGGAGCACGACGAGGTGCGCCGCGACATCATCGACGAGC

TGAAGGCCACCTCCTCCAGCGGTGCGGCGGCGGAGGACGTACCGCTGCTGGACGCGGCCTGCCG

GGAGGTGCTGCGGATCTCGCCGCCCGCCGTGGTGGCCGGCAACCGTGTGCTCAACGAGGGCCAG

GAGATCGACGGGGTACCGCACGACGCGGGCACCCGGCTGACGCCGTGCATCTACCTGGCGCACC

AGCAGCCGGATCTCTACCCGCAGCCGGAGCGCTTCGACCCGCACCGCTTCCTGGGCAAGCGCAA

GTCCGCCCAGGAGTACCTGCCGTTCGGCGGCGGCACCCGCCGCTGTCTCGGTGCCGACCTCGCG

ATGCTGGAGATGCGGATGGTGGTGGCGGCGGTGCTGCGCCGGCGAGAACTGAAGTGCGTCAATC

CGGAGACCGGGGTACCGCAGCTGCGCGGTCCGGCGATGGGTCCGAGCGAAGACCTGAGAATGAC

GGTGACCGAGTGTCCAGCATGAtCTCGGTACCAAATTCCAGAAAAGAGACGCTGAAAAGCGTCT

TTTTTCGTTTTGGTCCaagtTCAAATGGCTAGGATATAACCTACACGATTAGGATAGCCCCGCA

TCAATCAGAGAAGGAGGTACCAAaaTGTGGGAGCCGACGTCTGCGGGGTGGGGTGCGCGGGTCG

AGGGGTGGGATCTGGGGGCGCCGTTGGGTGCGGAGTGTGCGGCGGCGTTGGTGGAGTTGTTCCG

TGCGCGGCATCTGCTGGTGTTTTCGGGTCAGGGTTTCTCGTTGGAGGAGCAGATCCGGTTCATG

GGGCATTTGGGTCCGGTGCTGCATGAGGAGGGTTCGGGGATCGGGTTTGTTTCGAATGTGAAGG

-continued

AGGGGGCTGCTCTGGGGGTGAGTGAGCTGTCTTTCCATTCGGATACGGGGCATTGTGCGGTGCC

GTTGGAGGCGGTGTCGCTTTTTGCTGAGGATGTTGAGGGGTGTGTGACGTCGACGCGGTTTGCG

AATGTGGCGGCGGCGTATGGGCGTTTGCCGGCGGGTTTGCGGTCGCGGGTTGCGGGACTGGTGT

GTGAGAACGCGATGCCGGTGTCGTTGGACGGCCGGAATGTGGGGTTGTCGGTGGCGGAGGGGAT

GCCGCGGGCGGAGCATCCGGTGGTGTGGCGTCATCCGGTGTCGGGGGAGCCGGGGCTGATGGTG

AATGCGAATCAGACGACGCGGATCGTGGGCCTTGAGGGTGAAGAGAGCCGGGGGTTGCTGGAGG

AGTTGTTCTCGGTGATGTATGCCGAGGATGCGGTGTATGAGCATTCCTGGCAGCAGGGGGATGT

GGTGATCTGGCACAACCTGGCGGTTCAGCATGCGCGGGGTGGCCTGGAAGGTAATGGCCGGCGG

ACTCTGCGCCGGGTGGCGTTGGGTGAGAAGGGGTTTTGGGAGCAGTGCCCGACCCTGCGTTACG

CCGATTTCAAAAACCAGCAGAACACCGCCGCGTgatAAAAAAAAAAAACACCCTAACGGGTGTT

TTTTTTTTTTTGGTCTCCCgcttCCCGTCGGCTGGAAACACTTGATCCAACTTAGGATACTTCC

TAATTCATTTTACTACAATTACGCGTTTACGTCAGaATGACGTACGTAATCGCGCAGCCCTGTG

TCGACCTCAAGGACAAGGCGTGCATCGAGGAGTGCCCGGTCGACTGCATCTACGAGGGCAAGCG

GTCCTTGTACATCCACCCGGACGAATGCGTCGACTGCGGTGCCTGTGAGCCGGTCTGCCCGGTC

GAGGCCATCTTCTACGAGGACGACACACCGGAGGAGTGGAAGGACTACTACAAGGCGAATGTGG

AGTTCTTCGACGAGCTCGGCTCGCCGGGCGGCGCCGCCCGGCTCGGCCTGATCGACCGCGACCA

CCCCGTCGTCGCGGCGCAGCCGGTCCGTACGGCCGGAGCCGCGGGCGAAtgatCTCGGTACCAA

AAAAAAAAAAAAAGACGCTGAAAAGCGTCTTTTTTTTTTTTGGTCCCgct

What is claimed is:

1. A recombinant cell comprising a host cell genetically modified to comprise heterologous polynucleotides that encode:

a polyprenyl diphosphate synthase;

a type II terpene cyclase;

a type I terpene cyclase;

a p450 monooxygenase; and a ferredoxin;

wherein the recombinant cell biosynthesizes ent-atiserenoic acid compared to a host cell that lacks the genetic modification of the recombinant cell.

2. The recombinant cell of claim 1 wherein the host cell comprises a *Streptomyces* spp. cell.

3. A method of biosynthesizing ent-atiserenoic acid, the method comprising:

culturing the recombinant cell of claim 1 under conditions effective for the recombinant cell to biosynthesize ent-atiserenoic acid.

4. The method of claim 3 further comprising isolating at least a portion of the ent-atiserenoic acid.

5. The method of claim 4 further comprising converting the ent-atiserenoic acid to serofendic acid.

* * * * *